United States Patent
Jazzar et al.

(10) Patent No.: US 12,168,224 B2
(45) Date of Patent: Dec. 17, 2024

(54) OPTICALLY PURE ENANTIOMERS OF RUTHENIUM COMPLEXES AND USES THEREOF

(71) Applicants: CENTRE NATIONAL DE LA RECHERCHE SCIENTIFIQUE, Paris (FR); UNIVERSITÉ D'AIX-MARSEILLE, Marseilles (FR); UNIVERSITE DE RENNES 1, Rennes (FR); INSTITUT NATIONAL DES SCIENCES APPLIQUÉES, Rennes (FR); ECOLE NATIONALE SUPÉRIEURE DE CHIMIE DE RENNES, Rennes (FR); UNIVERSITY OF CALIFORNIA, SAN DIEGO, La Jolla, CA (US)

(72) Inventors: Rodolphe Jazzar, La Jolla, CA (US); Guy Bertrand, Solana Beach, CA (US); François Vermersch, San Diego, CA (US); Nicolas Vanthuyne, Marseilles (FR); Jennifer Morvan, Pluméliau (FR); Marc Mauduit, Vitre (FR)

(73) Assignees: CENTRE NATIONAL DE LA RECHERCHE SCIENTIFIQUE, Paris (FR); UNIVERSITÉ D'AIX-MARSEILLE, Marseilles (FR); UNIVERSITE DE RENNES 1, Rennes (FR); INSTITUT NATIONAL DES SCIENCES APPLIQUÉES, Rennes (FR); ECOLE NATIONALE SUPÉRIEURE DE CHIMIE DE RENNES, Rennes (FR); UNIVERSITY OF CALIFORNIA, SAN DIEGO, La Jolla, CA (US)

( * ) Notice: Subject to any disclaimer, the term of this patent is extended or adjusted under 35 U.S.C. 154(b) by 0 days.

(21) Appl. No.: 18/004,341

(22) PCT Filed: Jul. 8, 2021

(86) PCT No.: PCT/EP2021/068995
§ 371 (c)(1),
(2) Date: Jan. 5, 2023

(87) PCT Pub. No.: WO2022/008656
PCT Pub. Date: Jan. 13, 2022

(65) Prior Publication Data
US 2024/0198321 A1    Jun. 20, 2024

(30) Foreign Application Priority Data
Jul. 8, 2020    (WO) .................. PCT/IB2020/000920

(51) Int. Cl.
*B01J 31/22* (2006.01)
*B01J 37/00* (2006.01)
*C07C 6/04* (2006.01)
*C07F 15/00* (2006.01)

(52) U.S. Cl.
CPC ....... *B01J 31/2291* (2013.01); *B01J 31/2226* (2013.01); *B01J 31/226* (2013.01); *B01J 31/2273* (2013.01); *B01J 37/009* (2013.01); *C07C 6/04* (2013.01); *C07F 15/0046* (2013.01); *B01J 2231/543* (2013.01); *B01J 2531/821* (2013.01); *C07C 2531/22* (2013.01)

(58) Field of Classification Search
None
See application file for complete search history.

(56) References Cited

U.S. PATENT DOCUMENTS

| 2013/0041122 A1* | 2/2013 | Holtcamp | C08F 32/08 526/171 |
|---|---|---|---|
| 2013/0137829 A1* | 5/2013 | Holtcamp | C08G 61/126 525/245 |
| 2014/0088277 A1* | 3/2014 | Stewart | C07C 57/26 558/429 |

FOREIGN PATENT DOCUMENTS

| WO | 2011/056881 A2 | 5/2011 | |
|---|---|---|---|
| WO | WO-2011056884 A2 * | 5/2011 | .......... B01J 31/2269 |
| WO | WO-2013025284 A1 * | 2/2013 | ................ C08F 4/80 |
| WO | WO-2013081726 A1 * | 6/2013 | ............ C08F 297/00 |

* cited by examiner

*Primary Examiner* — Tam M Nguyen
(74) *Attorney, Agent, or Firm* — WC&F IP

(57) ABSTRACT

The present invention relates to an optically pure (+) or (−) enantiomer of a ruthenium complex having formula (I) as well as the preparation method of said enantiomer, and uses thereof as catalyst, in particular in asymmetric olefin metathesis.

(I)

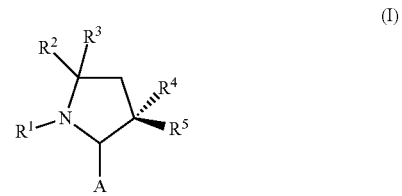

14 Claims, No Drawings

OPTICALLY PURE ENANTIOMERS OF RUTHENIUM COMPLEXES AND USES THEREOF

The present invention concerns new optically pure enantiomers of ruthenium complexes, as well as preparation methods thereof, and uses thereof as catalysts.

Since their discovery in early 1960s, N-heterocyclic carbenes (NHCs) have become inescapable ligands in transition-metal (TM) catalyzed transformations, in both academic and industrial research environments (*N-Heterocyclic Carbenes: From Laboratory Curiosities to Efficient Synthetic Tools* (Eds.: S. Diez-Gonzalez), RSC Catalysis series, RSC Publishing: Cambridge, 2011). In part, this growing popularity has been attributed to their remarkable aptitude in generating more stable, yet very reactive catalysts. Not surprisingly, chiral variants of diaminocarbenes naturally emerged in early 1990s, and thanks to their unique and highly modular steric environment, they also rapidly became privileged stereo-directing ligands with resounding successes in enantioselective catalysis ((a) Wang, F.; Liu, L.-J.; Wang, W.; Li, S.; Shi, M. Chiral NHC-Metal-Based Asymmetric Catalysis. *Coord. Chem. Rev.* 2012, 256, 804-853. (b) Janssen-Müller, D.; Schlepphorst, C.; Glorius, F. Privileged Chiral N-Heterocyclic Carbene Ligands for Asymmetric Transition-Metal Catalysis. *Chem. Soc. Rev.*, 2017, 46, 4845-4854).

Recently however, a new class of chiral carbenes namely chiral cyclic (alkyl)(amino) carbenes (CAACs) arose as a contender to NHCs's dominion over carbene driven enantioselective catalysis ((a) Lavallo, V.; Canac, Y.; Prasang, C.; Donnadieu, B.; Bertrand, G. Stable Cyclic (Alkyl)(Amino) Carbenes as Rigid or Flexible, Bulky, Electron-rich Ligands for Transition-Metal Catalysts: a Quaternary Carbon Atom Makes the Difference. *Angew. Chem., Int. Ed.* 2005, 44, 5705-5709. For a recent review on CAACs, see: (b) Soleilhavoup, M.; Bertrand, G. Cyclic (Alkyl)(Amino)Carbenes (CAACs): Stable Carbenes on the Rise; *Acc. Chem. Res.* 2015, 48, 256-266; (c) Melaimi, M., Jazzar, R., Soleilhavoup, M., Bertrand, G. *Angew. Chem. Int. Ed.*, 2017, 56, 10056). In recent years, CAAC ligands have been shown by Bertrand, Grubbs and others to afford robust and well-defined CAAC-Ru precatalysts demonstrating remarkable catalytic performances in several metathesis transformations (Marx, V. M.; Sullivan, A. H.; Melaimi, M.; Virgil, S. C.; Keitz, B. K.; Weinberger, D. S.; Bertrand, G.; Grubbs, R. H. Cyclic Alkyl Amino Carbene (CAAC) Ruthenium Complexes as Remarkably Active Catalysts for Ethenolysis. *Angew. Chem., Int. Ed.* 2015, 54, 1919-1923. (b) Zhang, J.; Song, S.; Wang, X.; Jiao, J.; Shi, M. Ruthenium-Catalyzed Olefin Metathesis Accelerated by the Steric Effect of the Backbone Substituent in Cyclic (Alkyl)(Amino) Carbenes. *Chem. Commun.* 2013, 49, 9491-9493. (c) Anderson, D. R.; Lavallo, V.; O'Leary, D. J.; Bertrand, G.; Grubbs, R. H. Synthesis and Reactivity of Olefin Metathesis Catalysts Bearing Cyclic (Alkyl)(Amino)Carbenes. *Angew. Chem., Int. Ed.* 2007, 46, 7262-7265). Pioneered by Grubbs, Hoveyda and others, a slew of chiral diaminocarbene ligands and catalysts have been reported in recent years, with varying successes in asymmetric ring-opening cross-metathesis (AROCM)(Berlin, J. M.; Goldberg, S. D.; Grubbs, R. H. Highly Active Chiral Ruthenium Catalyst for Asymmetric Cross-Metathesis and Ring-Opening Cross-Metathesis. *Angew. Chem. Int. Ed.* 2006, 45, 7591-7595) and ring-closing metathesis (ARCM) transformations (Van Veldhuizen, J. J.; Gillingham, D. G.; Garber, S. B.; Kataoka, O.; Hoveyda, A. H. Chiral Ru-Based Complexes for Asymmetric Olefin Metathesis: Enhancement of Catalyst Activity through Steric and Electronic Modifications. *J. Am. Chem. Soc.* 2003, 125, 12502-12508).

Nevertheless, as a major drawback, number of these catalysts were obtained following tedious low yielding procedures, and very often only one of the two enantiomers was prepared.

The aim of the present invention is thus to provide new optically pure ruthenium complexes that could be used for asymmetric catalysis.

Another aim of the present invention is to provide new optically pure ruthenium complexes to be used as catalysts for example for olefin metathesis.

Another aim of the present invention is to provide new optically pure ruthenium complexes that could be prepared by a process more economic and faster in comparison with the prior art processes.

The present invention relates to an optically pure (+) or (−) enantiomer of a ruthenium complex having the following formula (I):

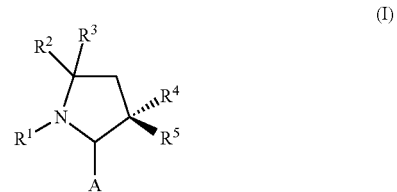

wherein:
- $R^1$ is a $(C_6-C_{14})$aryl group, a $(C_1-C_6)$alkyl group or a $(C_8-C_{20})$cycloalkyl group, said aryl group being optionally substituted with at least one substituent chosen from the group consisting of: halogen, $(C_6-C_{10})$aryl group, and $(C_1-C_6)$alkyl group, said alkyl group being optionally substituted with one or several phenyl group(s),
- or $R^1$ is a —$NR'_aR'_b$ group, $R'_a$ and $R'_b$ being independently from each other selected from the group consisting of: H, $(C_1-C_6)$alkyl, and $(C_6-C_{10})$aryl;
- $R^2$ is H, a $(C_6-C_{10})$aryl group or a $(C_1-C_6)$alkyl group;
- $R^3$ is a $(C_1-C_6)$alkyl group; or $R^2$ and $R^3$ may together form, with the carbon atom carrying them, a $(C_3-C_6)$ cycloalkyl;
- $R^4$ is selected from the following groups: $(C_6-C_{20})$aryl, $(C_6-C_{10})$alkyl, and $(C_3-C_{12})$cycloalkyl group, said aryl group being optionally substituted with at least one substituent chosen from the group consisting of: $(C_1-C_6)$alkyl, optionally substituted with one or several phenyl group(s), $(C_6-C_{10})$aryl$(C_1-C_6)$alkyl, and $(C_6-C_{10})$aryl, optionally substituted with one or several substituents, in particular selected in the group consisting of: $(C_1-C_6)$alkylamino, di$(C_1-C_6)$alkylamino, $(C_1-C_6)$alkoxy, and $(C_1-C_6)$alkyl;
- $R^5$ is selected from the following groups: $(C_6-C_{20})$aryl, $(C_6-C_{10})$alkyl, $(C_3-C_{12})$cycloalkyl, heteroaryl, $(C_6-C_{10})$aryl$(C_1-C_6)$alkyl, and heteroaryl$(C_1-C_6)$alkyl, said aryl group being optionally substituted with at least one substituent chosen from the group consisting of: $(C_1-C_6)$alkyl, optionally substituted with one or several phenyl group(s), $(C_6-C_{10})$aryl$(C_1-C_6)$alkyl, and $(C_6-C_{10})$aryl, optionally substituted with one or several substituents, in particular selected in the group consisting of: $(C_1-C_6)$alkylamino, di$(C_1-C_6)$alkylamino, $(C_1-C_6)$alcoxy, and $(C_1-C_6)$alkyl;

with the proviso that $R^5$ is different from $R^4$;

A is either a group of formula (1) or a group of formula (2):

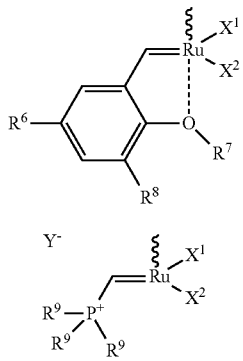

(1)

(2)

wherein:

$X^1$ is an halogen atom, a $(C_1-C_6)$alkoxy group or a —S—$(C_6-C_{10})$aryl group;

$X^2$ is an halogen atom or a $(C_1-C_6)$alkoxy group;

or $X^1$ and $X^2$ may form together with the ruthenium atom carrying them a heterocycloalkyl group fused with a phenyl group, said phenyl group being possibly substituted with at least one halogen atom, $R^6$ is H or is selected from the following groups: nitro, cyano, $(C_1-C_6)$alkyl, cycloalkyl, $(C_1-C_6)$alkoxy, cycloalkyloxy, $(C_6-C_{10})$aryl, heteroaryl, $(C_6-C_{10})$aryloxy, heteroaryloxy, $(C_1-C_6)$alkylcarbonyl, arylcarbonyl, $(C_1-C_6)$alkoxycarbonyl, aryloxycarbonyl, carboxyl, amido, $(C_1-C_6)$alkylsulfonyl, arylsulfonyl, $(C_1-C_6)$alkylsulfinyl, arylsulfinyl, $(C_1-C_6)$alkylthio, arylthio, sulfonamide, halogen, —$NR_aR_b$, —$SO_2$—NRR', and —$N(R_c)$—C(=O)—$R_c$, $R_a$ and $R_b$ being independently selected from H and $(C_1-C_6)$alkyl, R and R' being selected from the following groups: $(C_1-C_6)$alkyl, $(C_6-C_{10})$aryl, heteroaryl, and halo$(C_1-C_6)$alkyl, $R_c$ being H or being selected from the following groups: $(C_1-C_6)$alkyl, $(C_6-C_{10})$aryl, and heteroaryl, $R_d$ being H or selected from the following groups: $(C_1-C_6)$alkyl, halo$(C_1-C_6)$alkyl, cycloalkyl, $(C_6-C_{10})$aryl, heteroaryl, $(C_1-C_6)$alkoxy, cycloalkyloxy, $(C_6-C_{10})$aryloxy, and heteroaryloxy;

$R^7$ is a $(C_1-C_6)$alkyl group;

$R^9$ is a $(C_1-C_6)$alkyl group; and $R^8$ is H, a $(C_6-C_{10})$aryl group or a $(C_1-C_6)$alkyl group; and $Y^-$ is a non-coordinating inorganic anion, and is preferably $PF_6^-$, $SbF_6^-$ or $BF_4^-$.

The compounds of the invention may also be represented by the following formula:

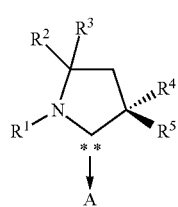

Preferably, in formula (1), $R^8$ is H.

Preferably, in formula (1), $R^1$, $R^2$ and $R^3$ are selected from alkyl groups, and more preferably are methyl groups.

Preferably, in formula (1), $R^5$ is selected from alkyl groups, and more preferably is a methyl group, and $R^4$ is selected from the following groups: $(C_6-C_{20})$aryl, $(C_1-C_{10})$alkyl, and $(C_3-C_{12})$cycloalkyl, said aryl group being optionally substituted with at least one substituent chosen from the group consisting of: $(C_1-C_6)$alkyl, optionally substituted with one or several phenyl group(s), $(C_6-C_{10})$aryl$(C_1-C_6)$alkyl, and $(C_6-C_{10})$aryl, optionally substituted with one or several substituents, in particular selected in the group consisting of: $(C_1-C_6)$alkylamino, di$(C_1-C_6)$alkylamino, $(C_1-C_6)$alcoxy, and $(C_1-C_6)$alkyl.

The present invention is based on the use of $^{Prep}$HPLC as a simple and practical tool to obtain optically pure (>99% ee) (R)- and (S)-CAAC-Ru metathesis catalysts in almost quantitative yields, as explained below in the examples. The compounds of the invention yield active, but more importantly very selective catalysts for asymmetric ring-opening cross-metathesis (AROCM) reactions.

The present invention relates to a ruthenium complex having the following formula (I'):

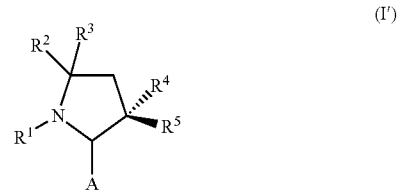

(I')

wherein:

$R^1$ is a —$NR'_aR'_b$ group, $R'_a$ and $R'_b$ being independently from each other selected from the group consisting of: H, $(C_1-C_6)$alkyl, and $(C_6-C_{10})$aryl;

$R^2$ is H, a $(C_6-C_{10})$aryl group or a $(C_1-C_6)$alkyl group;

$R^3$ is a $(C_1-C_6)$alkyl group; or $R^2$ and $R^3$ may together form, with the carbon atom carrying them, a $(C_3-C_6)$ cycloalkyl;

$R^4$ is selected from the following groups: $(C_6-C_{20})$aryl, $(C_1-C_{10})$alkyl, and $(C_3-C_{12})$cycloalkyl group, said aryl group being optionally substituted with at least one substituent chosen from the group consisting of: $(C_1-C_6)$alkyl, optionally substituted with one or several phenyl group(s), $(C_6-C_{10})$aryl$(C_1-C_6)$alkyl, and $(C_6-C_{10})$aryl, optionally substituted with one or several substituents, in particular selected in the group consisting of: $(C_1-C_6)$alkylamino, di$(C_1-C_6)$alkylamino, $(C_1-C_6)$alcoxy, and $(C_1-C_6)$alkyl;

$R^5$ is selected from the following groups: $(C_6-C_{20})$aryl, $(C_6-C_{10})$alkyl, $(C_3-C_{12})$cycloalkyl, heteroaryl, $(C_6-C_{10})$aryl$(C_1-C_6)$alkyl, and heteroaryl$(C_1-C_6)$alkyl, said aryl group being optionally substituted with at least one substituent chosen from the group consisting of: $(C_1-C_6)$alkyl, optionally substituted with one or several phenyl group(s), $(C_6-C_{10})$aryl$(C_1-C_6)$alkyl, and $(C_6-C_{10})$aryl, optionally substituted with one or several substituents, in particular selected in the group consisting of: $(C_1-C_6)$alkylamino, di$(C_1-C_6)$alkylamino, $(C_1-C_6)$alcoxy, and $(C_1-C_6)$alkyl;

with the proviso that $R^5$ is different from $R^4$;

A is either a group of formula (1) or a group of formula (2):

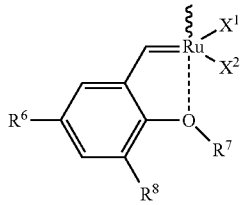
(1)

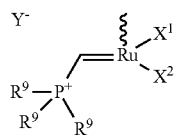
(2)

wherein:

$X^1$ is an halogen atom, a $(C_1\text{-}C_6)$alkoxy group or a —S—$(C_6\text{-}C_{10})$aryl group;

$X^2$ is an halogen atom or a $(C_1\text{-}C_6)$alkoxy group;

or $X^1$ and $X^2$ may form together with the ruthenium atom carrying them a heterocycloalkyl group fused with a phenyl group, said phenyl group being possibly substituted with at least one halogen atom, $R^6$ is H or is selected from the following groups: nitro, cyano, $(C_1\text{-}C_6)$alkyl, cycloalkyl, $(C_1\text{-}C_6)$alkoxy, cycloalkyloxy, $(C_6\text{-}C_{10})$aryl, heteroaryl, $(C_6\text{-}C_{10})$aryloxy, heteroaryloxy, $(C_1\text{-}C_6)$alkylcarbonyl, arylcarbonyl, $(C_1\text{-}C_6)$alkoxycarbonyl, aryloxycarbonyl, carboxyl, amido, $(C_1\text{-}C_6)$alkylsulfonyl, arylsulfonyl, $(C_1\text{-}C_6)$alkylsulfinyl, arylsulfinyl, $(C_1\text{-}C_6)$alkylthio, arylthio, sulfonamide, halogen, —$NR_aR_b$, —$SO_2$—NRR', and —$N(R_c)$—$C(=O)$—$R_c$, $R_a$ and $R_b$ being independently selected from H and $(C_1\text{-}C_6)$alkyl, R and R' being selected from the following groups: $(C_1\text{-}C_6)$alkyl, $(C_6\text{-}C_{10})$aryl, heteroaryl, and halo$(C_1\text{-}C_6)$alkyl, $R_c$ being H or being selected from the following groups: $(C_1\text{-}C_6)$alkyl, $(C_6\text{-}C_{10})$aryl, and heteroaryl, $R_d$ being H or selected from the following groups: $(C_1\text{-}C_6)$alkyl, halo$(C_1\text{-}C_6)$alkyl, cycloalkyl, $(C_6\text{-}C_{10})$aryl, heteroaryl, $(C_1\text{-}C_6)$alkoxy, cycloalkyloxy, $(C_6\text{-}C_{10})$aryloxy, and heteroaryloxy;

$R^7$ is a $(C_1\text{-}C_6)$alkyl group;

$R^9$ is a $(C_1\text{-}C_6)$alkyl group; and $R^8$ is H, a $(C_6\text{-}C_{10})$aryl group or a $(C_1\text{-}C_6)$alkyl group; and $Y^-$ is a non-coordinating inorganic anion, and is preferably $PF_6^-$, $SbF_6^-$ or $BF_4^-$.

said complex being in the form of a racemic mixture, or in the form of an optically pure (+) or (−) enantiomer.

The present invention relates to an optically pure (+) or (−) enantiomer of a ruthenium complex having the following formula (1-1):

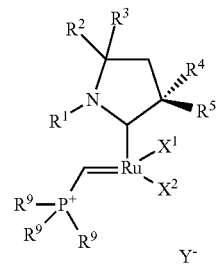
(I-1)

wherein:

$R^1$ is a $(C_6\text{-}C_{14})$aryl group, a $(C_1\text{-}C_6)$alkyl group or a $(C_8\text{-}C_{20})$cycloalkyl group, said aryl group being optionally substituted with at least one substituent chosen from the group consisting of: halogen, $(C_6\text{-}C_{10})$aryl group, and $(C_1\text{-}C_6)$alkyl group, said alkyl group being optionally substituted with one or several phenyl group(s);

$R^2$ is H, a $(C_6\text{-}C_{10})$aryl group or a $(C_1\text{-}C_6)$alkyl group;

$R^3$ is a $(C_1\text{-}C_6)$alkyl group; or $R^2$ and $R^3$ may together form, with the carbon atom carrying them, a $(C_3\text{-}C_6)$ cycloalkyl;

$R^4$ is selected from the following groups: $(C_6\text{-}C_{20})$aryl, $(C_6\text{-}C_{10})$alkyl, and $(C_3\text{-}C_{12})$cycloalkyl group, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6\text{-}C_{10})$aryl, optionally substituted with one or several substituents, in particular selected in the group consisting of: $(C_1\text{-}C_6)$alkylamino, di$(C_1\text{-}C_6)$alkylamino, $(C_1\text{-}C_6)$alcoxy, and $(C_1\text{-}C_6)$alkyl;

$R^5$ is selected from the following groups: $(C_6\text{-}C_{20})$aryl, $(C_6\text{-}C_{10})$alkyl, $(C_3\text{-}C_{12})$cycloalkyl, heteroaryl, $(C_6\text{-}C_{10})$aryl$(C_1\text{-}C_6)$alkyl, and heteroaryl$(C_1\text{-}C_6)$alkyl, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6\text{-}C_{10})$aryl, optionally substituted with one or several substituents, in particular selected in the group consisting of: $(C_1\text{-}C_6)$alkylamino, di$(C_1\text{-}C_6)$alkylamino, $(C_1\text{-}C_6)$alcoxy, and $(C_1\text{-}C_6)$alkyl;

with the proviso that $R^5$ is different from $R^4$;

$X^1$ is an halogen atom, a $(C_1\text{-}C_6)$alkoxy group or a —S—$(C_6\text{-}C_{10})$aryl group;

$X^2$ is an halogen atom or a $(C_1\text{-}C_6)$alkoxy group;

or $X^1$ and $X^2$ may form together with the ruthenium atom carrying them a heterocycloalkyl group fused with a phenyl group, said phenyl group being possibly substituted with at least one halogen atom, $Y^-$ is a non-coordinating inorganic anion, and is preferably $PF_6^-$, $SbF_6^-$ or $BF_4^-$; and $R^9$ is a $(C_1\text{-}C_6)$alkyl group.

The present invention relates to an optically pure (+) or (−) enantiomer of a ruthenium complex having the following formula (1-2):

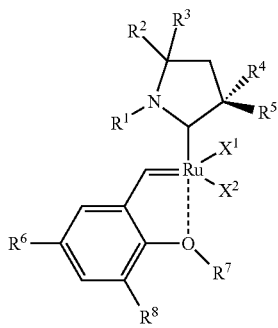

(I-2)

wherein:
- R¹ is a $(C_6\text{-}C_{14})$aryl group, a $(C_1\text{-}C_6)$alkyl group or a $(C_8\text{-}C_{20})$cycloalkyl group, said aryl group being optionally substituted with at least one substituent chosen from the group consisting of: halogen, $(C_6\text{-}C_{10})$aryl group, and $(C_1\text{-}C_6)$alkyl group, said alkyl group being optionally substituted with one or several phenyl group(s);
- R² is H, a $(C_6\text{-}C_{10})$aryl group or a $(C_1\text{-}C_6)$alkyl group;
- R³ is a $(C_1\text{-}C_6)$alkyl group; or R² and R³ may together form, with the carbon atom carrying them, a $(C_3\text{-}C_6)$cycloalkyl;
- R⁴ is selected from the following groups: $(C_6\text{-}C_{20})$aryl, $(C_6\text{-}C_{10})$alkyl, and $(C_3\text{-}C_{12})$cycloalkyl group, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6\text{-}C_{10})$aryl, optionally substituted with one or several substituents, in particular selected in the group consisting of: $(C_1\text{-}C_6)$alkylamino, di$(C_1\text{-}C_6)$alkylamino, $(C_1\text{-}C_6)$alcoxy, and $(C_1\text{-}C_6)$alkyl;
- R⁵ is selected from the following groups: $(C_6\text{-}C_{20})$aryl, $(C_6\text{-}C_{10})$alkyl, $(C_3\text{-}C_{12})$cycloalkyl, heteroaryl, $(C_6\text{-}C_{10})$aryl$(C_1\text{-}C_6)$alkyl, and heteroaryl$(C_1\text{-}C_6)$alkyl, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6\text{-}C_{10})$aryl, optionally substituted with one or several substituents, in particular selected in the group consisting of: $(C_1\text{-}C_6)$alkylamino, di$(C_1\text{-}C_6)$alkylamino, $(C_1\text{-}C_6)$alcoxy, and $(C_1\text{-}C_6)$alkyl;
with the proviso that R⁵ is different from R⁴;
- X¹ is an halogen atom, a $(C_1\text{-}C_6)$alkoxy group or a —S—$(C_6\text{-}C_{10})$aryl group;
- X² is an halogen atom or a $(C_1\text{-}C_6)$alkoxy group;
- or X¹ and X² may form together with the ruthenium atom carrying them a heterocycloalkyl group fused with a phenyl group, said phenyl group being possibly substituted with at least one halogen atom,
- R⁶ is H or is selected from the following groups: nitro, cyano, $(C_1\text{-}C_6)$alkyl, cycloalkyl, $(C_1\text{-}C_6)$alkoxy, cycloalkyloxy, $(C_6\text{-}C_{10})$aryl, heteroaryl, $(C_6\text{-}C_{10})$aryloxy, heteroaryloxy, $(C_1\text{-}C_6)$alkylcarbonyl, arylcarbonyl, $(C_1\text{-}C_6)$alkoxycarbonyl, aryloxycarbonyl, carboxyl, amido, $(C_1\text{-}C_6)$alkylsulfonyl, arylsulfonyl, $(C_1\text{-}C_6)$alkylsulfinyl, arylsulfinyl, $(C_1\text{-}C_6)$alkylthio, arylthio, sulfonamide, halogen, —NR$_a$R$_b$, —SO$_2$—NRR', and —N(R$_c$)—C(=O)—R$_c$, R$_a$ and R$_b$ being independently selected from H and $(C_1\text{-}C_6)$alkyl, R and R' being selected from the following groups: $(C_1\text{-}C_6)$alkyl, $(C_6\text{-}C_{10})$aryl, heteroaryl, and halo$(C_1\text{-}C_6)$alkyl, R$_c$ being H or being selected from the following groups: $(C_1\text{-}C_6)$alkyl, $(C_6\text{-}C_{10})$aryl, and heteroaryl, R$_d$ being H or selected from the following groups: $(C_1\text{-}C_6)$alkyl, halo$(C_1\text{-}C_6)$alkyl, cycloalkyl, $(C_6\text{-}C_{10})$aryl, heteroaryl, $(C_1\text{-}C_6)$alkoxy, cycloalkyloxy, $(C_6\text{-}C_{10})$aryloxy, and heteroaryloxy;

R⁷ is a $(C_1\text{-}C_6)$alkyl group; and

R⁸ is H, a $(C_6\text{-}C_{10})$aryl group or a $(C_1\text{-}C_6)$alkyl group.

The present invention also relates to an optically pure (+) or (−) enantiomer of a ruthenium complex, having the following formula (II-1):

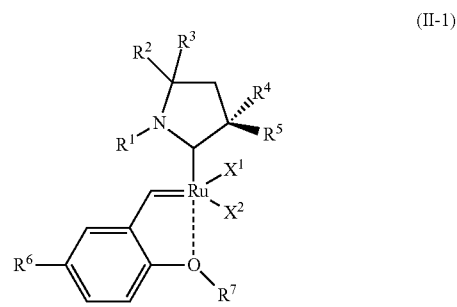

(II-1)

wherein:
- X¹ is an halogen atom, a $(C_1\text{-}C_6)$alkoxy group or a —S—$(C_6\text{-}C_{10})$aryl group;
- X² is an halogen atom or a $(C_1\text{-}C_6)$alkoxy group;
- or X¹ and X² may form together with the ruthenium atom carrying them a heterocycloalkyl group fused with a phenyl group, said phenyl group being possibly substituted with at least one halogen atom,
- R¹ is a $(C_6\text{-}C_{14})$aryl group, a $(C_1\text{-}C_6)$alkyl group or a $(C_8\text{-}C_{20})$cycloalkyl group, said aryl group being optionally substituted with at least one substituent chosen from the group consisting of: halogen, $(C_6\text{-}C_{10})$aryl group, and $(C_1\text{-}C_6)$alkyl group, said alkyl group being optionally substituted with one or several phenyl group(s);
- R² is H, a $(C_6\text{-}C_{10})$aryl group or a $(C_1\text{-}C_6)$alkyl group;
- R³ is a $(C_1\text{-}C_6)$alkyl group; or R² and R³ may together form, with the carbon atom carrying them, a $(C_3\text{-}C_6)$cycloalkyl;
- R⁴ is selected from the following groups: $(C_6\text{-}C_{20})$aryl, $(C_6\text{-}C_{10})$alkyl, and $(C_3\text{-}C_{12})$cycloalkyl group, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6\text{-}C_{10})$aryl, optionally substituted with one or several substituents, in particular selected in the group consisting of: $(C_1\text{-}C_6)$alkylamino, di$(C_1\text{-}C_6)$alkylamino, $(C_1\text{-}C_6)$alcoxy, and $(C_1\text{-}C_6)$alkyl;
- R⁵ is selected from the following groups: $(C_6\text{-}C_{20})$aryl, $(C_6\text{-}C_{10})$alkyl, $(C_3\text{-}C_{12})$cycloalkyl, heteroaryl, $(C_6\text{-}C_{10})$aryl$(C_1\text{-}C_6)$alkyl, and heteroaryl$(C_1\text{-}C_6)$alkyl, said aryl group being optionally substituted with at least one substituent chosen from the group consisting of: $(C_1\text{-}C_6)$alkyl, optionally substituted with one or several phenyl group(s), $(C_6\text{-}C_{10})$aryl$(C_1\text{-}C_6)$alkyl, and $(C_6$-

$C_{10}$)aryl, optionally substituted with one or several substituents, in particular selected in the group consisting of: $(C_1$-$C_6)$alkylamino, di$(C_1$-$C_6)$alkylamino, $(C_1$-$C_6)$alcoxy, and $(C_1$-$C_6)$alkyl;

with the proviso that $R^5$ is different from $R^4$:

$R^6$ is H or is selected from the following groups: nitro, cyano, $(C_1$-$C_6)$alkyl, cycloalkyl, $(C_1$-$C_6)$alkoxy, cycloalkyloxy, $(C_6$-$C_{10})$aryl, heteroaryl, $(C_6$-$C_{10})$aryloxy, heteroaryloxy, $(C_1$-$C_6)$alkylcarbonyl, arylcarbonyl, $(C_1$-$C_6)$alkoxycarbonyl, aryloxycarbonyl, carboxyl, amido, $(C_1$-$C_6)$alkylsulfonyl, arylsulfonyl, $(C_1$-$C_6)$alkylsulfinyl, arylsulfinyl, $(C_1$-$C_6)$alkylthio, arylthio, sulfonamide, halogen, —$NR_aR_b$, —$SO_2$—NRR', and —$N(R_e)$—$C(=O)$—$R_C$, $R_a$ and $R_b$ being independently selected from H and $(C_1$-$C_6)$alkyl, R and R' being selected from the following groups: $(C_1$-$C_6)$alkyl, $(C_6$-$C_{10})$aryl, heteroaryl, and halo$(C_1$-$C_6)$alkyl, $R_c$ being H or being selected from the following groups: $(C_1$-$C_6)$alkyl, $(C_6$-$C_{10})$aryl, and heteroaryl, $R_d$ being H or selected from the following groups: $(C_1$-$C_6)$alkyl, halo$(C_1$-$C_6)$alkyl, cycloalkyl, $(C_6$-$C_{10})$aryl, heteroaryl, $(C_1$-$C_6)$alkoxy, cycloalkyloxy, $(C_6$-$C_{10})$aryloxy, and heteroaryloxy; and $R^7$ is a $(C_1$-$C_6)$alkyl group.

According to an embodiment, in formulae (I), (I-1), (I-2), and (II-1), $R^1$ is an alkyl group as defined above.

According to an embodiment, in formulae (I), (I-1), (I-2), and (II-1), $R^1$ is a substituted phenyl group. Preferably, in formulae (I), (I-1), (I-2), and (II-1), $R^1$ is a phenyl group being substituted with at least one or two substituent(s), said substituents being selected from the group consisting of: $(C_1$-$C_6)$alkyl groups, such as methyl, ethyl or isopropyl, halogen such as F, and —CH(Ar)$_2$, such as —CH(Ph)$_2$, Ar being an aryl group.

Preferably, in formulae (I), (I-1), (I-2), and (II-1), $R^1$ is a phenyl group being substituted with two substituent(s) in ortho position, said substituents being identical or different.

As preferred $R^1$ groups, the followings may be mentioned:

phenyl groups with two alkyl groups, in particular two identical alkyl groups, such as ethyl or isopropyl, in ortho position;

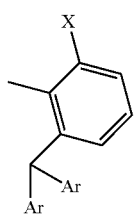

wherein Ar is an aryl group as defined above, and preferably a phenyl group, and X is a halogen, preferably being Cl, Br or F;

or

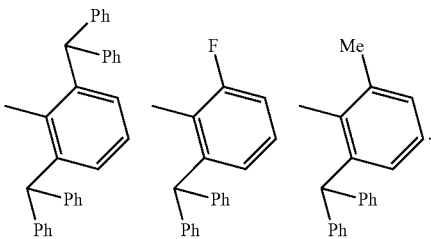

According to an embodiment, in formulae (I), (I-1), (I-2), and (II-1), $R^4$ is an alkyl group as defined above, preferably a methyl group, and $R^5$ is an aryl group as defined above. Preferably, said aryl group is an anthracenyl radical or a $(C_6$-$C_{10})$aryl group, such as a phenyl group, being substituted with at least one, in particular one, two or three, substituent(s), said substituent(s) being selected from the group consisting of: $(C_1$-$C_6)$alkyl groups, such as methyl or isopropyl, $(C_1$-$C_6)$alkylamino groups, di$(C_1$-$C_6)$alkylamino groups, $(C_1$-$C_6)$alcoxy groups, $(C_6$-$C_{10})$aryl groups such as phenyl, and —CH(Ar)$_2$, such as —CH(Ph)$_2$, Ar being an aryl group. Preferably, $R^5$ is a phenyl group being substituted with two substituent(s) in meta position, said substituents being identical or different, preferably identical.

According to an embodiment, in formulae (I), (I-1), (I-2), and (II-1), $R^4$ is an aryl group as defined above and $R_5$ is an alkyl group as defined above, preferably a methyl group. Preferably, said aryl group is an anthracenyl radical or a $(C_6$-$C_{10})$aryl group, such as a phenyl group, being substituted with at least one, in particular one, two or three, substituent(s), said substituent(s) being selected from the group consisting of: $(C_1$-$C_6)$alkyl groups, such as methyl or isopropyl, $(C_1$-$C_6)$alkylamino groups, di$(C_1$-$C_6)$alkylamino groups, $(C_1$-$C_6)$alcoxy groups, $(C_6$-$C_{10})$aryl groups such as phenyl, and —CH(Ar)$_2$, such as —CH(Ph)$_2$, Ar being an aryl group. Preferably, $R^4$ is a phenyl group being substituted with two substituent(s) in meta position, said substituents being identical or different, preferably identical.

As preferred aryl groups for $R^4$ (or $R^5$), the followings may be mentioned:

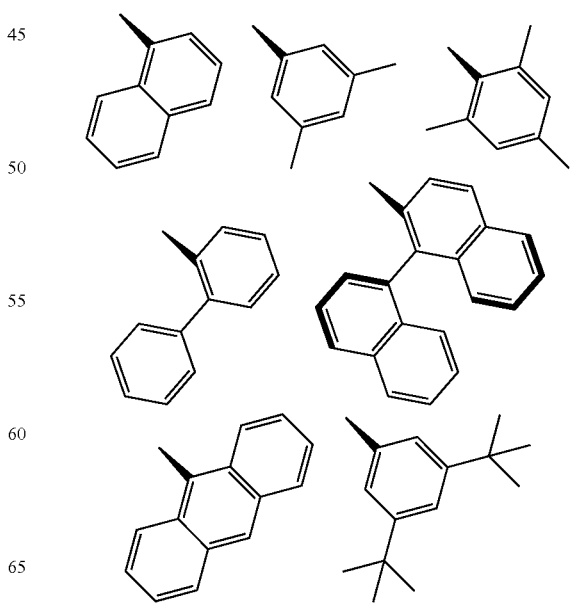

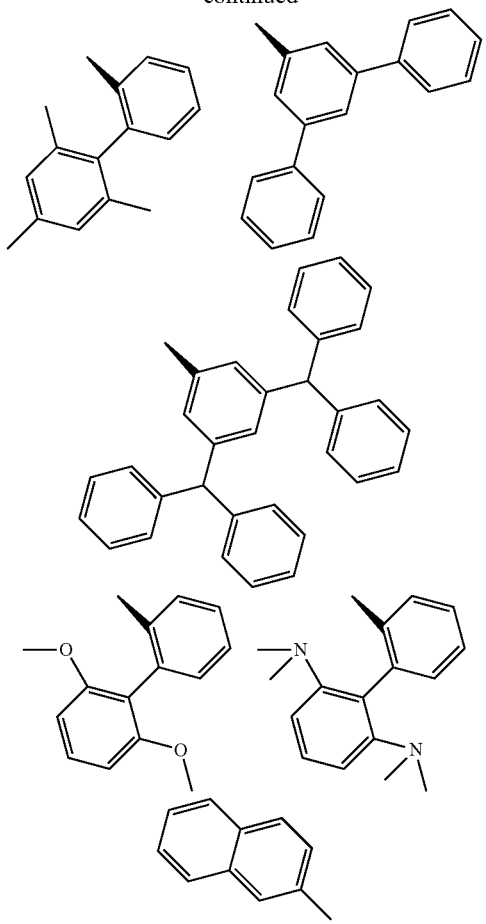

According to an embodiment, in formulae (I), (I-1), (I-2), and (II-1), $R^4$ is an aryl group as defined above, said aryl group being optionally substituted with at least one substituent as defined hereafter, and $R^5$ is an alkyl group as defined above, preferably a methyl group.

According to an embodiment, in formulae (I), (I-1), (I-2), and (II-1), $R^5$ is an aryl group as defined above, said aryl group being optionally substituted with at least one substituent as defined hereafter, and $R^4$ is an alkyl group as defined above, preferably a methyl group.

According to an embodiment, in formulae (I), (I-1), (I-2), and (II-1), $R^5$ is a $(C_6-C_{10})aryl(C_1-C_6)alkyl$ group as defined above, said aryl group being optionally substituted with at least one substituent as defined hereafter, and $R^4$ is an alkyl group as defined above, preferably a methyl group.

According to an embodiment, in formulae (I), (I-1), (I-2), and (II-1), $R^5$ is a benzyl group, optionally substituted with at least one substituent as defined hereafter, such as an isopropyl group, and $R^4$ is an alkyl group as defined above, preferably a methyl group.

According to an embodiment, in formulae (I), (I-1), (I-2), and (II-1), $R^4$ is an alkyl group as defined above, preferably a methyl group, and $R^5$ is selected from the group consisting of: $(C_1-C_{10})alkyl$, such as tertio-butyl group, and $(C_3-C_{12})$ cycloalkyl groups.

According to an embodiment, in formulae (I), (I-1), (I-2), and (II-1), $R^5$ is an alkyl group as defined above, preferably a methyl group, and $R^4$ is selected from the group consisting of: $(C_1-C_{10})alkyl$, such as tertio-butyl group, and $(C_3-C_{12})$ cycloalkyl groups.

As preferred cycloakyl groups for $R^4$ (or $R^5$), the followings may be mentioned:

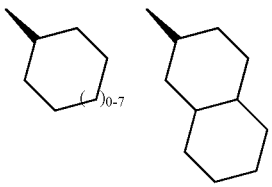

or adamantyl.

The present invention also relates to an optically pure (+) or (−) enantiomer of a ruthenium complex, having the following formula (II):

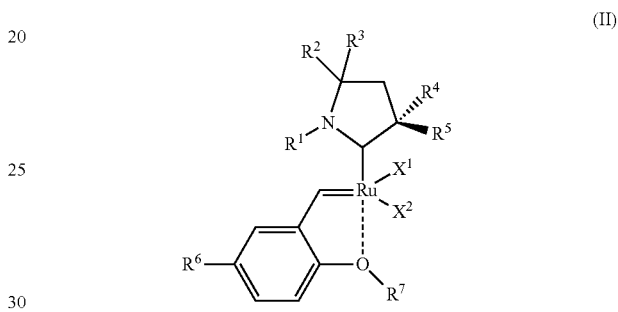

wherein:
$X^1$ is an halogen atom or a $(C_1-C_6)alkoxy$ group;
$X^2$ is an halogen atom or a $(C_1-C_6)alkoxy$ group;
$R^1$ is a $(C_6-C_{10})aryl$ group or a $(C_1-C_6)alkyl$ group, said aryl group being optionally substituted with at least one substituent chosen from the $(C_1-C_6)alkyl$ groups;
$R^2$ is a $(C_6-C_{10})aryl$ group or a $(C_1-C_6)alkyl$ group;
$R^3$ is a $(C_1-C_6)alkyl$ group;
$R^4$ is a $(C_6-C_{10})aryl$ group, a $(C_1-C_6)alkyl$ group or a $(C_3-C_6)cycloalkyl$ group, said aryl group being optionally substituted with at least one substituent chosen from the $(C_1-C_6)alkyl$ groups;
$R^5$ is selected from the following groups: $(C_6-C_{10})aryl$, $(C_1-C_6)alkyl$, $(C_3-C_6)cycloalkyl$, heteroaryl, $(C_6-C_{10})aryl(C_1-C_6)alkyl$, and heteroaryl$(C_1-C_6)alkyl$, said aryl group being optionally substituted with at least one substituent chosen from the $(C_1-C_6)alkyl$ groups;
with the proviso that $R^5$ is different from $R^4$;
$R^6$ is H, nitro or a $(C_1-C_6)alkyl$ group; and
$R^7$ is a $(C_1-C_6)alkyl$ group.

In the context of the present invention, the expression "$C_t-C_z$" means a carbon-based chain which can have from t to z carbon atoms, for example $C_1-C_3$ means a carbon-based chain which can have from 1 to 3 carbon atoms.

According to the invention, the term "halogen" means: a fluorine, a chlorine, a bromine or an iodine.

According to the invention, the term "alkyl group" means: a linear or branched, saturated, hydrocarbon-based aliphatic group comprising, unless otherwise mentioned, from 1 to 12 carbon atoms. By way of examples, mention may be made of methyl, ethyl, n-propyl, isopropyl, butyl, isobutyl, tert-butyl or pentyl groups; According to the invention, the term "cycloalkyl group" means: a cyclic carbon-based group comprising, unless otherwise mentioned, from 3 to 12 carbon atoms.

By way of examples, mention may be made of cyclopropyl, cyclobutyl, cyclopentyl, cyclohexyl, or adamantyl etc. groups; According to the invention, the term "haloalkyl group" means: an alkyl group as defined above, in which one or more of the hydrogen atoms is (are) replaced with a halogen atom. By way of example, mention may be made of fluoroalkyls, in particular $CF_3$ or $CHF_2$.

According to the invention, the term "alkoxy group" means: an —O-alkyl radical where the alkyl group is as previously defined. By way of examples, mention may be made of —O—($C_1$-$C_4$)alkyl groups, and in particular the —O-methyl group, the —O-ethyl group as —O—$C_3$alkyl group, the —O-propyl group, the —O-isopropyl group, and as —O—$C_4$alkyl group, the —O-butyl, —O-isobutyl or —O-tert-butyl group.

According to the invention, the term "aryl group" means: a cyclic aromatic group comprising between 6 and 10 carbon atoms. By way of examples of aryl groups, mention may be made of phenyl or naphthyl groups.

According to the invention, the term "heteroaryl" means: a 5- to 10-membered aromatic monocyclic or bicyclic group containing from 1 to 4 heteroatoms selected from O, S or N. By way of examples, mention may be made of imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinolinyl and isoquinolinyl groups.

By way of a heteroaryl comprising 5 to 6 atoms, including 1 to 4 nitrogen atoms, mention may in particular be made of the following representative groups: pyrrolyl, pyrazolyl, 1,2,3-triazolyl, 1,2,4-triazolyl, tetrazolyl and 1,2,3-triazinyl.

Mention may also be made, by way of heteroaryl, of thiophenyl, oxazolyl, furazanyl, 1,2,4-thiadiazolyl, naphthyridinyl, quinoxalinyl, phthalazinyl, imidazo[1,2-a]pyridine, imidazo[2,1-b]thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindole, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, and also the corresponding groups resulting from their fusion or from fusion with the phenyl nucleus.

According to the invention, the term "heterocycloalkyl" means: a 4- to 10-membered, saturated or partially unsaturated, monocyclic or bicyclic group comprising from one to three heteroatoms selected from O, S or N; the heterocycloalkyl group may be attached to the rest of the molecule via a carbon atom or via a heteroatom; the term bicyclic heterocycloalkyl includes fused bicycles and spiro-type rings.

By way of saturated heterocycloalkyl comprising from 5 to 6 atoms, mention may be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridinyl, dioxanyl, morpholinyl, piperidinyl, piperazinyl, tetrahydrothiopyranyl, dithianyl, thiomorpholinyl or isoxazolidinyl.

When the heterocycloalkyl is substituted, the substitution(s) may be on one (or more) carbon atom(s) and/or on the heteroatom(s). When the heterocycloalkyl comprises several substituents, they may be borne by one and the same atom or different atoms.

The abovementioned "alkyl", "cycloalkyl", "aryl", "heteroaryl" and "heterocycloalkyl" radicals can be substituted with one or more substituents. Among these substituents, mention may be made of the following groups: amino, hydroxyl, thiol, oxo, halogen, alkyl, alkoxy, alkylthio, alkylamino, aryloxy, arylalkoxy, cyano, trifluoromethyl, carboxy or carboxyalkyl.

According to the invention, the term "alkylthio" means: an —S-alkyl group, the alkyl group being as defined above.

According to the invention, the term "arylthio" means: an —S-aryl group, the aryl group being as defined above.

According to the invention, the term "alkylamino" means: an —NH-alkyl group, the alkyl group being as defined above.

According to the invention, the term "cycloalkyloxy" means: an —O-cycloalkyl group, the cycloalkyl group being as defined above.

According to the invention, the term "aryloxy" means: an —O-aryl group, the aryl group being as defined above.

According to the invention, the term "(hetero)arylalkoxy" means: a (hetero)aryl-alkoxy- group, the (hetero)aryl and alkoxy groups being as defined above.

According to the invention, the term "alkylcarbonyl" means a —CO-alkyl group, the alkyl group being as defined above.

According to the invention, the term "alkoxylcarbonyl" means a —CO—O-alkyl group, the alkyl group being as defined above.

According to the invention, the term "arylcarbonyl" means a —CO-aryl group, the aryl group being as defined above.

According to the invention, the term "aryloxycarbonyl" means a —CO-aryloxy group, the aryloxy group being as defined above.

According to the invention, the term "alkylsulfonyl" means a —$SO_2$-alkyl group, the alkyl group being as defined above.

According to the invention, the term "arylsulfonyl" means a —$SO_2$-aryl group, the aryl group being as defined above.

According to the invention, the term "alkylsulfinyl" means a —SO-alkyl group, the alkyl group being as defined above.

According to the invention, the term "arylsulfinyl" means a —SO-aryl group, the aryl group being as defined above.

According to the invention, the term "carboxyalkyl" means: an HOOC-alkyl-group, the alkyl group being as defined above. As examples of carboxyalkyl groups, mention may in particular be made of carboxymethyl or carboxyethyl.

According to the invention, the term "carboxyl" means: a COOH group.

According to the invention, the term "oxo" means: "=O".

When an alkyl radical is substituted with an aryl group, the term "arylalkyl" or "aralkyl" radical is used. The "arylalkyl" or "aralkyl" radicals are aryl-alkyl- radicals, the aryl and alkyl groups being as defined above. Among the arylalkyl radicals, mention may in particular be made of the benzyl or phenethyl radicals.

According to an embodiment, in formula (II), $X_1$ and $X_2$ are halogen atoms, preferably Cl or I.

According to an embodiment, in formula (II), $R^1$ is a ($C_6$-$C_{10}$)aryl group substituted with at least one substituent chosen from the group consisting of ($C_1$-$C_6$)alkyl, preferably a phenyl group substituted with two alkyl groups, such as isopropyl or ethyl groups.

According to an embodiment, in formula (II), $R^2$ is a ($C_1$-$C_6$)alkyl group.

According to an embodiment, in formula (II), $R^2$ is a ($C_6$-$C_{10}$)aryl group, preferably a phenyl group.

According to an embodiment, in formula (II), $R^2$ and $R^3$ are identical, and are preferably a methyl group.

According to an embodiment, in formula (II), $R^4$ and $R^5$ are different and are selected from the following groups: $(C_6-C_{10})$aryl such as phenyl or naphthyl, $(C_1-C_6)$alkyl such as methyl, and $(C_3-C_6)$cycloalkyl such as cyclohexyl, said aryl group being optionally substituted with two substituents selected from the $(C_1-C_6)$alkyl groups.

According to an embodiment, in formula (II), $R^5$ is a $(C_6-C_{10})$aryl$(C_1-C_6)$alkyl group as defined above, said aryl group being optionally substituted with at least one substituent as defined hereafter, and $R^4$ is an alkyl group as defined above, preferably a methyl group.

According to an embodiment, in formula (II), $R^5$ is a benzyl group, optionally substituted with at least one substituent as defined hereafter, such as an isopropyl group, and $R^4$ is an alkyl group as defined above, preferably a methyl group.

According to an embodiment, in formula (II), $R^6$ is H or nitro.

The present invention also relates to an optically pure (+) or (−) enantiomer as defined above, having one of the following formulae:

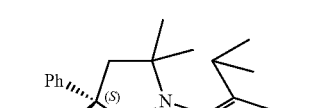

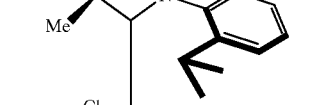

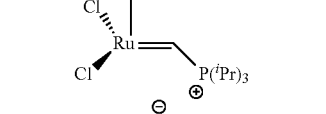

(+)-(R)-Ru-1a

-continued

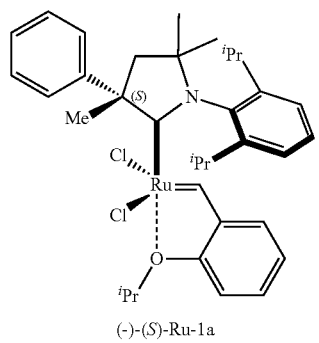

(−)-(S)-Ru-1a

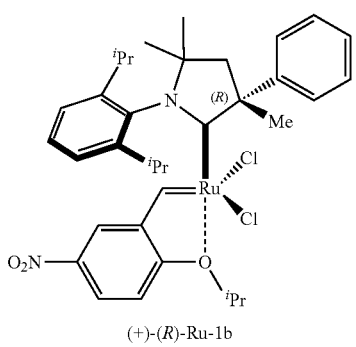

(+)-(R)-Ru-1b

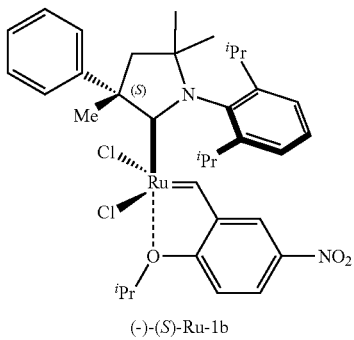

(−)-(S)-Ru-1b

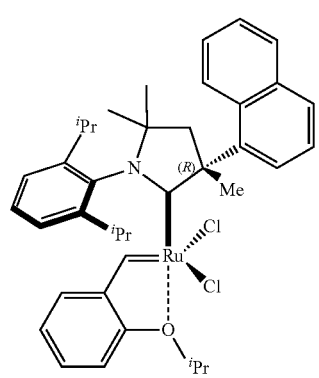

(−)-(R)-Ru-2a

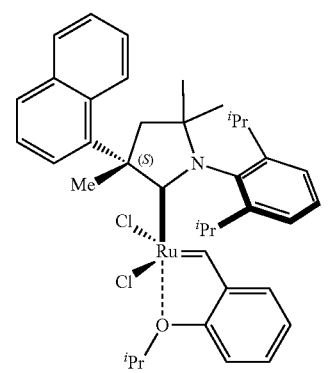
(+)-(S)-Ru-2a
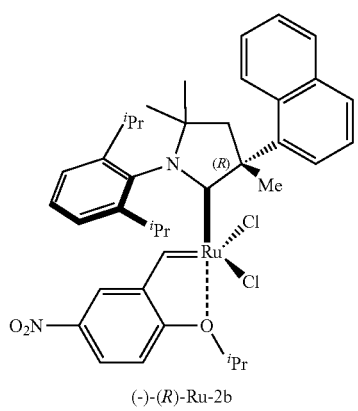
(−)-(R)-Ru-2b
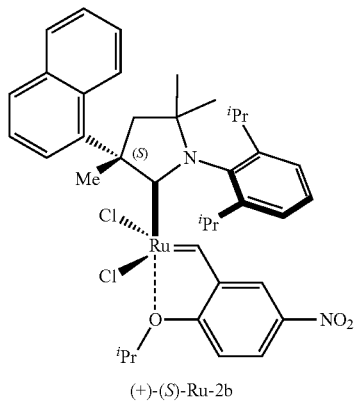
(+)-(S)-Ru-2b
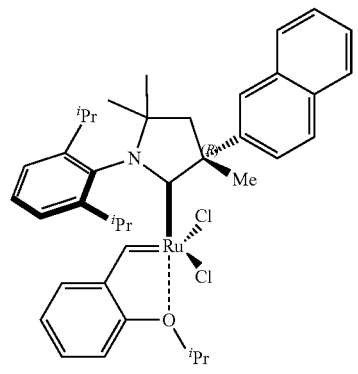
(−)-(R)-Ru-3a
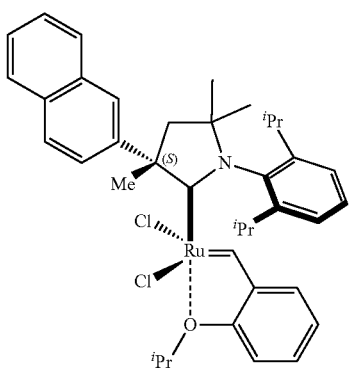
(+)-(S)-Ru-3a
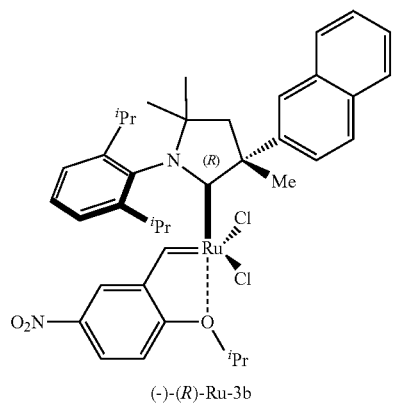
(−)-(R)-Ru-3b
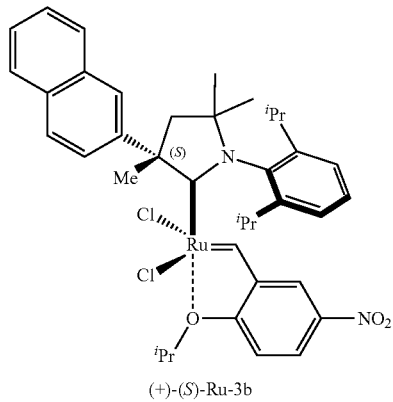
(+)-(S)-Ru-3b
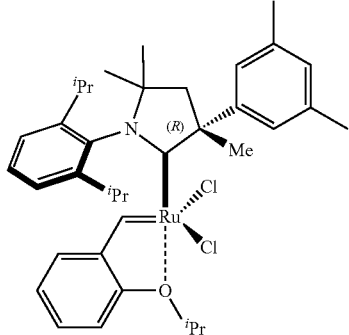
(+)-(R)-Ru-4a -continued
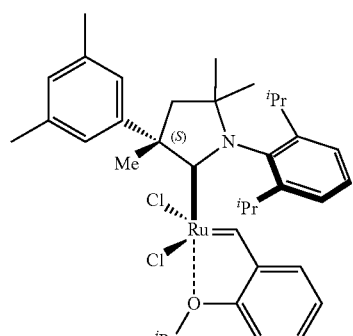
(−)-(S)-Ru-4a
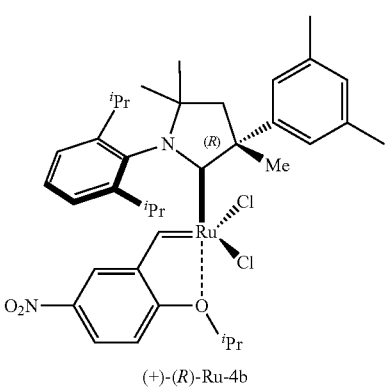
(+)-(R)-Ru-4b
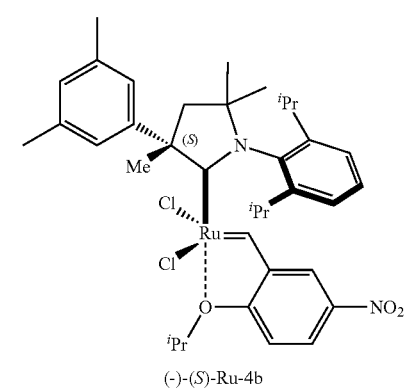
(−)-(S)-Ru-4b
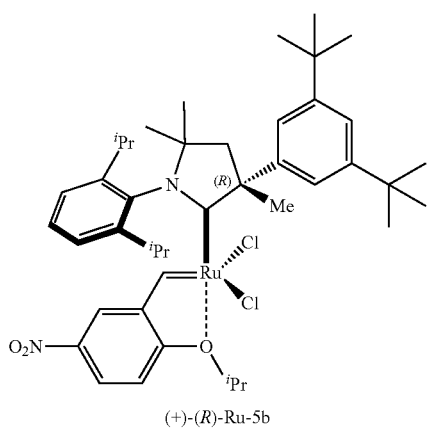
(+)-(R)-Ru-5b
-continued
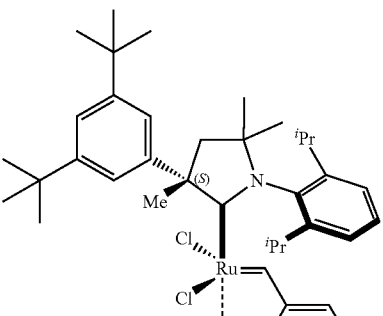
(−)-(S)-Ru-5b
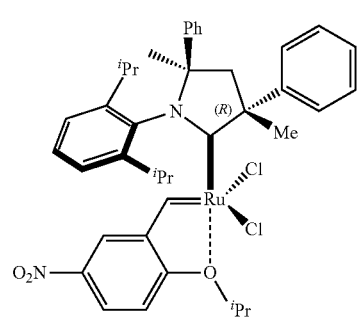
(+)-(R)-Ru-7b
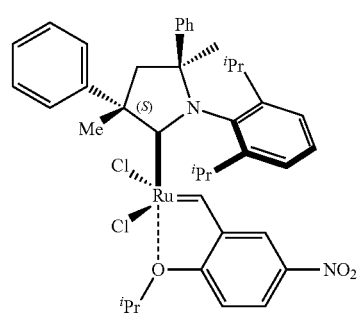
(−)-(S)-Ru-7b
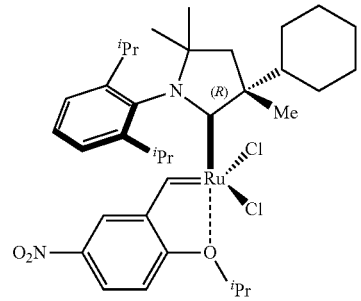
(+)-(R)-Ru-6b

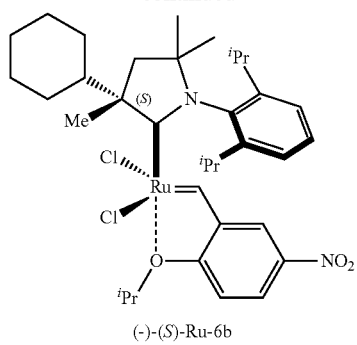
(-)-(S)-Ru-6b
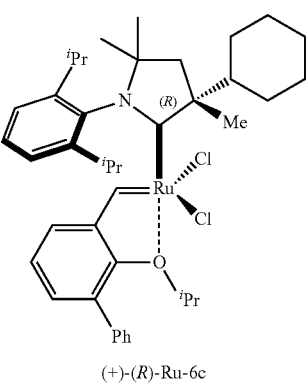
(+)-(R)-Ru-6c
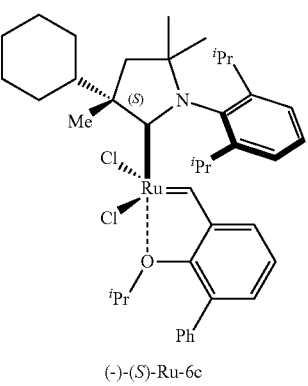
(-)-(S)-Ru-6c
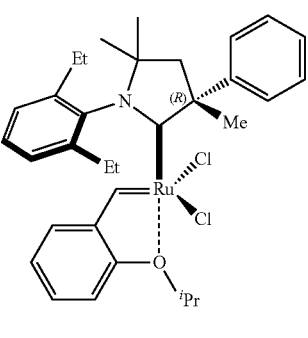
(+)-(R)-Ru-8a
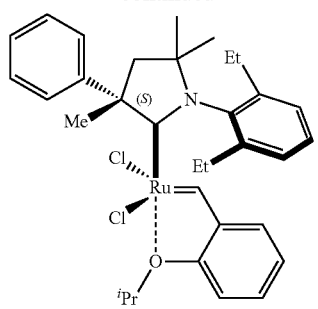
(-)-(S)-Ru-8a
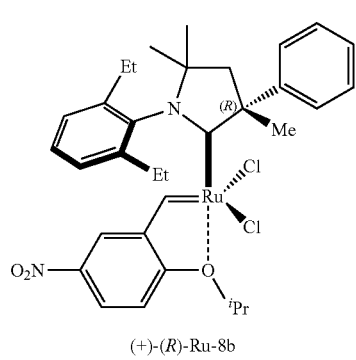
(+)-(R)-Ru-8b
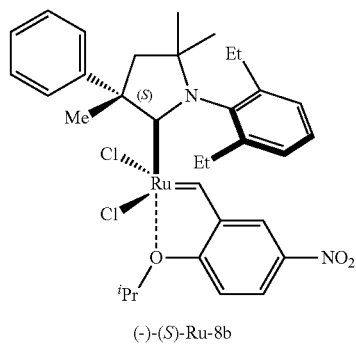
(-)-(S)-Ru-8b
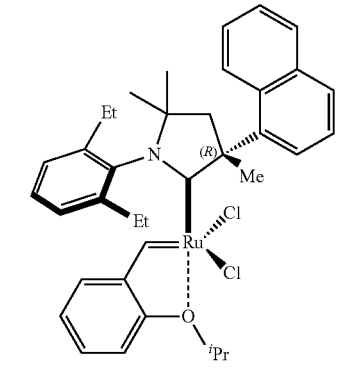
(+)-(S)-Ru-9a -continued
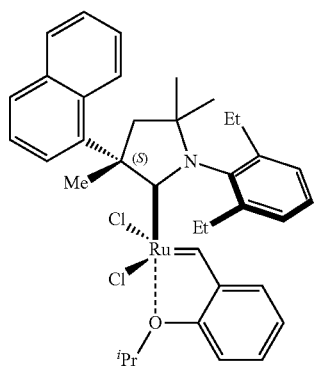
(−)-(S)-Ru-9a
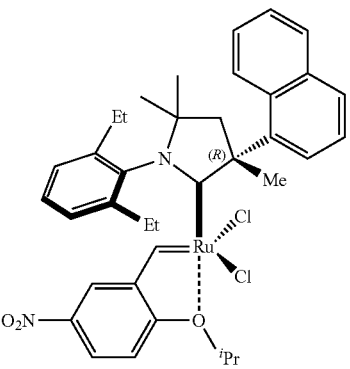
(+)-(R)-Ru-9b
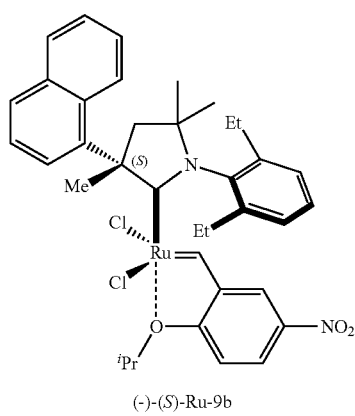
(−)-(S)-Ru-9b
-continued
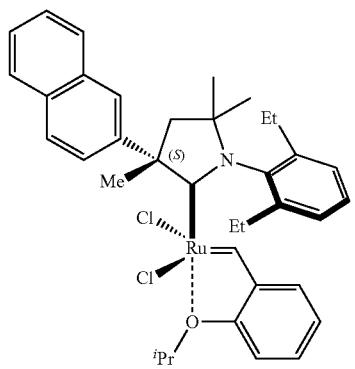
(−)-(R)-Ru-10a
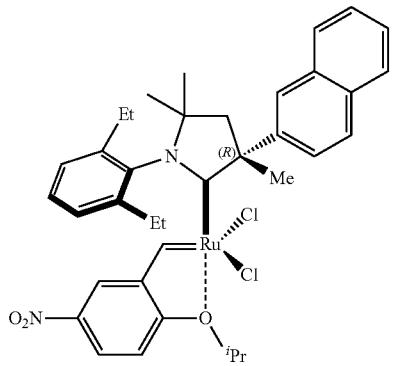
(+)-(R)-Ru-10b
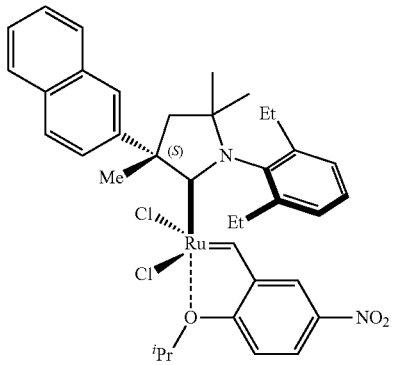
(−)-(S)-Ru-10b
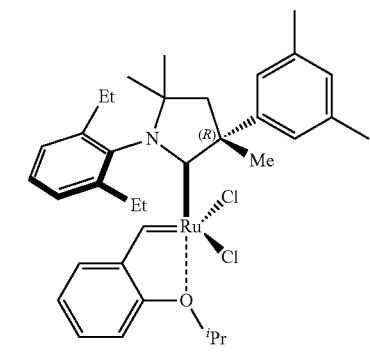
(+)-(R)-Ru-11a -continued
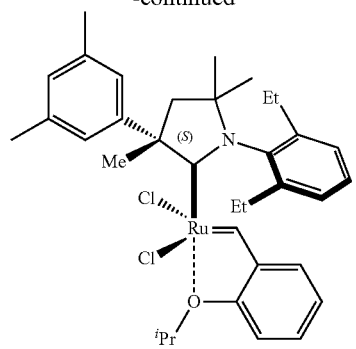
(−)-(S)-Ru-11a
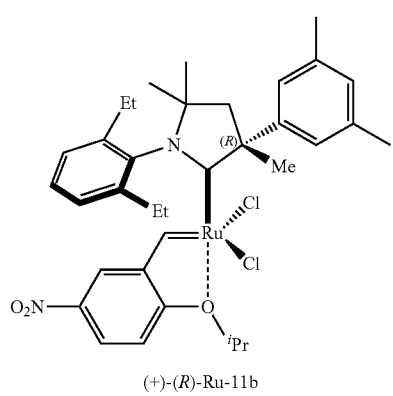
(+)-(R)-Ru-11b
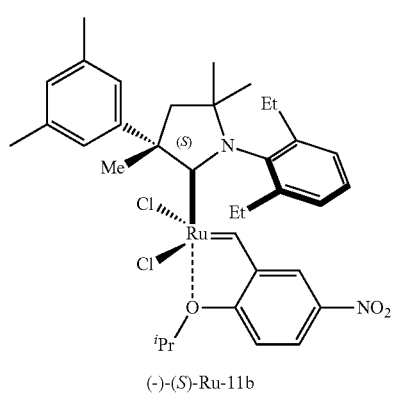
(−)-(S)-Ru-11b
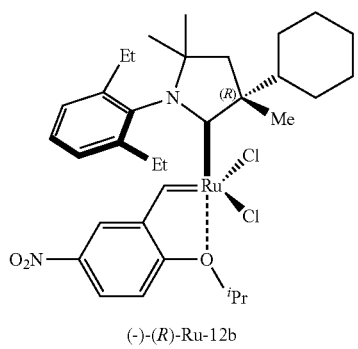
(−)-(R)-Ru-12b
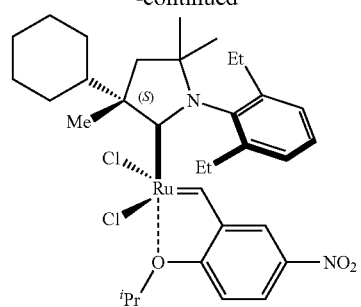
(+)-(S)-Ru-12b
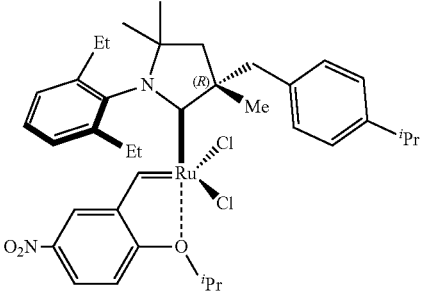
(−)-(R)-Ru-13b
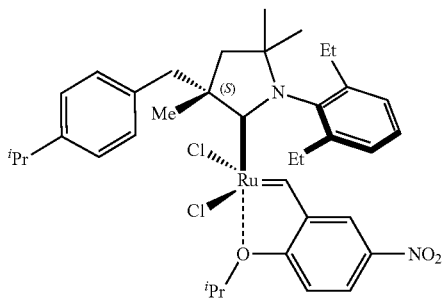
(+)-(S)-Ru-13b
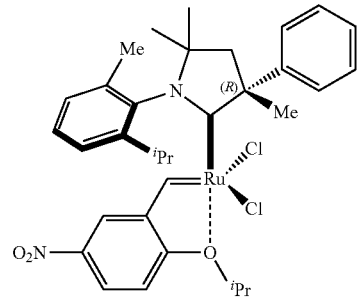
(−)-(R)-Ru-14b
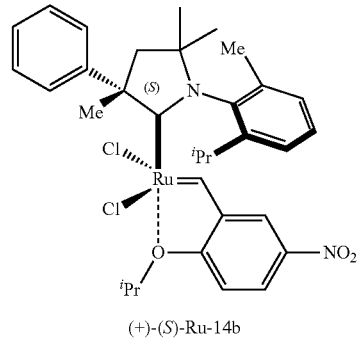
(+)-(S)-Ru-14b

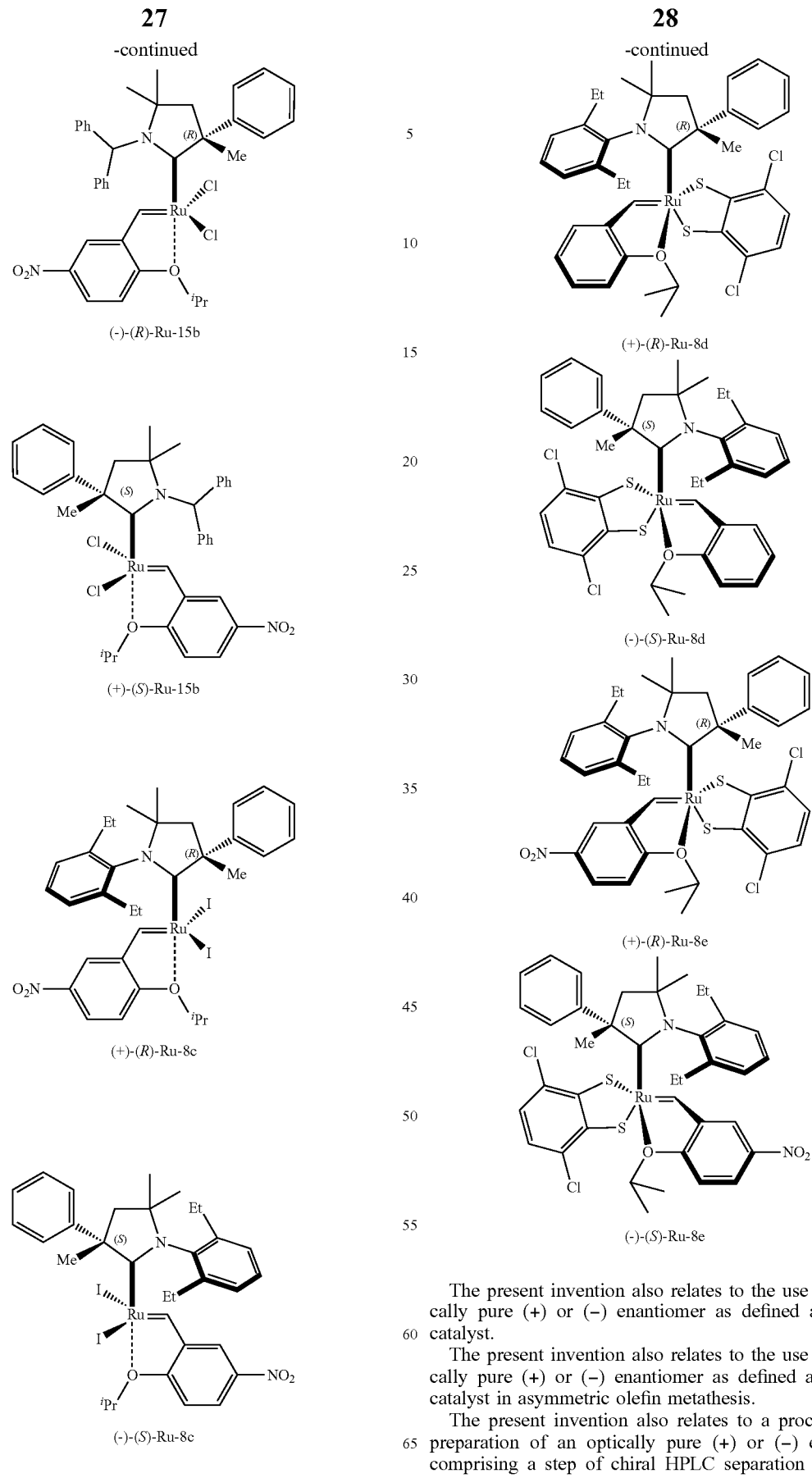

The present invention also relates to the use of an optically pure (+) or (−) enantiomer as defined above as a catalyst.

The present invention also relates to the use of an optically pure (+) or (−) enantiomer as defined above, as a catalyst in asymmetric olefin metathesis.

The present invention also relates to a process for the preparation of an optically pure (+) or (−) enantiomer, comprising a step of chiral HPLC separation of racemic ruthenium complexes of formula (I).

Preferably, said step of chiral HPLC separation is carried out with a HPLC column comprising amylose substituted with chloro-phenylcarbamate as chiral stationary phase.

EXAMPLES

Preparation of the Compounds of the Invention

General Information

All manipulations were carried out in an argon filled glovebox or using standard Schlenk techniques. Glassware was dried in an oven overnight at 150° C. or flame dried prior to use. Toluene and tetrahydrofuran, used for complex synthesis and catalysis, were purified using MBraun Solvent Purification Systems and freeze-pump-thaw degassed prior to use. Reactions were monitored by thin-layer chromatography (TLC) carried out on aluminium backed silica gel 60 (F254) plates from MERCK (grain-size distribution 60/20 µm); visualised using 254 nm UV light and $KMnO_4/K_2CO_3/$ NaOH in water for staining. Columns chromatography were performed with silica gel (spherical, particle size 40 µm, neutral) purchased from Sigma-Aldrich. The eluents employed are reported as volume (volume percentages).

NMR: For CAACs salts, NMR spectra were recorded on a Varian INOVA 500 MHz spectrometer. For Ru complexes and catalysis products, multinuclear NMR spectra were recorded on a Bruker ARX400 400 MHz spectrometer. For nucleus other than $^1H$ spectra were recorded with complete proton decoupling. Chemical shifts are reported in parts per million with the solvent resonance as the internal standard. Coupling constants (J) are reported in Hertz (Hz). Multiplicities in $^1H$ NMR are reported using following abbreviations: s=singlet, br s=broad singlet, d=doublet, dd=doublet of doublet, ddd=doublet of doublet of doublet, dt=doublet of triplet, t=triplet, q=quartet, quint=quintet, sept=septet, m=multiplet. When not specified, spectra were recorded at 298 K.

High Resolution Mass Spectrometry (HRMS): For CAACs salts, HRMS were performed at the UC San Diego Mass Spectrometry Laboratory on an Agilent 6230 Accurate-Mass TOFMS spectrometer using electrospray ionization. (ESI). For Ru complexes and catalysis products HRMS were recorded on a Waters QTof-I spectrometer using ESI.

Preparative chiral HPLC: $^{Prep}$HPLC Chiral separations were performed on an Agilent 1260 Infinity unit (pump G1311C, autosampler G1329B, DAD G1365D and fraction collector G1364C), monitored by Agilent OpenLAB CDS Chemstation LC at Aix Marseille University.

Optical rotations: Optical rotations for the complexes were measured at Aix Marseille University on a Jasco P-2000 polarimeter with a sodium lamp (589 nm), a halogen lamp (578, 546, 436, 405, 365 and 325 nm), in a 10 cm cell, thermostated at 25° C. with a Peltier controlled cell holder. Optical rotations for the catalysis products were measured at Institut des Sciences Chimiques de Rennes on a Jasco P-2000 polarimeter with a sodium lamp (589 nm), in a 1 cm cell, thermostated at 25° C. with a Peltier controlled cell holder.

Electronic Circular Dichroism (ECD) and UV: ECD and UV spectra were measured on a JASCO J-815 spectrometer equipped with a JASCO Peltier cell holder PTC-423 to maintain the temperature at 25.0±0.2° C. A CD quartz cell of 1 mm of optical path length was used. The CD spectrometer was purged with nitrogen before recording each spectrum, which was baseline subtracted. The baseline was always measured for the same solvent and in the same cell as the samples. Acquisition parameters: 0.1 nm as intervals, scanning speed 50 nm/min, band width 2 nm, and 3 accumulations per sample. The spectra are presented without smoothing and further data processing.

X-Ray crystallography: Intensity data were collected on a D8 VENTURE Bruker AXS diffractometer equipped with a (CMOS) PHOTON 100 detector using MoKα radiation (0.71073 Å) at T=150 K. Data reduction was performed using the SHELXT program. The structures were resolved using the software SHELXS-97 by the direct methods and refined using SHELXL-2013-4.

Enantiomeric Excess (Ee) Determination:
- GC analysis (Gas Chromatography): with a GC-2014 Shimadzu; Injector: 250° C.—Detector: 250° C.—FID; injection volume of 1 µL.
- SFC analysis (Supercritical Fluid Chromatography): using a Shimadzu Nexera UC SFC/UHPLC system (Shimadzu Corporation, Japan) consisting of two LC-30AD quaternary modifier pumps and LC-30ADSF $CO_2$ pump. The Sil-30AC autosampler was composed of a sample loop of 5 µL and three needle-rinsing ports. The modifier pumps and needle rinsing were degassed with three degassing units (DGU-5AR and DGU-3AR). Two CTO-20AC column ovens were used. An adapted SPD-M20A diode array detector (DAD) with high-pressure cell was employed for detection. The pressure into the chromatographic system was regulated by a SFC-30A backpressure regulator (BPR). The entire system was driven by CBM-20A as system controller. The monitoring interface was the LabSolutions software. Analyses were automatically performed with the Nexera Method Scouting software to generate a large number of SFC/UHPLC methods by combining columns and modifiers.

| Trade name | Chiral Stationary Phase | Seller* |
| --- | --- | --- |
| Chiralpak IA | Amylose tris(3,5-dimethyl-phenylcarbamate) immobilized on silica | CTE |
| Chiralpak IB | Cellulose tris(3,5-dimethylphenylcarbamate) immobilized on silica | CTE |
| Chiralpak IC | Cellulose tris(3,5-dichlorophenylcarbamate) immobilized on silica | CTE |
| Chiralpak ID | Amylose tris(3-chloro-phenylcarbamate) immobilized on silica | CTE |
| Chiralpak IE | Amylose tris(3,5-dichloro-phenylcarbamate) immobilized on silica | CTE |
| Chiralpak IF | Amylose tris(3-chloro-4-methylphenylcarbamate) immobilized on silica | CTE |
| Chiralpak IG | Amylose tris(3-chloro-5-methylphenylcarbamate) immobilized on silica | CTE |
| Chiralpak IH | Amylose tris[(S)alpha-phenethyl]-carbamate immobilized on silica | CTE |
| (S,S)-Ulmo | Silica bound N-(11-dimethylchloro-silyl)undecanoyl-N'-3,5-dinitrobenzoyl-(1S,2S)-diphenylethanediamine | Regis |
| (S,S)-Whelk-O1 | (3R,4S)-4-(3,5-Dinitrobenzamido)-3-[3-(dimethylsilyloxy)propyl]-1,2,3,4-tetrahydrophenanthrene | Regis |

*CTE: Chiral Technologies Europe (Illkirch, France); Regis: Regis Technologies (Morton Grove, USA)

HPLC analysis (High Performance Liquid Chromatography): using an Alliance e2695 Waters® HPLC with a UV/visible detector 2489 Waters®.

CAAC Salt Synthesis

General Procedure for the Synthesis of Aldimines

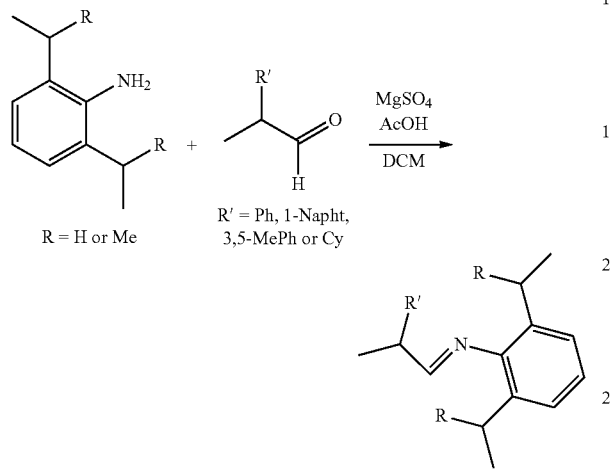

Amine (0.9 equiv) was added to a solution of aldehyde (1.0 equiv) in DCM. Then anhydrous $MgSO_4$ (2.0 equiv) and glacial acetic acid (catalytic amount) were added. The mixture was stirred overnight at rt and then filtered to remove $MgSO_4$. The crude alkenyl imine was obtained by evaporation of the solvent under vacuum.

General Procedure for the Synthesis of Alkenyl Imines

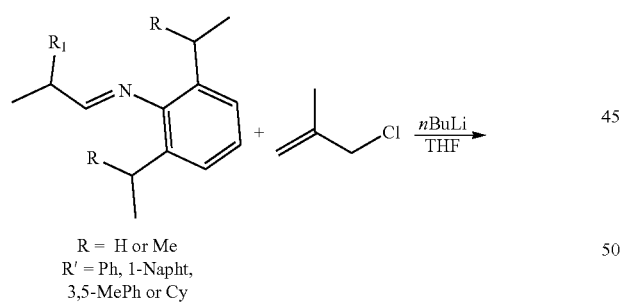

In a Schlenk under argon, a solution of aldimine (1.0 equiv) in THF was prepared. A solution of nBuLi (1.1 equiv) in hexanes was added dropwise to the solution at −78° C. After 15 min, the mixture was left to warm to rt and stirring was continued for an additional three hours. 3-Chloro-2-methylpropene (1.1 equiv) was then slowly added at −78° C. After 15 minutes the solution was warmed to rt and stirring was continued for an additional 12 hours. Removal of the volatiles under vacuum and extraction with pentane with filtration on celite afforded alkenyl aldimine as a light-yellow oil.

General Procedure for the Synthesis of Cyclic Iminium Salt

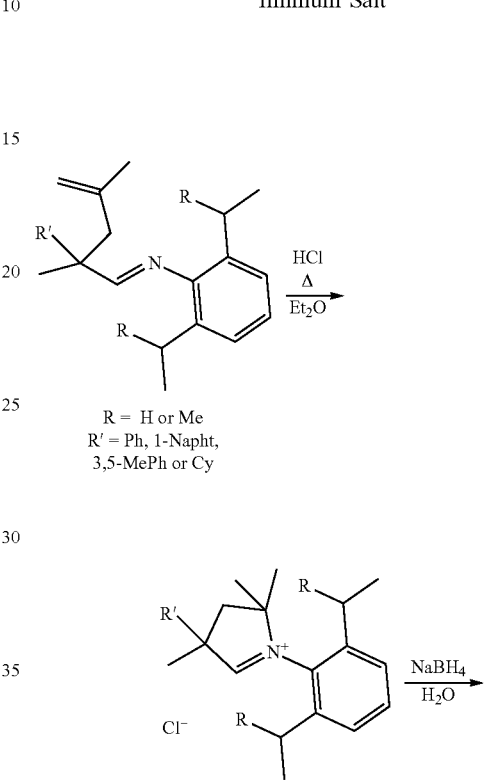

In a pressure Schlenk under argon, a solution of HCl 2.0 M in $Et_2O$ (1.2 equiv) was added dropwise to a solution of alkenyl aldimine (1.0 equiv) in a minimum of $Et_2O$ at 0° C. Precipitation of white powder was immediately observed. The solution was stirred at room temperature for 15 min, then at 90° C. overnight, and to finish at 50° C. for 1 day. Filtration at rt and washing of the precipitate with $Et_2O$ (×3) and pentane afforded cyclic iminium salt Cl⁻ as a white powder. This powder was dissolved in water and $NaBF_4$ (2.0 equiv) was added. Precipitation of white powder was immediately observed. The solution was stirred at rt overnight. Filtration and washing of the precipitate with $Et_2O$ (×3) and pentane afforded cyclic iminium salt $BF_4^-$.

CAACs Characterization

1-(2,6-diisopropylphenyl)-2,2,4-trimethyl-4-phenyl-3,4-dihydro-2H-pyrrol-1-ium tetrafluoroborate (CAAC-1)

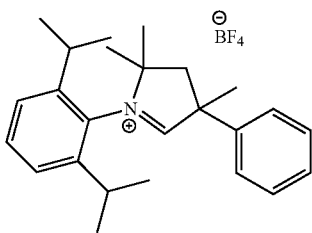

Chemical Formula: $C_{25}H_{34}BF_4N$
Molecular Weight: 435.36

CAAC-1 was prepared according to the 3-step procedure for CAAC synthesis with 2,6-diisopropylaniline (0.9 equiv) and 2-phenylpropanal (1 equiv). The desired product was obtained as a white powder (82% yield).

$^1$H NMR (500 MHz, CD$_3$CN): δ (ppm) 9.26 (s, 1H), 7.64 (t, J=7.5 Hz 1H), 7.55 (t, J=7.5 Hz, 2H), 7.52 (d, J=7.5 Hz, 1H), 7.48 (d, J=7.5 Hz, 2H), 7.45 (d, J=7.5 Hz, 2H), 3.10 (d, J=14.0 Hz, 1H), 2.82 (d, J=14.0 Hz, 1H), 2.79 (sept, J=7.0 Hz, 1H), 2.55 (sept, J=7.0 Hz, 1H), 1.93 (s, 3H), 1.58 (s, 3H), 1.40 (s, 3H), 1.39 (d, J=7.0 Hz, 3H), 1.25 (d, J=7.0 Hz, 3H), 1.15 (d, J=7.0 Hz, 3H), 1.08 (d, J=7.0 Hz, 3H).

$^{13}$C NMR (125 MHz, CD$_3$CN): δ (ppm) 189.8, 145.7, 145.4, 142.0, 133.2, 130.8, 130.0, 129.6, 126.7, 126.6, 126.6, 85.3, 55.7, 48.6, 29.9, 29.7, 27.2, 26.8, 26.8, 25.6, 25.5, 21.5, 21.4.

$^{11}$B NMR (128 MHz, CDCl$_3$): δ (ppm) −0.98.

$^{19}$F NMR (376 MHz, CDCl$_3$): δ (ppm) −151.0 (small), 151.1

HRMS for $C_{25}H_{34}N$ (M$^+$): calc.: 348.2686, found: 348.2680.

1-(2,6-diisopropylphenyl)-2,2,4-trimethyl-4-(naphthalen-1-yl)-3,4-di-hydro-2H-pyrrol-1-ium tetrafluoroborate (CAAC-2)

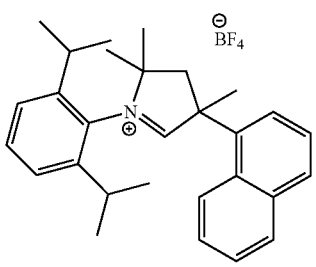

Chemical Formula: $C_{29}H_{36}BF_4N$
Molecular Weight: 485.42

CAAC-2 was prepared according to the 3-step procedure for CAAC synthesis with 2,6-diisopropylaniline (0.9 equiv) and 2-(naphthalen-1-yl)propanal (1 equiv). The desired product was obtained as a white powder (76% yield).

$^1$H NMR (500 MHz, CDCl$_3$): δ (ppm) 9.89 (s, 1H), 8.03 (d, J=8.0 Hz, 1H), 7.91 (d, J=8.0 Hz, 1H), 7.80 (d, J=8.0 Hz, 1H), 7.61 (t, J=7.5 Hz, 1H), 7.52-7.55 (m, 2H), 7.33-7.38 (m, 4H), 3.30 (d, J=14.0 Hz, 1H), 3.19 (d, J=14.0 Hz, 1H), 2.70 (sept, J=6.5 Hz, 1H), 2.69 (sept, J=6.5 Hz, 1H), 2.15 (s, 3H), 1.54 (s, 3H), 1.37 (d, J=6.5 Hz, 3H), 1.31 (d, J=6.5 Hz, 3H), 1.25 (s, 3H), 1.23 (d, J=6.5 Hz, 3H), 1.20 (d, J=6.5 Hz, 3H).

$^{13}$C NMR (125 MHz, CDCl$_3$): δ (ppm) 191.6, 145.3, 144.3, 138.3, 135.8, 132.6, 130.5, 130.1, 129.3, 129.3, 127.2, 126.6, 126.0, 126.0, 125.6, 124.8, 123.5, 84.0, 55.8, 50.0, 30.0, 29.4, 28.1, 26.9, 26.9, 25.9, 25.6, 22.3, 22.0.

$^{11}$B NMR (128 MHz, CDCl$_3$): δ (ppm) −0.91.

$^{19}$F NMR (376 MHz, CDCl$_3$): δ (ppm) −150.9 (small), 151.0.

HRMS for $C_{29}H_{36}N$ (M$^+$): calc.: 398.2842, found: 398.2839.

1-(2,6-diisopropylphenyl)-2,2,4-trimethyl-4-(naphthalen-2-yl)-3,4-di-hydro-2H-pyrrol-1-ium tetrafluoroborate (CAAC-3)

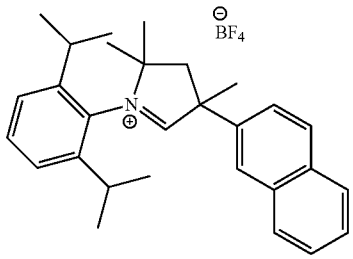

Chemical Formula: $C_{29}H_{36}BF_4N$
Molecular Weight: 485.42

CAAC-3 was prepared according to the 3-step procedure for CAAC synthesis with 2-(naphthalen-2-yl)propanal (1 equiv). The desired product was obtained as a white powder (52% yield).

$^1$H NMR (300 MHz, CD$_3$CN): δ (ppm) 9.72 (s, 1H), 8.06 (d, J=8.1 Hz, 1H), 7.89-7.97 (m, 3H), 7.58-7.66 (m, 4H), 7.51 (d, J=8.1 Hz, 1 HHz), 7.47 (d, J=8.1 Hz, 1H), 3.22 (d, J=14.1 Hz, 1H), 2.88 (d, J=14.1 Hz, 1H), 2.83 (sept, J=6.6 Hz, 1H), 2.60 (sept, J=6.6 Hz, 1H), 2.01 (s, 3H), 1.60 (s, 3H), 1.41 (d, J=6.6 Hz, 3H), 1.40 (s, 3H), 1.21 (d, J=6.6 Hz, 3H), 1.19 (d, J=6.6 Hz, 3H), 1.15 (d, J=6.6 Hz, 3H) $^{13}$C NMR (125 MHz, CD$_3$CN): δ (ppm) 190.4, 145.7, 145.4, 139.7, 134.2, 133.7, 133.1, 130.8, 130.1, 128.9, 128.7, 128.2, 128.1, 126.7, 126.5, 125.6, 124.4, 85.3, 55.9, 48.5, 29.9, 29.7, 27.4, 26.9, 26.9, 25.7, 25.6, 21.6, 21.5.

$^{11}$B NMR (128 MHz, CDCl$_3$): δ (ppm) −0.91.

$^{19}$F NMR (376 MHz, CDCl$_3$): δ (ppm) −150.9 (small), 151.0.

HRMS for $C_{29}H_{36}N$ (M$^+$): calc.: 398.2842, found: 398.2839.

1-(2,6-diisopropylphenyl)-4-(3,5-dimethylphenyl)-2,2,4-trimethyl-3,4-dihydro-2H-pyrrol-1-ium tetrafluoroborate (CAAC-4)

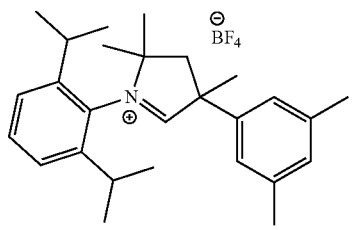

Chemical Formula: $C_{27}H_{38}BF_4N$
Molecular Weight: 463.41

CAAC-4 was prepared according to the 3-step procedure for CAAC synthesis with 2,6-diisopropylaniline (0.9 equiv) and 2-(3,5-dimethyl-phenyl)propanal (1 equiv). The desired product was obtained as a white powder (61% yield).

$^1$H NMR (500 MHz, CDCl$_3$): δ (ppm) 9.59 (s, 1H), 7.51 (t, J=7.5 Hz, 1H), 7.34 (d, J=7.5 Hz, 1H), 7.29 (d, J=7.5 Hz, 1H), 7.06 (s, 2H), 6.97 (s, 1H), 3.16 (d, J=14.0 Hz, 1H), 2.67 (sept, J=6.5 Hz, 1H), 2.66 (d, J=14.0 Hz, 1H), 2.39 (sept, J=6.5 Hz, 1H), 2.31 (s, 6H), 1.87 (s, 3H), 1.52 (s, 3H), 1.35 (d, J=6.5 Hz, 3H), 1.31 (s, 3H), 1.18 (d, J=6.5 Hz, 3H), 1.16 (d, J=6.5 Hz, 3H), 1.12 (d, J=6.5 Hz, 3H).

$^{13}$C NMR (125 MHz, CDCl$_3$): δ (ppm) 191.0, 145.2, 144.6, 141.2, 140.1, 132.4, 130.5, 129.3, 125.8, 123.6, 83.6, 55.3, 48.5, 30.0, 29.1, 28.7, 27.0, 26.4, 25.9, 25.7, 22.2, 21.9, 21.2.

$^{11}$B NMR (128 MHz, CDCl$_3$): δ (ppm) −0.99.

$^{19}$F NMR (376 MHz, CDCl$_3$): δ (ppm) −151.2 (small), 151.3.

HRMS for $C_{27}H_{38}N$ (M$^+$): calc.: 376.2999, found: 376.2997.

4-(3,5-di-tert-butylphenyl)-1-(2,6-diisopropylphenyl)-2,2,4-trime-thyl-3,4-dihydro-2H-pyrrol-1-ium tetrafluoroborate (CAAC-5)

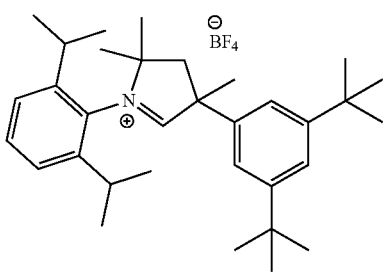

Chemical Formula: $C_{33}H_{50}BF_4N$
Molecular Weight: 547.57

CAAC-5 was prepared according to the 3-step procedure for CAAC synthesis 2-(3,5-di-tert-butyl-phenyl)propanal (1 equiv). The desired product was obtained as a white powder (39% yield).

$^1$H NMR (300 MHz, CDCl$_3$): δ (ppm) 10.98 (s, 1H), 7.48 (t, J=7.8 Hz, 1H), 7.45 (s, 2H), 7.41 (s, 1H), 7.33 (d, J=7.8 Hz, 1H), 7.27 (d, J=7.8 Hz, 1H), 3.18 (d, J=13.8 Hz, 1H), 2.71 (sept, J=6.9 Hz, 1H), 2.66 (d, J=13.8 Hz, 1H), 2.33 (sept, J=6.9 Hz, 1H), 2.03 (s, 3H), 1.55 (s, 3H), 1.38 (s, 3H), 1.37 (d, J=6.9 Hz, 3H), 1.34 (s, 18H), 1.31 (d, J=6.9 Hz, 3H), 1.16 (d, J=6.9 Hz, 3H), 1.10 (d, J=6.9 Hz, 3H)

$^{13}$C NMR (125 MHz, CDCl$_3$): δ (ppm) 192.0, 153.1, 145.3, 144.6, 139.7, 132.2, 129.2, 125.7, 122.8, 120.7, 82.6, 56.4, 48.5, 35.2, 31.4, 30.1, 29.8, 29.2, 27.3, 26.9, 26.7, 26.3, 22.1, 21.9.

$^{11}$B NMR (128 MHz, CDCl$_3$): δ (ppm) −0.98.

$^{19}$F NMR (376 MHz, CDCl$_3$): δ (ppm) −150.8 (small), 150.9.

HRMS for $C_{33}H_{50}N$ (M$^+$): calc.: 460.3938, found: 460.3931.

4-cyclohexyl-1-(2,6-diisopropylphenyl)-2,2,4-trimethyl-3,4-dihydro-2H-pyrrol-1-ium tetrafluoroborate (CAAC-6)

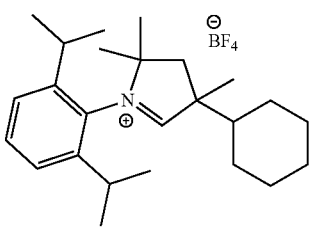

Chemical Formula: $C_{25}H_{40}BF_4N$
Molecular Weight: 441.41

CAAC-6 was prepared according to the 3-step procedure for CAAC synthesis with 2,6-diisopropylaniline (0.9 equiv) and 2-cyclohexylpropa-nal (1 equiv). The desired product was obtained as a white powder (83% yield).

$^1$H NMR (500 MHz, CD$_3$CN): δ (ppm) 8.84 (s, 1H), 7.61 (t, J=8.0 Hz, 1H), 7.48 (d, J=8.0 Hz, 2H), 7.48 (d, J=8.0 Hz, 2H), 2.69 (sept, J=7.0 Hz, 2H), 2.56 (d, J=14.0 Hz, 1H), 2.23 (d, J=14.0 Hz, 1H), 1.85 (m, 4H), 1.56 (s, 3H), 1.55 (s, 3H), 1.51 (s, 3H), 1.39 (m, 4H), 1.35 (d, J=7.0 Hz, 3H), 1.34 (d, J=7.0 Hz, 3H), 1.24 (m, 2H), 1.11 (d, J=7.0 Hz, 3H), 1.07 (d, J=7.0 Hz, 3H).

$^{13}$C NMR (125 MHz, CD$_3$CN): δ (ppm) 193.1, 146.2, 145.6, 145.6, 132.9, 126.5, 126.4, 84.7, 55.9, 45.5, 43.9, 30.0, 29.5, 29.2, 27.9, 27.8, 27.5, 26.3, 26.2, 26.1, 25.6, 25.5, 21.7, 21.6, 21.4.

$^{11}$B NMR (128 MHz, CDCl$_3$): δ (ppm) −1.04.

$^{19}$F NMR (376 MHz, CDCl$_3$): δ (ppm) −151.6 (small), 151.6

HRMS for $C_{25}H_{40}N$ (M$^+$): calc.: 354.3155, found: 354.3154.

1-(2,6-diisopropylphenyl)-2,2,4-trimethyl-4-phenyl-3,4-dihydro-2H-pyrrol-1-ium tetrafluoroborate (CAAC-7)

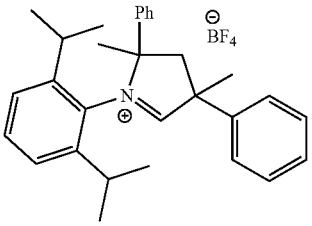

Chemical Formula: C$_{30}$H$_{36}$BF$_4$N
Molecular Weight: 497.43

CAAC-7 was prepared according to the 3-step procedure for CAAC synthesis with 2,6-diisopropylaniline (0.9 equiv) and 2-phenylpropanal (1 equiv). The desired product was obtained as a white powder (82% yield).

$^1$H NMR (400 MHz, CDCl$_3$): δ (ppm) 10.00 (s, 0.85H), 9.75 (s, 0.15H), 7.66-7.59 (m, 2H), 7.59-7.49 (m, 4H), 7.49-7.40 (m, 2H), 7.37 (q, J=6.8 Hz, 1H), 7.10-7.04 (m, 1H), 7.04-6.97 (m, 2H), 6.94 (d, J=7.8 Hz, 1H), 3.90 (d, J=14.2 Hz, 0.15H), 3.57 (d, J=13.6 Hz, 0.85H), 3.41 (d, J=13.5 Hz, 0.85H), 3.06 (d, J=14.2 Hz, 0.15H), 3.02-2.90 (m, 0.15H), 2.72 (sept, J=6.7 Hz, 1H), 2.24 (s, 0.5H), 2.08 (s, 2.5H), 1.77 (sept, J=6.8 Hz, 0.85H), 1.62 (s, 3H), 1.38 (d, J=7.0 Hz, 6H), 1.01 (d, J=6.9 Hz, 2.5H), 0.89 (d, J=6.8 Hz, 0.5H), 0.22 (2d, J=6.8 Hz, 3H).

$^{13}$C NMR (101 MHz, CDCl$_3$): δ (ppm) 189.8, 145.7, 145.4, 142.0, 133.2, 130.8, 130.0, 129.6, 126.7, 126.6, 126.6, 85.3, 55.7, 48.6, 29.9, 29.7, 27.2, 26.8, 26.8, 25.6, 25.5, 21.5, 21.4.

$^{11}$B NMR (128 MHz, CDCl$_3$): δ (ppm) −0.98.

$^{19}$F NMR (376 MHz, CDCl$_3$): δ (ppm) −151.0 (small), 151.1

HRMS for C$_{25}$H$_{34}$N (M$^+$): calc.: 348.2686, found: 348.2680.

1-(2,6-diethylphenyl)-2,2,4-trimethyl-4-phenyl-3,4-dihydro-2H-pyrrol-1-ium tetrafluoroborate (CAAC-8)

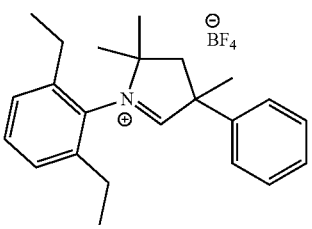

Chemical Formula: C$_{23}$H$_{30}$BF$_4$N
Molecular Weight: 407.30

CAAC-8 was prepared according to the 3-step procedure for CAAC synthesis with 2,6-diethylaniline (0.9 equiv) and 2-phenylpropanal (1 equiv). The desired product was obtained as a white powder (75% yield).

$^1$H NMR (500 MHz, CDCl$_3$): δ (ppm) 9.55 (s, 1H), 7.47 (t, J=7.5 Hz, 2H), 7.44 (d, J=7.5 Hz, 2H), 7.42 (d, J=7.5 Hz, 1H), 7.33 (t, J=7.5 Hz, 1H), 7.31 (d, J=7.5 Hz, 1H), 7.24 (d, J=7.5 Hz, 1H), 3.16 (d, J=14.0 Hz, 1H), 2.67 (d, J=14.0 Hz, 1H), 2.55 (q, J=7.5 Hz, 2H), 2.33 (dt, J=7.5 Hz, 1H), 2.16 (dt, J=7.5 Hz, 1H), 1.91 (s, 3H), 1.52 (s, 3H), 1.31 (s, 3H), 1.26 (t, J=7.5 Hz, 3H), 1.09 (t, J=7.5 Hz, 3H).

$^{13}$C NMR (125 MHz, CDCl$_3$): δ (ppm) 190.5, 141.0, 140.2, 139.7, 131.8, 131.0, 130.3, 128.9, 128.3, 128.1, 126.0, 83.8, 55.5, 48.3, 28.9, 26.9, 26.6, 24.8, 24.6, 15.3, 14.5.

$^{11}$B NMR (128 MHz, CDCl$_3$): δ (ppm) −0.98.

$^{19}$F NMR (376 MHz, CDCl$_3$): δ (ppm) −151.0 (small), 151.1.

HRMS for C$_{23}$H$_{30}$N (M$^+$): calc.: 320.2373, found: 320.2369.

1-(2,6-diethylphenyl)-2,2,4-trimethyl-4-(naphthalen-1-yl)-3,4-dihy-dro-2H-pyrrol-1-ium tetrafluoroborate (CAAC-9)

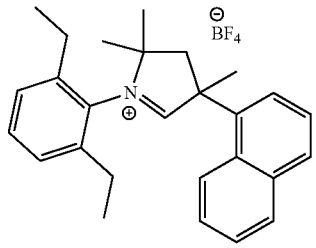

Chemical Formula: C$_{27}$H$_{32}$BF$_4$N
Molecular Weight: 457.36

CAAC-9 was prepared according to the 3-step procedure for CAAC synthesis with 2,6-diethylaniline (0.9 equiv) and 2-(naphthalen-1-yl)propanal (1 equiv). The desired product was obtained as a white powder (41% yield).

$^1$H NMR (500 MHz, CDCl$_3$): δ (ppm) 9.92 (s, 1H), 8.03 (d, J=7.5 Hz, 1H), 7.94 (d, J=7.5 Hz, 1H), 7.84 (d, J=7.5 Hz, 1H), 7.62 (t, J=7.5 Hz, 1H), 7.56 (t, J=7.5 Hz, 1H), 7.49 (t, J=7.5 Hz, 1H), 7.43 (t, J=7.5 Hz, 1H), 7.41 (d, J=7.5 Hz, 1H), 7.34 (d, J=7.5 Hz, 1H), 7.32 (d, J=7.5 Hz, 1H), 3.28 (d, J=13.5 Hz, 1H), 3.14 (d, J=13.5 Hz, 1H), 2.61 (q, J=7.5 Hz, 2H), 2.52 (q, J=7.5 Hz, 2H), 2.21 (s, 3H), 1.54 (s, 3H), 1.31 (t, J=7.5 Hz, 3H), 1.30 (t, J=7.5 Hz, 3H), 1.27 (s, 3H).

$^{13}$C NMR (125 MHz, CDCl$_3$): δ (ppm) 191.5, 140.3, 139.5, 138.3, 135.8, 132.0, 131.0, 130.7, 130.2, 129.2, 128.4, 128.4, 127.2, 126.6, 125.8, 124.7, 123.5, 84.0, 55.8, 50.3, 28.1, 27.2, 27.0, 25.0, 24.8, 15.3, 14.6.

$^{11}$B NMR (128 MHz, CDCl$_3$): δ (ppm) −0.98.

$^{19}$F NMR (376 MHz, CDCl$_3$): δ (ppm) −151.0 (small), 151.1

HRMS for C$_{27}$H$_{32}$N (M$^+$) 370.2529, found 370.2522.

1-(2,6-diethylphenyl)-2,2,4-trimethyl-4-(naphthalen-2-yl)-3,4-dihy-dro-2H-pyrrol-1-ium tetrafluoroborate (CAAC-10)

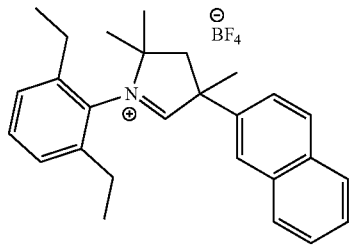

Chemical Formula: $C_{27}H_{32}BF_4N$
Molecular Weight: 457.36

CAAC-10 was prepared according to the 3-step procedure for CAAC synthesis with 2,6-diethylaniline (0.9 and 2-(naphthalen-2-yl)propanal (1 equiv). The desired product was obtained as a white powder (71% yield).

$^1$H NMR (400 MHz, CD$_3$CN/CDCl$_3$ 1/1): δ (ppm) 9.33 (s, 1H), 8.02 (d, J=8.7 Hz, 1H), 7.93-7.81 (m, 3H), 7.61-7.54 (m, 3H), 7.54-7.49 (m, 1H), 7.43-7.33 (m, 2H), 3.18 (d, J=14.0 Hz, 1H), 2.82 (d, J=14.0 Hz, 1H), 2.69 (dq, J=15.1, 7.6 Hz, 1H), 2.52 (dq, J=15.2, 7.5 Hz, 2H), 2.32 (dq, J=14.7, 7.4 Hz, 1H), 2.01 (s, 3H), 1.58 (s, 3H), 1.38 (s, 3H), 1.28 (t, J=7.5 Hz, 3H), 1.17 (t, J=7.5 Hz, 3H).

$^{13}$C NMR (101 MHz, CD$_3$CN/CDCl$_3$ 1/1): δ (ppm) 196.2, 145.0, 144.9, 143.5, 138.6, 138.1, 137.1, 135.6, 135.4, 133.6, 133.4, 133.1, 132.7, 132.6, 129.9, 129.8, 128.4, 90.1, 60.8, 54.0, 33.2, 32.3, 32.3, 30.3, 30.2, 20.7, 20.4.

$^{11}$B NMR (128 MHz, CDCl$_3$): δ (ppm) 4.2.

$^{19}$F NMR (376 MHz, CDCl$_3$): δ (ppm) −147.0 (small), −147.1.

HRMS for $C_{27}H_{32}N$ (M$^+$) 370.2529, found 370.2522.

1-(2,6-diethylphenyl)-4-(3,5-dimethylphenyl)-2,2,4-trimethyl-3,4-di-hydro-2H-pyrrol-1-ium tetrafluoroborate (CAAC-11)

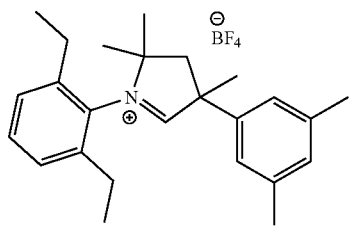

Chemical Formula: $C_{25}H_{34}BF_4N$
Molecular Weight: 435.36

CAAC-11 was prepared according to the 3-step procedure for CAAC synthesis with 2,6-diethylaniline (0.9 equiv) and 2-(3,5-dimethylphenyl)propanal (1 equiv). The desired product was obtained as a white powder (44% yield).

$^1$H NMR (500 MHz, CDCl$_3$): δ (ppm) 9.57 (s, 1H), 7.46 (t, J=7.5 Hz, 1H), 7.32 (d, J=7.5 Hz, 1H), 7.25 (d, J=7.5 Hz, 1H), 7.05 (s, 2H), 6.98 (s, 1H), 3.11 (d, J=14.0 Hz, 1H), 2.63 (d, J=14.0 Hz, 1H), 2.58 (dt, J=7.5 Hz, 1H), 2.57 (dt, J=7.5 Hz, 1H), 2.39 (dt, J=7.5 Hz, 1H), 2.22 (dt, J=7.5 Hz, 1H), 2.32 (s, 6H), 1.92 (s, 3H), 1.52 (s, 3H), 1.31 (s, 3H), 1.29 (t, J=7.5 Hz, 3H), 1.15 (t, J=7.5 Hz, 3H).

$^{13}$C NMR (125 MHz, CDCl$_3$): δ (ppm) 190.9, 141.2, 140.4, 140.2, 139.8, 131.8, 131.0, 130.5, 128.3, 128.1, 123.6, 83.6, 55.3, 48.7, 28.8, 27.0, 26.7, 24.8, 24.7, 21.2, 15.5, 14.5.

$^{11}$B NMR (128 MHz, CDCl$_3$): δ (ppm) −0.98.

$^{19}$F NMR (376 MHz, CDCl$_3$): δ (ppm) −151.0 (small), 151.1.

HRMS for $C_{25}H_{34}N$ (M$^+$): calc.: 348.2686, found: 348.2682.

4-cyclohexyl-1-(2,6-diethylphenyl)-2,2,4-trimethyl-3,4-dihydro-2H-pyrrol-1-ium tetrafluoroborate (CAAC-12)

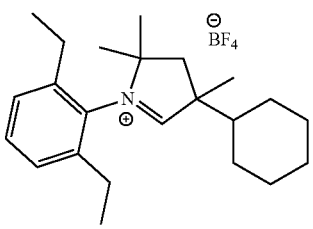

Chemical Formula: $C_{23}H_{36}BF_4N$
Molecular Weight: 413.35

CAAC-12 was prepared according to the 3-step procedure for CAAC synthesis with 2,6-diethylaniline (0.9 equiv) and 2-cyclohexylpropanal (1 equiv). The desired product was obtained as a white powder (74% yield).

$^1$H NMR (300 MHz, CDCl$_3$) δ (ppm) 9.11 (s, 1H), 7.45 (t, 1H, J=7.8 Hz), 7.29 (d, 1H, J=7.8 Hz), 7.27 (d, 1H, J=7.8 Hz), 2.55-2.63 (m, 1H), 2.45-2.55 (m, 3H), 2.33-2.45 (m, 1H), 2.05-2.17 (m, 2H), 1.71-1.89 (m, 4H) 1.64 (s, 3H), 1.53 (s, 3H), 1.48 (s, 3H), 1.41-1.53 (m, 2H), 1.25 (t, 3H, J=7.5 Hz), 1.21-1.27 (m, 3H), 1.18 (t, 3H, J=7.5 Hz), 093-1.05 (m, 1H)

$^{13}$C{$^1$H} NMR (125 MHz, CDCl$_3$) δ (ppm) 194.2, 140.1, 140.1, 131.7, 131.0, 128.1, 128.1, 83.3, 56.0, 44.0, 43.2, 29.8, 28.2, 27.8, 26.6, 25.8, 25.8, 25.6, 25.3, 24.3, 23.2, 15.4, 14.6.

$^{11}$B NMR (128 MHz, CDCl$_3$): δ (ppm) −0.98.

$^{19}$F NMR (376 MHz, CDCl$_3$): δ (ppm) −151.0 (small), 151.1

HRMS (ESI): for $C_{23}H_{36}N$ (M$^+$): calc.: 326.2842, found 326.2839.

1-(2,6-diethylphenyl)-2,2,4-trimethyl-4-phenyl-3,4-dihydro-2H-pyrrol-1-ium tetrafluoroborate (CAAC-13)

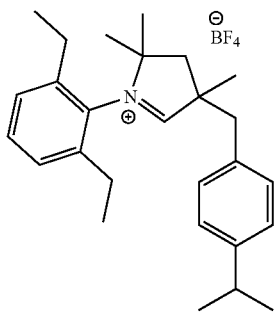

Chemical Formula: $C_{27}H_{38}BF_4N$
Molecular Weight: 463.41

CAAC-13 was prepared according to the 3-step procedure for CAAC synthesis with 2,6-diethylaniline (0.9 equiv) and 3-(4-isopropylphenyl)-2-methylpropanal (1 equiv). The desired product was obtained as a white powder (75% yield).

$^1$H NMR (500 MHz, $C_6D_6$): δ (ppm) 9.38 (s, 1H), 7.45 (t, J=7.7 Hz, 1H), 7.35-7.29 (m, 3H), 7.27-7.21 (m, 3H), 3.75 (d, J=14.0 Hz, 1H), 2.93 (sept, J=6.9 Hz, 1H), 2.86 (d, J=14.0 Hz, 1H), 2.72 (d, J=13.7 Hz, 1H), 2.51 (q, J=7.5 Hz, 2H), 2.27 (d, J=13.7 Hz, 1H), 1.89-1.78 (m, 5H), 1.45 (s, 3H), 1.32 (d, J=7.4 Hz, 3H), 1.26 (dd, J=6.9, 1.8 Hz, 6H), 1.11 (t, J=7.5 Hz, 3H), 0.98 (s, 3H).

$^{13}$C NMR (125 MHz, $C_6D_6$): δ (ppm) 192.5, 148.4, 139.8, 139.4, 133.4, 131.2, 130.5, 130.4 (2C), 127.6 (2C), 127.2 (2C), 83.0, 54.5, 44.4, 43.6, 33.8, 28.1, 27.9, 27.4, 24.7, 24.4, 24.0, 24.0, 15.3, 14.9.

$^{11}$B NMR (128 MHz, $CDCl_3$): δ (ppm) −0.89.

$^{19}$F NMR (376 MHz, $CDCl_3$): δ (ppm) −151.1 (small), 151.2.

HRMS for $C_{23}H_{30}N$ (M$^+$): calc.: 320.2373, found: 320.2369.

1-(2-isopropyl-6-methylphenyl)-2,2,4-trimethyl-4-phenyl-3,4-dihy-dro-2H-pyrrol-1-ium tetrafluoroborate (CAAC-14)

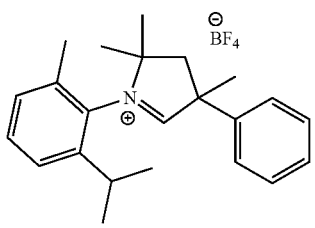

Chemical Formula: $C_{23}H_{30}BF_4N$
Molecular Weight: 407.30

CAAC-14 was prepared according to the 3-step procedure for CAAC synthesis with 2-isopropyl-6-methylaniline (0.9 equiv) and 2-phenylpropanal (1 equiv). The desired product was obtained as a white powder (58% yield) as a mixture of diastereoisomers (55/45).

$^1$H NMR (400 MHz, $CDCl_3$): δ (ppm) 9.26 (s, 1H), 7.64 (t, J=7.5 Hz 1H), 7.55 (t, J=7.5 Hz, 2H), 7.52 (d, J=7.5 Hz, 1H), 7.48 (d, J=7.5 Hz, 2H), 7.45 (d, J=7.5 Hz, 2H), 3.10 (d, J=14.0 Hz, 1H), 2.82 (d, J=14.0 Hz, 1H), 2.79 (sept, J=7.0 Hz, 1H), 2.55 (sept, J=7.0 Hz, 1H), 1.93 (s, 3H), 1.58 (s, 3H), 1.40 (s, 3H), 1.39 (d, J=7.0 Hz, 3H), 1.25 (d, J=7.0 Hz, 3H), 1.15 (d, J=7.0 Hz, 3H), 1.08 (d, J=7.0 Hz, 3H).

$^{13}$C NMR (101 MHz, $CDCl_3$): δ (ppm) 189.8, 145.7, 145.4, 142.0, 133.2, 130.8, 130.0, 129.6, 126.7, 126.6, 126.6, 85.3, 55.7, 48.6, 29.9, 29.7, 27.2, 26.8, 26.8, 25.6, 25.5, 21.5, 21.4.

$^{11}$B NMR (128 MHz, $CDCl_3$): δ (ppm) −1.03.

$^{19}$F NMR (376 MHz, $CDCl_3$): δ (ppm) −151.27(small), −151.33.

Analytical data were consistent with the previously reported data (Kozakiewicz, A.; Chwalba, M.; Skowerski, K.; Gawin, R.; Tracz, A.; Trzaskowski, B. *ACS Catal.* 2017, 7, 5443-5449. https://doi.org/10.1021/acscatal.7b00597).

1-(diphenylamino)-2,2,4-trimethyl-4-phenyl-3,4-dihydro-2H-pyrrol-1-ium tetrafluoroborate (CAAC-15)

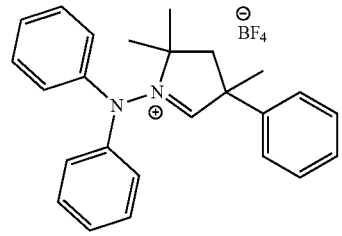

Chemical Formula: $C_{25}H_{27}BF_4N_2$
Molecular Weight: 442.31

CAAC-15 was prepared according to the following procedure: In a 100 ml round bottom flask were added 2,4-dimethyl-2-phenylpent-4-enal (5 g, 26.55 mmol, 1 equiv) (obtained following literature procedures: (REF1) H., K., Diet, *Tetrahedron Let.* 1973, 1273; (REF2) V. G. Purohit, R. Subramanian, *Chem. Ind.* 1978, 731.), 1,1-diphenylhydrazine (5.38 g, 29.21 mmol, 1.1 equiv), p-toluenesulfonic acid (10 mg; catalytic amount) and toluene (60 mL). The flask was fitted with a dean stark apparatus and set to reflux for 16 h. After this time the solution was transferred in a 100 ml pressure Schlenk fitted with a magnetic stir bar and slowly concentred under vacuum. Further evaporation of the volatiles under vacuum at 100° C. afforded a brown oily residue which was cooled to −78° C. Under an argon atmosphere HCl (2M in $Et_2O$) (27.88 ml, 55.77 mmol, 2 equiv) was then added and the pressure schlenk was sealed under argon. The vessel was brought back to room temperature and set to heat at 100° C. for 24 h. After time the vessel was brought back to room temperature and the volatiles were removed under vacuum. The resulting residue was taken into $CH_2Cl_2$ (50 ml) and triturated with an aqueous solution $NaBF_4$ (6.12 g, 55.77 mmol, 2.1 equiv). Subsequent separation of the organic phase, washing with water (3 times) afforded a brown crude residue after evaporation of the volatiles. Trituration with $Et_2O$ (50 ml) enforced the precipitation of the desired product which was separated by filtration and further washed with $Et_2O$ (2×50 ml). The desired product was further dried under vacuum and obtained as an off-white powder (7.86 g, 67% yield).

$^1$H NMR (400 MHz, CDCl$_3$): δ (ppm) 9.16 (s, 1H), 7.54-7.44 (m, 4H), 7.44-7.34 (m, 5H), 7.33-7.29 (m, 4H), 7.11-7.04 (m, 2H), 3.00 (d, J=13.7 Hz, 1H), 2.58 (d, J=13.8 Hz, 1H), 1.90 (s, 3H), 1.63 (s, 3H), 1.39 (s, 3H).

$^{13}$C NMR (101 MHz, CDCl$_3$): δ (ppm) 181.2, 143.9 (2C), 141.0, 130.6 (4C), 129.9 (2C), 128.5 (2C), 128.5, 125.3 (2C), 124.7 (4C), 81.7, 52.0, 48.0, 29.0, 28.4, 26.9.

$^{11}$B NMR (128 MHz, CDCl$_3$): δ (ppm) −0.92.

$^{19}$F NMR (376 MHz, CDCl$_3$): δ (ppm) 150.6.

Complexes Synthesis

Reagents used for complexes synthesis: Synthesized salts were dried at 60° C. under high vacuum overnight before complexation. KHMDS (0.5 M in toluene) and CuCl were purchased from Sigma Aldrich and used as received. M10 complex was 94% w pure and purchased from Umicore AG & co and used as received. 2-isopropoxystyrene (1)(Garber, S. B.; Kingsbury, J. S.; Gray, B. L.; Hoveyda, A. H. *J. Am. Chem. Soc.* 2000, 122, 8168-8179. https://doi.org/10.1021/ja001179g), 1-isopropoxy-4-nitro-2-vinylbenzene (2) (Michrowska, A.; Bujok, R.; Harutyunyan, S.; Sashuk, V.; Dolgonos, G.; Grela, K. *J. Am. Chem. Soc.* 2004, 126, 9318-9325. https://doi.org/10.1021/ja048794v) and 2-isopropoxy-3-vinylbiphenyl (3)(Van Veldhuizen, J. J.; Gillingham, D. G.; Garber, S. B.; Kataoka, O.; Hoveyda, A. H. *J. Am. Chem. Soc.* 2003, 125, 12502-12508. https://doi.org/10.1021/ja0302228), were synthesized from salicylaldehyde by alkylation and Wittig olefination following a previously reported procedure. (2-vinyl)benzooxazinone (4)(Nelson, D. J.; Queval, P.; Rouen, M.; Magrez, M.; Caijo, F.; Borré, E.; Laurent, I.; Crévisy, C.; Baslé, O.; Mauduit, M.; et al. *ACS Catal.* 2013, 3, 259-264. https://doi.org/10.1021/cs400013z) was synthetised from commercialy available 2-amino-6-bromophenol by subsequent condensation with the corresponding acyl chloride, cyclisation and Stille coupling.

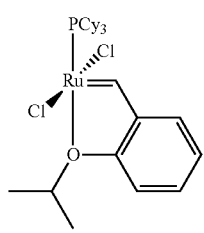

HG1

Chemical Formula: C$_{28}$H$_{45}$Cl$_2$OPRu
Molecular Weight: 600.61

Hoveyda-Grubbs 1$^{st}$ generation (HG1) complex was previously synthesized using the following procedure: In an oven dried Schlenk under Ar, were placed Dichloro(3-phenyl-1H-inden-1-ylidene) bis(tricyclohexylphosphine)ruthenium(II) (M1, purchased from Umicore) complex (2.0 g, 2.17 mmol, 1 equiv) and CuCl (236.0 mg, 2.38 mmol, 1.1 equiv). A solution of 2-isopropoxystyrene (synthesized from salicylaldehyde by alkylation and Wittig olefination following a previously reported procedure)[1] (390.0 mg, 2.40 mmol, 1.1 equiv) in DCM (6 mL) was added, then DCM was added to obtain 50 mL of solution. The resulting mixture was stirred for 2 h at 40° C. The reaction was monitored by TLC (Pentane:Acetone 9:1) until the complete disappearance of M1. DCM was evaporated under reduced pressure and the solid was taken up in Acetone (HPLC grade) and filtered through a celite pad until the undesired solid became whitish. Volatiles were removed under vacuum and the solid obtained was dissolved in CHCl$_3$ and filtered off. The filtrate was evaporated, the solid was dissolved in warm Et$_2$O and the complex was precipitated with Pentane (3 times). The mixture was filtered off and the brown solid was collected (955 mg, 73% yield).

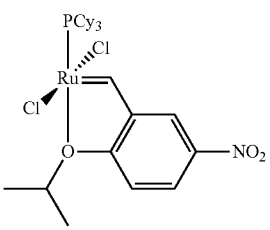

Grela 1

Chemical Formula: C$_{28}$H$_{44}$Cl$_2$NO$_3$PRu
Molecular Weight: 645.61

Grela 1$^{st}$ generation (Grela-1) complex was previously synthesized using the following procedure: In an oven dried Schlenk under Ar, were placed Dichloro(3-phenyl-1H-inden-1-ylidene) bis(tricyclohexylphosphine)ruthenium(II) (M1, purchased from Umicore) complex (1.0 g, 1.08 mmol, 1 equiv) and CuCl (174.1 mg, 1.76 mmol, 1.6 equiv). A solution of 1-isopropoxy-4-nitro-2-vinylbenzene (synthesized from 2-hydroxy-5-nitrobenzaldehyde by alkylation and Wittig olefination following a previously reported procedure)[3] (523.6 mg, 2.53 mmol, 2.3 equiv) in DCM (5 mL) was added, then DCM (5 mL) was added. The resulting mixture was stirred for 5 h at 35° C. The reaction was monitored by $^{31}$P NMR. DCM was evaporated under reduced pressure and the solid was taken up in Acetone (HPLC grade) and filtered through a celite pad until the undesired solid became whitish. The volatiles were removed under reduced pressure. The crude mixture was purified by chromatography on silica gel (pentane:Et$_2$O 95:5 then 7:3) and the resulting solid washed with pentane to afford the desired complex as a brown solid (426 mg, 61% yield).

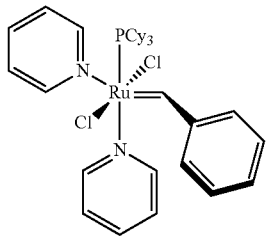

Grubbs 3

Chemical Formula: C$_{28}$H$_{44}$Cl$_2$NO$_3$PRu
Molecular Weight: 645.61

Grubbs 3$^{rd}$ generation was synthetised using the following procedure. In an oven-dried Schlenk in the glovebox, Grubbs I catalyst (Dichloro(benzylidene) bis(tricyclohexylphosphine) ruthenium(II) purchased from Umicore) (500 mg, 0.12 mmol, 1 equiv) was dissolved in Toluene (10 mL), followed by the addition of dry and degassed pyridine (1 mL, 3.1 mL, 25 equiv) and the resulting mixture was stirred during 2 h at rt. The resulting crude product was added dropwise to cold pentane (−20° C.) and the all was left during 2 h in the freezer to complete the precipitation. The liquid was removed and the resulting solid was washed twice with pentane and dried under vacuum to afford a bright green solid (385 mg, 93% yield). Analytical data were consistent with the previously reported data (Getty, K.; Delgado-Jaime, M. U.; Kennepohl, P. *Inorganica Chim. Acta* 2008, 361, 1059-1065. https://doi.org/https://doi.org/10.1016/j.ica.2007.07.029).

a. General Procedure for dipp-CAAC Starting from HG1

Scheme S1 General procedure A

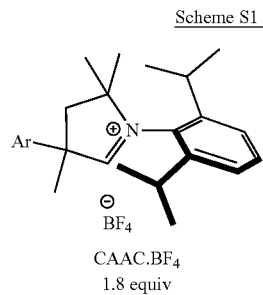

1) KHMDS (1.9 equiv), Toluene, rt, 30 min
2) HG1 (1 equiv), rt

CAAC.BF$_4$
1.8 equiv

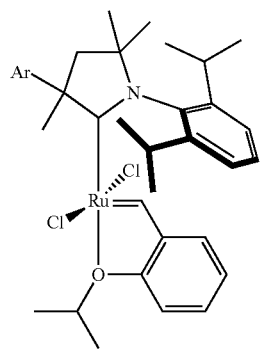

Ru-1: Ar = Ph (63% yield)
Ru-3: Ar = 1-Napht (84% yield)

General Procedure A: In a glove box, CAAC·BF$_4$ (1.8 equiv) was dissolved in dry and degassed THF (30 mL/mmol Ru). KHMDS (0.5 M in toluene, 1.9 equiv) was added. The mixture was allowed to stirred 30 min at rt. Then, HG1 complex (1 equiv) was then added. The mixture was stirred the indicated time at rt.

The solvent was removed under vacuum and the product was purified by column chromatography (Pentane:Acetone 9:1). The solid was then diluted in the minimum amount of DCM and precipitated in pentane.

CAAC (Me/Ph-dipp)-Ru Hoveyda Type Complex (Ru-1a)

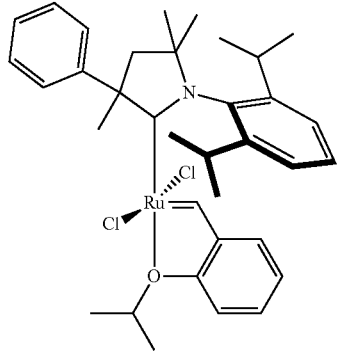

Chemical Formula: C$_{35}$H$_{45}$Cl$_2$NORu
Molecular Weight: 667.72

Ru-1a was prepared according to general procedure A for the synthesis of complexes with CAAC-1 (205 mg, 0.47 mmol, 1.7 equiv), THF (7.0 mL), KHMDS (1.0 mL, 0.50 mmol, 1.8 equiv) and HG1 complex (166 mg, 0.28 mmol, 1 equiv). The mixture was stirred 2 h. The desired product was obtained as a green solid (117 mg, 63% yield).

$^1$H NMR (400 MHz, CDCl$_3$): δ (ppm) 16.55 (s, 1H), 8.28 (d, J=7.8 Hz, 2H), 7.64 (t, J=7.7 Hz, 1H), 7.56 (t, J=7.6 Hz, 2H), 7.53-7.42 (m, 3H), 7.38 (t, J=7.3 Hz, 1H), 6.86 (d, J=8.4 Hz, 1H), 6.79 (t, J=7.4 Hz, 1H), 6.71 (dd, J$_1$=7.5, J$_2$=1.7 Hz, 1H), 4.96 (sept, J=6.1 Hz, 1H), 3.16 (d, J=12.9 Hz, 1H), 3.13-3.06 (m, 1H), 3.06-2.94 (m, 1H), 2.31-2.41 (m, 4H), 1.58 (d, J=6.1 Hz, 3H), 1.52 (s, 3H), 1.46-1.39 (m, 6H), 1.36 (d, J=6.6 Hz, 3H), 1.27 (d, J=6.7 Hz, 3H), 0.85 (d, J=6.5 Hz, 3H), 0.54 (d, J=6.3 Hz, 3H).

$^{13}$C NMR (101 MHz, CDCl$_3$): δ (ppm) 297.9, 264.7, 152.9, 148.6, 148.3, 143.0, 142.7, 136.8, 130.9, 129.6, 129.3, 129.2, 129.2, 129.2, 127.5, 126.0, 125.8, 124.0, 121.7, 113.4, 77.5, 74.7, 63.2, 48.3, 32.8, 28.9, 28.7, 28.3, 27.7, 27.4, 26.4, 24.5, 24.4, 22.6, 22.3.

CAAC (Me/1-Napht-dipp)-Ru Hoveyda Type Complex (Ru-2a)

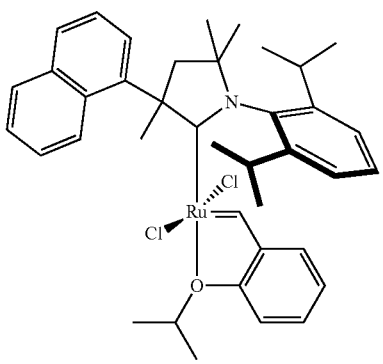

Chemical Formula: C$_{39}$H$_{47}$Cl$_2$NORu
Molecular Weight: 717.78

Ru-2a was prepared according to general procedure A for the synthesis of complexes with CAAC-2 (169 mg, 0.35 mmol, 1.8 equiv), THF (6.0 mL), KHMDS (0.7 mL, 0.35 mmol, 1.8 equiv) and HG1 complex (116 mg, 0.19 mmol, 1 equiv). The mixture was stirred 4 h. The desired product was obtained as a green solid (114 mg, 82% yield).

$^1$H NMR (400 MHz, CDCl$_3$): δ (ppm) 16.59 (s, 1H), 8.31 (d, J=8.7 Hz, 1H), 8.13 (dd, J=7.4, 1.2 Hz, 1H), 7.89 (dd, J=8.1, 1.6 Hz, 1H), 7.78 (d, J=8.1 Hz, 1H), 7.65 (t, J=7.7 Hz, 1H), 7.57-7.43 (m, 5H), 7.37 (dd, J=8.1, 7.4 Hz, 1H), 6.93 (d, J=8.4 Hz, 1H), 6.90-6.81 (m, 2H), 5.10 (sept, J=6.1 Hz, 1H), 3.57 (d, J=12.4 Hz, 1H), 3.48 (sept, J=6.6 Hz, 1H), 3.20 (s, 3H), 3.11 (sept, J=6.4 Hz, 1H), 2.58 (d, J=12.3 Hz, 1H), 1.72 (d, J=6.1 Hz, 3H), 1.59 (d, J=6.0 Hz, 3H), 1.29 (s, 3H), 1.24 (d, J=6.5 Hz, 3H), 1.20 (d, J=6.6 Hz, 3H), 1.11 (d, J=6.6 Hz, 3H), 0.84 (s, 3H), 0.61 (d, J=6.3 Hz, 3H).

$^{13}$C NMR (101 MHz, CDCl$_3$): δ (ppm) 295.7, 270.9, 153.1, 148.9, 148.6, 143.2, 138.8, 136.9, 135.3, 131.0, 130.4, 130.0, 129.8, 129.6, 128.8, 126.4 (2C), 126.0, 124.7, 124.5, 124.1, 123.7, 121.8, 113.4, 79.1, 75.1, 64.8, 50.3, 30.9, 29.6, 28.9, 28.4, 27.5, 26.0, 25.9, 25.1, 23.7, 22.3, 21.6.

HRMS for $C_{39}H_{47}NO^{35}Cl_2{}^{102}Ru$ (M$^{+\cdot}$): calc.: 717.20727, found: 717.2071 (0 ppm).

CAAC (Me/2-Napht-dipp)-Ru Hoveyda Type Complex (Ru-3a)

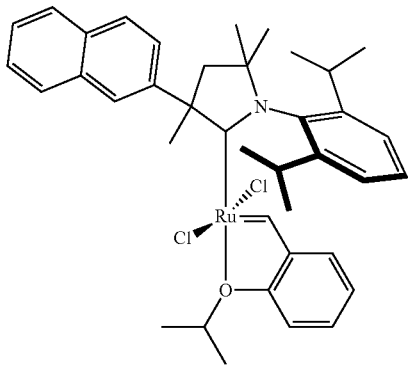

Chemical Formula: C$_{39}$H$_{47}$Cl$_2$NORu
Molecular Weight: 717.78

Ru-3a was prepared according to general procedure A for the complexes synthesis with CAAC-3 (618 mg, 1.27 mmol, 1.8 equiv), THF (20 mL), KHMDS (2.5 mL, 1.25 mmol, 1.8 equiv) and HG1 complex (419 mg, 0.70 mmol, 1 equiv). The mixture was stirred 4 h. The desired product was obtained as a green solid (300 mg, 60% yield).

$^1$H NMR (400 MHz, CDCl$_3$): δ (ppm) 16.54 (s, 1H), 8.72 (d, J=2.0 Hz, 1H), 8.29 (dd, J=8.8, 2.1 Hz, 1H), 8.05-8.03 (m, 2H), 7.91-7.89 (m, 1H), 7.67 (t, J=7.7 Hz, 1H), 7.54-7.43 (m, 4H), 7.30-7.15 (m, 1H), 6.80 (t, J=7.3 Hz, 2H), 6.74 (dd, J=7.5, 1.7 Hz, 1H), 4.81 (sept, J=6.2 Hz, 1H), 3.28 (d, J=12.8 Hz, 1H), 3.16 (sept, J=6.6 Hz, 2H), 2.52 (s, 3H), 2.45 (d, J=12.7 Hz, 1H), 1.56 (s, 3H), 1.48 (s, 3H), 1.39 (d, J=6.6 Hz, 3H), 1.32 (q, J=6.6 Hz, 6H), 1.02 (d, J=6.2 Hz, 3H), 0.90 (d, J=6.5 Hz, 3H), 0.59 (d, J=6.3 Hz, 3H).

$^{13}$C NMR (101 MHz, CDCl$_3$): δ (ppm) 297.6, 265.1, 153.0, 148.8, 148.4, 143.2, 139.6, 136.8, 133.7, 132.8, 130.9, 129.6, 129.1, 128.9, 128.4, 128.0, 127.5, 126.2, 126.1, 125.9, 125.8, 123.9, 121.8, 113.4, 77.9, 74.8, 63.2, 48.8, 32.7, 29.0, 28.9, 28.7, 27.6, 27.5, 26.4, 24.6, 24.4, 21.9, 21.8.

HRMS for $C_{39}H_{47}NO^{35}Cl_2{}^{102}Ru$ (M+.): calc.: 717.20727, found: 717.2075 (0 ppm).

CAAC (Me/2-Napht-dipp)-Ru Hoveyda Type Complex (Ru-4a)

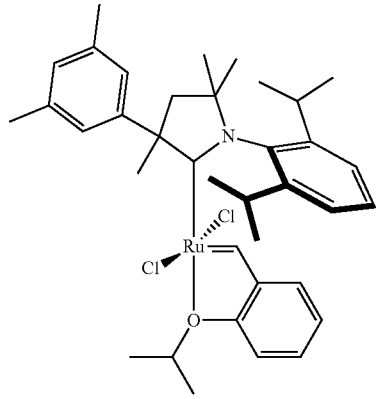

Chemical Formula: C$_{37}$H$_{49}$Cl$_2$NORu
Molecular Weight: 695.78

Ru-4a was prepared according to general procedure A for the complexes synthesis with CAAC-4 (576 mg, 1.24 mmol, 1.8 equiv), THF (20 mL), KHMDS (2.4 mL, 1.2 mmol, 1.8 equiv) and HG1 complex (402 mg, 0.67 mmol, 1 equiv). The mixture was stirred 4 h. The desired product was obtained as a green solid (366 mg, 78% yield).

$^1$H NMR (400 MHz, CDCl$_3$): δ (ppm) 16.55 (s, 1H), 7.76 (s, 2H), 7.67 (t, J=7.7 Hz, 1H), 7.53-7.46 (m, 3H), 7.31-7.21 (m, 1H), 7.03 (br. s, 1H), 6.88 (d, J=8.4 Hz, 1H), 6.81 (dt, J=7.2, 0.7 Hz, 1H), 6.76 (dd, J=7.6, 1.8 Hz, 1H), 4.98 (sept, J=6.1 Hz, 1H), 3.18-3.11 (m, 3H), 2.48 (s, 6H), 2.41-2.37 (m, 4H), 1.56-1.54 (d, J=6.1 Hz, 3H), 1.52 (s, 3H), 1.45 (s, 3H), 1.38 (dd, J=6.2, 1.6 Hz, 5H), 1.33 (d, J=6.6 Hz, 3H), 0.88 (d, J=6.4 Hz, 3H), 0.63 (d, J=6.4 Hz, 3H).

$^{13}$C NMR (101 MHz, CDCl$_3$): δ (ppm) 296.8, 265.5, 152.9, 148.8, 148.4, 143.2, 141.0, 137.7, 136.8, 130.7, 129.5, 129.1, 129.0, 128.4, 128.3, 126.0, 125.7, 125.4, 123.8, 121.8, 113.3, 77.7, 74.7, 62.7, 49.4, 32.5, 28.8, 28.2, 27.4, 27.1, 26.3, 24.6, 24.4, 22.0.

HRMS for $C_{37}H_{43}NO^{35}Cl_2{}^{102}Ru$ (M$^{+\cdot}$): calc.: 689.16032, found: 689.1762 (0 ppm).

a. General Procedure for Dipp-CAAC Starting from Grela-1

Scheme S2 General procedure B

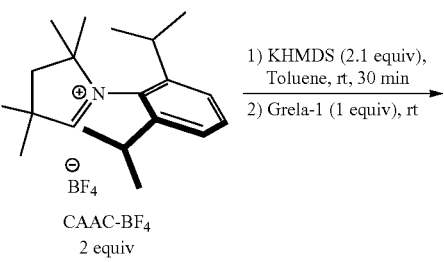

CAAC-BF$_4$
2 equiv

1) KHMDS (2.1 equiv), Toluene, rt, 30 min
2) Grela-1 (1 equiv), rt

-continued

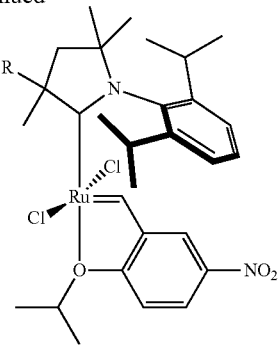

Ru-2: R = Ph (25% yield)
Ru4: R = 1-Napht (27% yield)
Ru-5: R = 3.5-MePh (44% yield)
Ru-6: R = Cy (29% yield)

General Procedure B: In a glove box, CAAC·BF$_4$ (2 equiv) was dissolved in dry and degassed Toluene (10 mL/mmol Ru). KHMDS (0.5 M in toluene, 2.1 equiv) was added. The mixture was allowed to stirred 30 min at rt. Then, Grela 1 complex (1 equiv) was then added. The mixture was stirred the indicated time at rt.

The solvent was removed under vacuum and the product was purified by column chromatography (eluent: Toluene). The solid was then diluted in the minimum amount of DCM and precipitated in pentane.

CAAC (Me/Ph-dipp)-Ru Grela Type Complex
(Ru-1b)

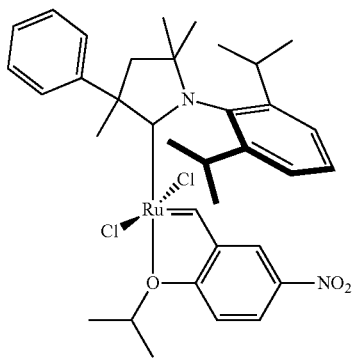

Chemical Formula: C$_{35}$H$_{44}$Cl$_2$N$_2$O$_3$Ru
Molecular Weight: 712.72

Ru-1 b was prepared according to general procedure B for the complexes synthesis with CAAC-1 (366 mg, 0.84 mmol, 1.9 equiv), Toluene (4.7 mL), KHMDS (1.8 mL, 0.90 mmol, 2 equiv) and Grela 1 complex (293 mg, 0.45 mmol, 1 equiv). The mixture was stirred 3 h. The desired product was obtained as a green solid (78.5 mg, 25% yield).

$^1$H NMR (400 MHz, CDCl$_3$): δ (ppm) 16.52 (s, 1H), 8.38 (dd, J=9.1, 2.7 Hz, 1H), 8.27-8.18 (m, 2H), 7.72 (t, J=7.8 Hz, 1H), 7.61-7.46 (m, 5H), 7.43-7.32 (m, 1H), 6.95 (d, J=9.2 Hz, 1H), 5.02 (sept, J=6.1 Hz, 1H), 3.16 (d, J=12.8 Hz, 1H), 3.05 (sept, J=6.6 Hz, 1H), 2.95 (sept, J=6.5 Hz, 1H), 2.40-2.32 (m, 4H), 1.57 (d, J=6.1 Hz, 3H), 1.53 (s, 3H), 1.46-1.39 (m, 6H), 1.36 (d, J=6.6 Hz, 3H), 1.27 (d, J=6.6 Hz, 3H), 0.84 (d, J=6.5 Hz, 3H), 0.50 (d, J=6.3 Hz, 3H).

$^{13}$C NMR (101 MHz, CDCl$_3$): δ (ppm) 292.0, 261.8, 157.1, 148.4, 148.1, 142.6, 142.4, 142.1, 136.4, 130.1, 129.4, 129.2, 127.7, 126.3, 126.1, 125.4, 118.4, 113.4, 78.2, 77.4, 63.1, 48.3, 32.8, 29.0, 28.7, 28.3, 27.6, 27.3, 26.3, 24.5, 24.4, 22.5, 22.3.

CAAC (Me/1-Napht-dipp)-Ru Grela Type Complex
(Ru-2b)

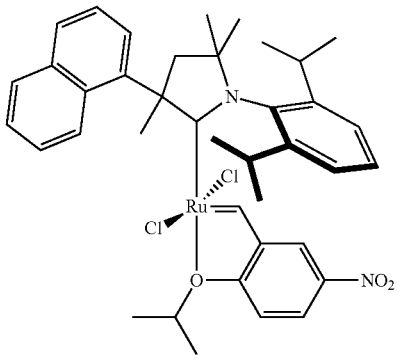

Chemical Formula: C$_{39}$H$_{46}$Cl$_2$N$_2$O$_3$Ru
Molecular Weight: 762.78

Ru-2b was prepared according to general procedure B for the synthesis of complexes with CAAC-2 (294 mg, 0.6 mmol, 1.9 equiv), Toluene (2.3 mL), KHMDS (1.3 mL, 0.65 mmol, 2.1 equiv) and Grela 1 complex (200 mg, 0.31 mmol, 1 equiv). The mixture was stirred 1 h. The desired product was obtained as a green solid (63 mg, 27% yield).

$^1$H NMR (400 MHz, CDCl$_3$): δ (ppm) 16.50 (s, 1H), 8.34 (dd, J=9.1, 2.7 Hz, 1H), 8.21 (d, J=8.6 Hz, 1H), 8.00 (d, J=7.3 Hz, 1H), 7.81 (dd, J=8.0, 1.6 Hz, 1H), 7.72 (d, J=8.1 Hz, 1H), 7.69-7.58 (m, 2H), 7.49-7.37 (m, 4H), 7.30 (t, J=7.7 Hz, 1H), 6.93 (d, J=9.1 Hz, 1H), 5.07 (sept, J=6.1 Hz, 1H), 3.52 (d, J=12.5 Hz, 1H), 3.35 (sept, J=6.7 Hz, 1H), 3.06 (s, 3H), 2.98 (sept, J=6.4 Hz, 1H), 2.49 (d, J=12.4 Hz, 1H), 1.62 (d, J=6.0 Hz, 3H), 1.51 (d, J=6.0 Hz, 3H), 1.25 (s, 3H), 1.18 (d, J=6.5 Hz, 3H), 1.15 (d, J=6.6 Hz, 3H), 0.99 (d, J=6.5 Hz, 3H), 0.83 (s, 3H), 0.53 (d, J=6.2 Hz, 3H).

$^{13}$C NMR (101 MHz, CDCl$_3$): δ (ppm) 288.7, 266.6, 156.2, 147.6, 147.3, 141.5, 141.5, 137.3, 135.4, 134.3, 129.4, 129.0, 129.0, 128.5, 128.0, 125.5, 125.4, 125.2, 124.4, 123.7, 123.6, 122.6, 117.5, 112.3, 78.7, 76.7, 63.6, 49.1, 29.9, 28.6, 27.9, 27.5, 26.3, 25.3, 24.9, 23.9, 22.7, 21.1, 20.6.

HRMS for C$_{39}$H$_{46}$N$_2$O$_3$$^{35}$Cl$_2$$^{102}$Ru (M$^+$·)$^+$): calc.: 762.19235, found: 762.1926 (0 ppm).

CAAC (Me/2-Napht-dipp)-Ru Grela Type Complex (Ru-3b)

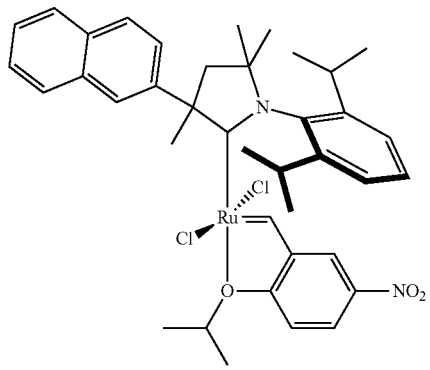

Chemical Formula: $C_{39}H_{46}Cl_2N_2O_3Ru$
Molecular Weight: 762.78

Ru-3b was prepared according to general procedure B for the synthesis of complexes with CAAC-3 (241 mg, 0.5 mmol, 2 equiv), Toluene (2 mL), KHMDS (1.1 mL, 0.55 mmol, 2.2 equiv), and Grela-1 complex (160 mg, 0.25 mmol, 1 equiv). The mixture was stirred 6 h at rt. The desired product was obtained after purification (eluent: Toluene) as a green solid (49 mg, 26% yield).

$^1$H NMR (400 MHz, CDCl$_3$): δ (ppm) 16.50 (s, 1H), 8.68 (d, J=2.0 Hz, 1H), 8.36 (dd, J=9.2, 2.7 Hz, 1H), 8.19 (dd, J=8.7, 2.1 Hz, 1H), 8.04-7.95 (m, 2H), 7.87 (dt, J=7.0, 3.7 Hz, 1H), 7.72 (t, J=7.7 Hz, 1H), 7.58 (d, J=2.7 Hz, 1H), 7.58-7.46 (m, 4H), 6.88 (d, J=9.2 Hz, 1H), 4.84 (sept, J=6.2 Hz, 1H), 3.28 (d, J=12.9 Hz, 1H), 3.15-2.98 (m, 2H), 2.48 (s, 3H), 1.56 (s, 3H), 1.48 (s, 3H), 1.37 (d, J=6.6 Hz, 3H), 1.33-1.23 (m, 7H), 0.98 (d, J=6.1 Hz, 3H), 0.87 (d, J=6.5 Hz, 3H), 0.52 (d, J=6.3 Hz, 3H).

$^{13}$C NMR (101 MHz, CDCl$_3$): δ (ppm) 291.5-291.2 (1C), 262.0, 157.0, 148.4, 148.0, 142.5, 142.5, 142.4, 138.8, 136.2, 133.5, 132.7, 130.0, 129.2, 128.8, 128.2, 128.0, 127.4, 126.2, 126.0, 125.9, 125.3, 118.2, 113.2, 78.4, 77.4, 62.9, 48.6, 32.7, 29.0, 28.7, 28.3, 27.3 (2C), 26.1, 24.4, 24.3, 21.7, 21.6.

HRMS for $C_{39}H_{46}N_2O^{35}Cl_2^{102}Ru$ (M$^{+\cdot}$): calc.: 762.19290, found: 762.1926 (0 ppm).

CAAC (Me/3,5-MePh-dipp)-Ru Grela Type Complex (Ru-4b)

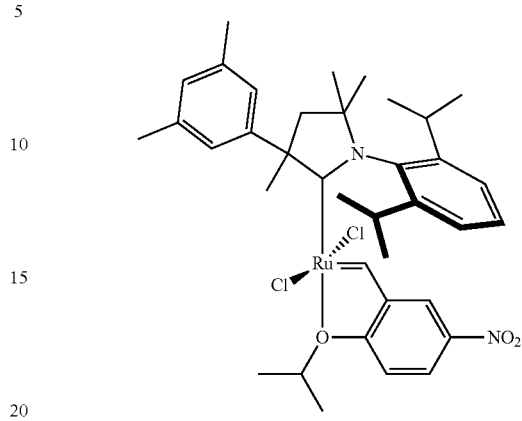

Chemical Formula: $C_{37}H_{48}Cl_2N_2O_3Ru$
Molecular Weight: 740.77

Ru-4b was prepared according to general procedure B for the synthesis of complexes with CAAC-4 (344 mg, 0.74 mmol, 2 equiv), Toluene (2.9 mL), KHMDS (1.5 mL, 0.75 mmol, 2 equiv) and Grela 1 complex (245 mg, 0.38 Ru mmol, 1 equiv). The mixture was stirred 2.5 h. The desired product was obtained as a green solid (125 mg, 44% yield).

$^1$H NMR (400 MHz, CDCl$_3$): δ (ppm) 16.52 (s, 1H), 8.40 (dd, J=9.1, 2.7 Hz, 1H), 7.84-7.46 (m, 6H), 7.12-6.89 (m, 2H), 5.03 (sept, J=6.1 Hz, 1H), 3.11-3.01 (m, 3H), 2.53-2.41 (m, 6H), 2.37 (s, 3H), 1.77-1.24 (m, 19H), 0.85 (d, J=6.4 Hz, 3H), 0.56 (d, J=6.2 Hz, 3H).

$^{13}$C NMR (101 MHz, CDCl$_3$): δ (ppm) 290.9, 262.4, 157.0, 148.5, 148.0, 142.5, 142.5 (2C), 140.3, 137.8 (2C), 136.2, 130.0, 129.2, 128.4 (2C), 126.2, 125.9, 125.2, 118.2, 113.2, 78.2, 62.5, 49.1, 32.6, 28.9, 28.7, 28.2, 27.3, 26.8, 26.1, 24.5, 24.2, 21.9 (3C), 21.8.

HRMS for $C_{37}H_{48}N_2O^{35}Cl_2^{102}Ru$ (M$^{+\cdot}$): calc.: 740.208, found: 740.2084 (0 ppm).

CAAC (Me/3,5-$^t$Bu$_2$Ph-dipp)-Ru Grela Type Complex (Ru-5b)

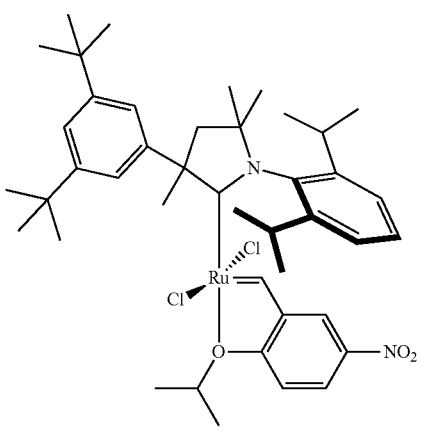

Chemical Formula: $C_{43}H_{60}Cl_2N_2O_3Ru$
Molecular Weight: 824.93

Ru-5b was prepared according to general procedure B for the synthesis of complexes with CAAC-5 (407 mg, 0.74 mmol, 3 equiv), Toluene (2 mL), KHMDS (1.1 mL, 0.55 mmol, 2.2 equiv), and Grela-1 complex (159 mg, 0.25 mmol, 1 equiv). The mixture was stirred 6 h at rt and 1 h at 40° C. The desired product was obtained after purification (eluent: Toluene) as a green solid (108 mg, 53% yield).

$^1$H NMR (400 MHz, CDCl$_3$): δ (ppm) 16.42 (s, 1H), 8.37 (dd, J=9.1, 2.7 Hz, 1H), 7.84 (d, J=1.7 Hz, 2H), 7.70 (t, J=7.7 Hz, 1H), 7.61 (d, J=2.7 Hz, 1H), 7.50 (ddd, J=16.8, 7.8, 1.7 Hz, 2H), 7.44 (t, J=1.6 Hz, 1H), 6.89 (d, J=9.2 Hz, 1H), 4.94 (sept, J=6.3 Hz, 1H), 3.17 (sept, J=6.8 Hz, 2H), 2.99 (d, J=13.1 Hz, 1H), 2.44 (d, J=13.1 Hz, 1H), 2.37 (s, 3H), 1.55-1.55-1.48 (m, 6H), 1.42 (s, 18H), 1.38-1.32 (m, 6H), 1.33-1.25 (d, J=6.6 Hz, 3H), 1.16 (d, J=6.2 Hz, 3H), 0.91-0.80 (d, J=6.5 Hz, 3H) 0.50 (d, J=6.3 Hz, 3H).

$^{13}$C NMR (101 MHz, CDCl$_3$): δ (ppm) 290.2-289.9 (1C), 263.1, 157.0, 149.0 (2C), 148.9, 148.1, 142.6, 142.5, 142.5, 137.4, 136.1, 129.9, 126.9 (2C), 126.3, 125.8, 125.0, 122.3, 118.0, 113.0, 78.1, 63.1, 51.6, 35.2 (2C), 33.5, 31.5 (6C), 29.1, 28.5, 28.1, 27.6, 26.0, 25.6, 24.6, 24.1, 22.0, 21.6.

HRMS for C$_{43}$H$_{60}$N$_2$O$_3$$^{35}$Cl$_2$$^{102}$Ru (M$^{+\cdot}$): calc.: 824.30245, found: 824.3020 (0 ppm).

CAAC (Me/Cy-dipp)-Ru Grela Type Complex
(Ru-6b)

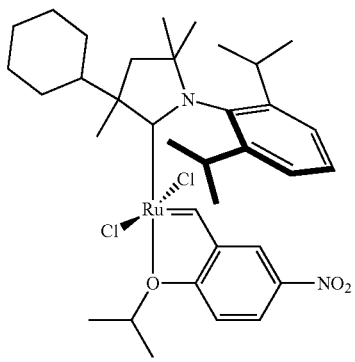

Chemical Formula: C$_{35}$H$_{50}$Cl$_2$N$_2$O$_3$Ru
Molecular Weight: 718.77

Ru-6b was prepared according to general procedure B for the complexes synthesis with CAAC-6 (150 mg, 0.34 mmol, 1.8 equiv), Toluene (1.2 mL), KHMDS (0.62 mL, 0.31 mmol, 1.6 equiv) and Grela 1 complex (124 mg, 0.19 mmol, 1 equiv). The mixture was stirred 1 h. The desired product was obtained as a green solid (40 mg, 29% yield).

$^1$H NMR (400 MHz, CDCl$_3$): δ (ppm) 16.64 (s, 1H), 8.42 (dd, J=9.2, 2.8 Hz, 1H), 7.72 (t, J=7.8 Hz, 1H), 7.55 (d, J=2.8 Hz, 1H), 7.53 (dd, J=7.8, 1.6 Hz, 1H), 7.50 (dd, J=7.8, 1.6 Hz, 1H), 7.04 (d, J=9.2 Hz, 1H), 5.16 (sept, J=6.2 Hz, 1H), 3.42 (d, J=11.5 Hz, 1H), 2.89 (sept, J=6.6 Hz, 1H), 2.78 (sept, J=6.4 Hz, 1H), 2.47-2.27 (m, 2H), 2.23-2.09 (m, 2H), 1.99 (d, J=12.7 Hz, 1H), 1.94-1.80 (m, 3H), 1.73 (m, 5H), 1.68 (d, J=6.1 Hz, 3H), 1.66 (s, 3H), 1.40 (m, 5H), 1.31 (d, J=6.6 Hz, 3H), 1.27-1.21 (m, 6H), 0.76 (d, J=6.4 Hz, 3H), 0.57 (d, J=6.4 Hz, 3H).

$^{13}$C NMR (101 MHz, CDCl$_3$): δ (ppm) 296.6, 264.4, 157.0, 147.8, 142.6, 137.0, 129.8, 126.1, 126.0, 125.6, 119.1, 113.5, 66.9, 50.9, 45.7, 39.7, 32.4, 28.8, 28.6, 28.2, 27.8, 27.3, 26.7, 26.6, 26.3, 25.7, 24.3, 22.7, 22.1, 19.3.

HRMS for C$_{35}$H$_{50}$N$_2$O$^{35}$Cl$_2$$^{102}$Ru (M$^{+\cdot}$): calc.: 718.22365, found: 718.2237 (0 ppm).

$^{Me/Ph}$CAAC (Me/Ph-dipp)-Ru Grela Type Complex
(Ru-7b)

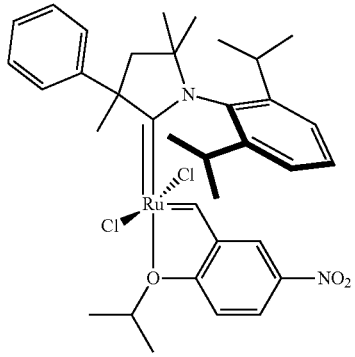

Chemical Formula: C$_{40}$H$_{46}$Cl$_2$N$_2$O$_3$Ru
Molecular Weight: 774.79

Ru-7b was prepared according to general procedure for the complexes synthesis with CAAC-7 (155 mg, 0.31 mmol, 1.6 equiv), Toluene (2 mL) and THF (1 mL), KHMDS (0.6 mL, 0.30 mmol, 1.5 equiv) and Grela 1 complex (126 mg, 0.20 mmol, 1 equiv). The mixture was stirred 3 h 30. The desired product was obtained after purification (eluent: Toluene) as a green solid (21.1 mg, 14% yield).

$^1$H NMR (400 MHz, CDCl$_3$): δ (ppm) 16.53 (d, J=0.8 Hz, 1H), 8.39 (dd, J=9.1, 2.7 Hz, 1H), 8.25-8.17 (m, 2H), 7.72 (t, J=7.7 Hz, 1H), 7.64-7.51 (m, 4H), 7.44-7.37 (m, 1H), 7.27-7.20 (m, 4H), 7.03 (d, J=7.2 Hz, 2H), 6.94 (d, J=9.1 Hz, 1H), 5.00 (sept, J=6.1 Hz, 1H), 3.51-3.46 (m, 1H), 3.35 (sept, J=6.5 Hz, 1H), 3.21 (d, J=14.1 Hz, 1H), 2.46 (s, 3H), 2.39 (sept, J=6.7 Hz, 1H), 1.90 (s, 3H), 1.47 (d, J=6.1 Hz, 3H), 1.43 (d, J=6.6 Hz, 3H), 1.33 (d, J=6.1 Hz, 3H), 0.59 (d, J=6.5 Hz, 3H), 0.57 (dd, J=6.5 Hz, 3H), −0.05 (d, J=6.6 Hz, 3H).

b. General Procedure for dep-CAAC Starting from M10 and Styrenyl Ether 1

Scheme S3 General procedure C

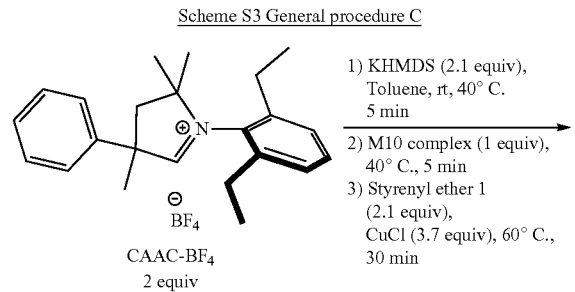

CAAC-BF$_4$
2 equiv

1) KHMDS (2.1 equiv), Toluene, rt, 40° C. 5 min
2) M10 complex (1 equiv), 40° C., 5 min
3) Styrenyl ether 1 (2.1 equiv), CuCl (3.7 equiv), 60° C., 30 min

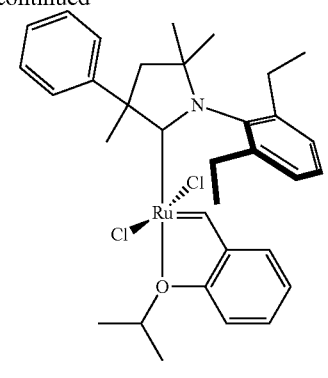

Ru-8 (83% yield)

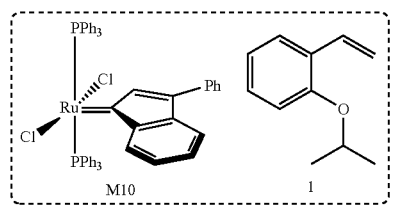

General Procedure C: In a glove box, CAAC·BF$_4$ (2 equiv) was dissolved in dry and degassed Toluene (10 mL/mmol Ru). KHMDS (0.5 M in toluene, 2.1 equiv) was added. The mixture was allowed to stirred 5 min at 40° C. Then, M10 complex (1 equiv) was then added. The mixture was stirred 5 min at 40° C. Styrenyl ether 1 (1.2 equiv) and CuCl (4 equiv) were added and the mixture was stirred 30 min at 60° C.

The solvent was removed under vacuum and the product was purified by column chromatography (eluent: Toluene). The solid was then diluted in the minimum amount of DCM and precipitated in pentane.

CAAC (Me/Ph-dep)-Ru Hoveyda Type Complex (Ru-8a)

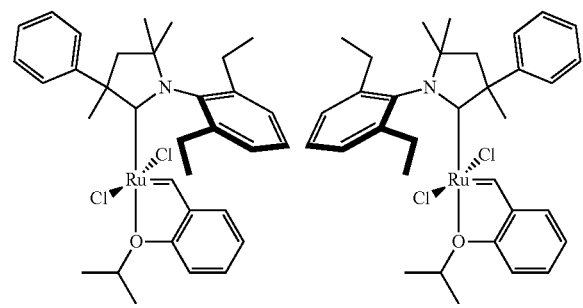

Chemical Formula: C$_{33}$H$_{41}$Cl$_2$NORu
Molecular Weight: 639.67

Ru-8a was prepared according to general procedure C for the complexes synthesis with CAAC-8 (395 mg, 0.97 mmol, 2.1 equiv), Toluene (4.0 mL), KHMDS (1.94 mL, 0.97 mmol, 2.1 equiv), M10 complex (430 mg, 0.46 mmol, 1 equiv), styrenyl ether 1 (157 mg, 0.97 mmol, 2.1 equiv) and CuCl (168 mg, 1.7 mmol, 3.7 equiv). The mixture was stirred 30 min at 60° C. The desired product was obtained after purification (eluent: Toluene) as a green solid (245 mg, 83% yield) as a mixture of conformers (ratio in toluene-d$_8$: 72:28).

$^1$H NMR (400 MHz, Toluene-d$_8$, 25° C.): δ (ppm) 17.76 (s, 0.28H), 16.40 (s, 0.72H), 8.27 (br s, 1H), 7.81 (br s, 1H), 7.46 (br s, 2H), 7.35-7.17 (m, 5H), 6.87 (d, J=7.5 Hz, 1H), 6.58 (br s, 1H), 6.38 (d, J=8.3 Hz, 1H), 4.52 (septet, J=6.2 Hz, 1H), 3.76-3.36 (m, 1H), 3.01-2.70 (m, 2H), 2.40 (m, 3H), 1.98-1.87 (m, 1H), 1.57-1.42 (m, 3H), 1.42-1.24 (m, 5H), 1.11 (br s, 3H), 1.03 (br s, J=9.9 Hz, 5H), 0.81 (m, J=6.4 Hz, 3H)

$^{13}$C NMR (101 MHz, CDCl$_3$, 25° C.): δ (ppm) 301.2, 263.6, 152.5, 144.3, 143.7, 143.5, 143.2, 138.8, 131.1, 129.4, 129.1, 128.8, 127.6, 127.2, 126.9, 123.9, 121.9, 113.4, 78.0, 74.7, 63.4, 48.5, 31.3, 28.0, 27.6, 25.8, 24.3, 22.5, 22.3, 14.9, 14.4.

CAAC (Me/1-Napht-dep)-Ru Hoveyda Type Complex (Ru-9a)

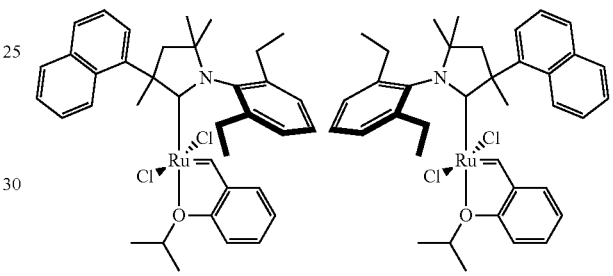

Chemical Formula: C$_{37}$H$_{43}$Cl$_2$NORu
Molecular Weight: 689.73

Ru-9a was prepared according to general procedure C for the complexes synthesis with CAAC-9 (554 mg, 1.21 mmol, 1.9 equiv), Toluene (4.0 mL), KHMDS (2.8 mL, 1.4 mmol, 2.2 equiv), M10 complex (612 mg, 0.65 mmol, 1 equiv), styrenyl ether 1 (136 mg, 0.83 mmol, 1.3 equiv) and CuCl (227 mg, 2.3 mmol, 3.5 equiv). The mixture was stirred 45 min at 60° C. The desired product was obtained after purification (eluent: Toluene) as a green solid (220.2 mg, 59% yield) as a mixture of conformers (ratio in CDCl$_3$: 5:95).

$^1$H NMR (400 MHz, CDCl$_3$): δ (ppm) 18.17 (s, 0.95H), 16.61 (br s, 0.05H), 8.50 (d, J=8.5 Hz, 1H), 8.40 (dd, J=7.4, 1.1 Hz, 1H), 8.01 (dd, J=8.1, 1.7 Hz, 1H), 7.83 (d, J=8.1 Hz, 1H), 7.65-7.57 (m, 3H), 7.49-7.44 (m, 2H), 7.41 (dd, J=7.1, 2.2 Hz, 1H), 7.33-7.25 (m, 2H), 6.95 (d, J=8.4 Hz, 1H), 6.89 (t, J=7.5 Hz, 1H), 5.06 (sept, J=6.1 Hz, 1H), 3.52-3.30 (m, 2H), 3.25-3.15 (m, 1H), 2.83-2.60 (m, 3H), 2.40 (s, 3H), 1.48 (d, J=6.1 Hz, 3H), 1.34-1.43 (m, 9H), 1.26 (t, J=7.5 Hz, 3H), 1.10 (s, 3H).

$^{13}$C NMR (101 MHz, CDCl$_3$): δ (ppm) 297.5-295.9 (1C), 273.2, 153.9, 145.7, 144.3, 143.9, 143.0, 137.9, 135.5, 131.1, 130.4, 130.2, 129.3, 128.4, 127.7, 127.6, 127.4, 126.2, 125.4, 125.3, 125.1, 123.6, 122.1, 113.4, 76.0, 75.0, 63.6, 55.4, 30.5, 29.1, 28.7, 27.9, 27.6, 21.8, 21.5, 15.9, 15.4.

HRMS for C$_{37}$H$_{43}$NO$^{35}$Cl$_2$$^{102}$Ru (M$^+$): calc.: 689.17597, found: 689.1762 (0 ppm).

CAAC (Me/1-Napht-dep)-Ru Hoveyda Type Complex (Ru-10a)

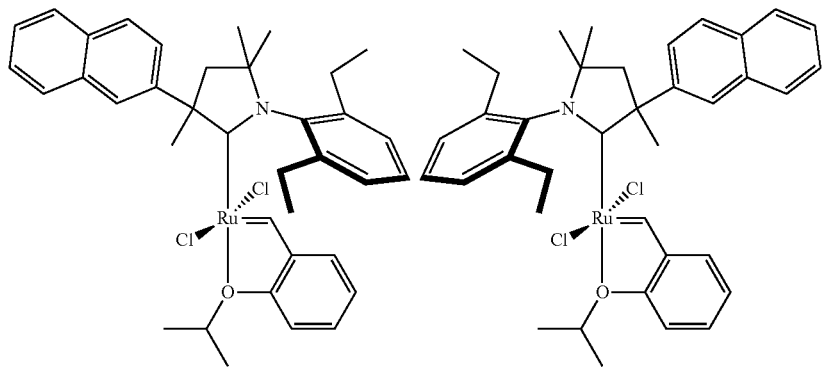

Chemical Formula: $C_{37}H_{43}Cl_2NORu$
Molecular Weight: 689.73

Ru-10a was prepared according to general procedure C for the complexes synthesis with CAAC-10 (640.2 mg, 1.4 mmol, 1.9 equiv), Toluene (5.6 mL), KHMDS (2.8 mL, 1.4 mmol, 1.9 equiv), M10 complex (684 mg, 0.73 mmol, 1 equiv), styrenyl ether 1 (144 mg, 0.89 mmol, 1.2 equiv) and CuCl (249 mg, 2.5 mmol, 3.4 equiv). The mixture was stirred 45 min at 60° C. The desired product was obtained after purification (eluent: Toluene) as a green solid (335 mg, 66% yield) as a mixture of conformers (ratio in $CDCl_3$: 75:25).

$^1$H NMR (400 MHz, $CDCl_3$): δ (ppm) 17.96 (s, 0.25H), 16.31 (s, 0.75H), 8.52 (br s, 0.75H), 8.27 (d, J=7.1 Hz, 1H), 7.96 (d, J=6.9 Hz, 0.25H), 7.94-7.92 (m, 0.75H), 7.83-7.75 (m, 1H), 7.68 (d, J=6.9 Hz, 0.25H), 7.54 (t, J=6.1 Hz, 0.75H), 7.47-7.35 (m, 5H), 7.20 (s, 1H), 6.83 (d, J=6.6 Hz, 0.25H), 6.75-6.71 (m, 2H), 6.69-6.66 (m, 0.75H), 5.02-4.92 (m, 0.25H), 4.74 (sept, J=4.9 Hz, 0.75H), 3.28-3.14 (m, 1.25H), 2.78-2.35 (m, 7H), 1.98 (s, 0.75H), 1.60 (s, 0.25H), 1.49 (br. s, 2H), 1.41-1.14 (m, 8H), 1.04-0.93 (m, 5H), 0.75 (t, J=5.9 Hz, 3H).

$^{13}$C NMR (101 MHz, $CDCl_3$): δ (ppm) 301.6, 263.1, 152.3, 144.0, 143.4, 143.3, 142.4, 139.9, 138.5, 133.5, 132.5, 131.3, 129.3, 129.1, 128.8, 128.4, 128.1, 127.8, 127.6, 127.2, 126.8, 126.2, 126.0, 124.0, 123.7, 122.1, 121.9, 113.4, 78.4, 75.9, 74.9, 74.6, 63.2, 48.5, 31.3, 27.6, 25.8, 28.1, 24.2, 21.9, 21.8, 21.7, 21.3, 15.2, 14.6.

HRMS for $C_{37}H_{43}NO^{35}Cl_2{}^{102}Ru$ (M$^+$): calc.: 689.16032, found: 689.1762 (0 ppm).

CAAC (Me/1-Napht-dep)-Ru Hoveyda Type Complex (Ru-11a)

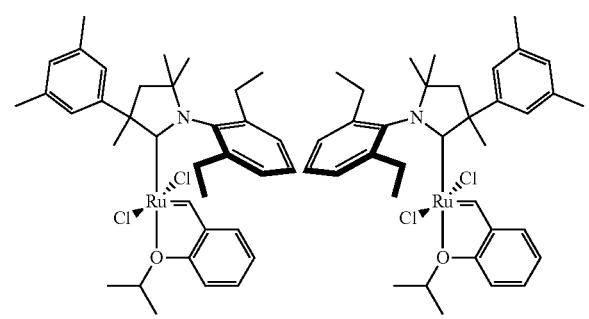

Chemical Formula: $C_{35}H_{45}Cl_2NORu$
Molecular Weight: 667.72

Ru-11a was prepared according to general procedure C for the complexes synthesis with CAAC-11 (634 mg, 1.45 mmol, 2.1 equiv), Toluene (5.6 mL), KHMDS (2.8 mL, 1.4 mmol, 2 equiv), M10 complex (646 mg, 0.69 mmol, 1 equiv), styrenyl ether 1 (140 mg, 0.86 mmol, 1.2 equiv) and CuCl (244 mg, 2.5 mmol, 3.7 equiv). The mixture was stirred 45 min at 60° C. The desired product was obtained after purification (eluent: Toluene) as a green solid (266 mg, 58% yield) as a mixture of conformers (ratio in $CDCl_3$: 33:67).

¹H NMR (400 MHz, CDCl₃): δ (ppm) 17.89 (s, 0.33H), 16.36 (s, 0.67H), 8.52 (br s, 1H), 7.61-7.51 (m, 1H), 7.50-7.33 (m, 3H), 7.30-7.26 (m, 1H), 7.19 (d, J=6.4 Hz, 0.33H), 7.01 (br s, 0.67H), 6.94-6.87 (m, 1H), 6.84-6.78 (m, 1.33H), 6.76-6.72 (m, 0.67H), 5.01 (sept, J=4.8 Hz, 0.33H), 4.92 (sept, J=4.9 Hz, 0.67H), 3.32-3.12 (m, 0.67H), 3.07 (d, J=10.3 Hz, 0.67H), 2.80 (sept, J=6.0 Hz, 0.33H), 2.73-2.55 (m, 2H), 2.51 (sept, J=6.0 Hz, 1.33H), 2.43 (br s, 4H), 2.38-2.32 (m, 3H), 2.29-2.12 (br m, 1H), 1.90 (br. s, 1H), 1.68 (br s, 1H), 1.49 (br s, 2H), 1.46-1.36 (m, 5H), 1.35-1.21 (m, 5H), 1.18 (br s, 1H), 1.03 (t, J=5.9 Hz, 2H), 0.87 (t, J=5.5 Hz, 1H), 0.82 (t, J=5.9 Hz, 2H).

¹³C NMR (101 MHz, CDCl₃, 25° C.): δ (ppm) 300.6, 297.6, 271.9, 263.2, 153.3, 152.1, 149.4, 145.6, 144.0, 143.9, 143.4, 142.1, 140.9, 138.4, 138.1, 138.0, 137.7, 131.0, 129.2, 128.9, 127.7, 127.3, 127.2, 127.0, 126.7, 123.9, 123.5, 122.0, 121.8, 113.2, 78.1, 75.7, 74.7, 74.5, 63.4, 62.4, 57.2, 49.2, 34.2, 31.3, 30.1, 28.7, 28.1, 27.6, 27.3, 25.7, 24.1, 22.6, 22.1, 21.9, 21.7, 21.6, 21.4, 16.4, 15.2, 14.9, 14.5, 14.3.

HRMS for $C_{35}H_{45}NO^{35}Cl_2^{102}Ru$ (M+.): calc.: 667.19162, found: 667.1917 (0 ppm).

c. General Procedure for dep-CAAC Starting from M10 and Styrenyl Ether 2

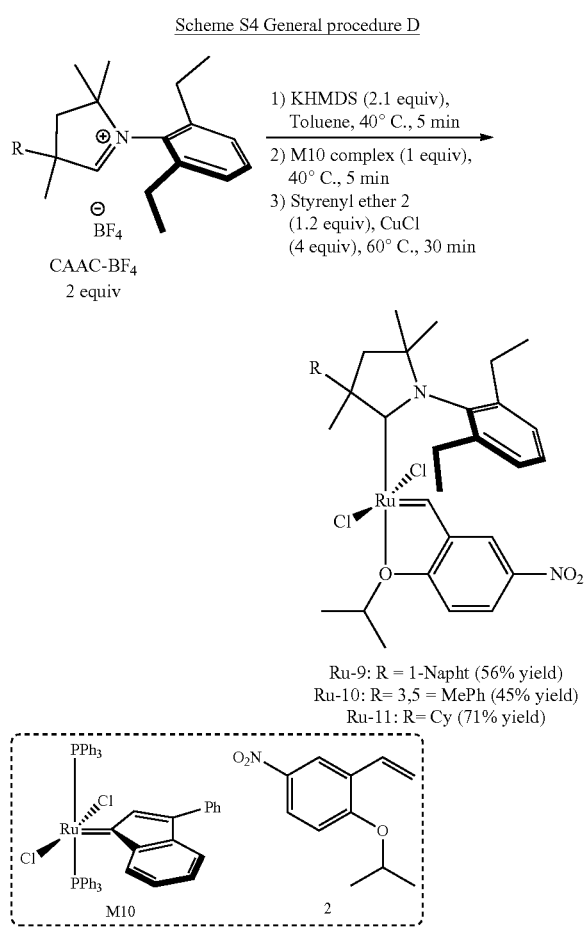

Ru-9: R = 1-Napht (56% yield)
Ru-10: R= 3,5 - MePh (45% yield)
Ru-11: R= Cy (71% yield)

General Procedure D: In a glove box, CAAC·BF₄ (2 equiv) was dissolved in dry and degassed Toluene (10 mL/mmol Ru). KHMDS (0.5 M in toluene, 2.1 equiv) was added. The mixture was allowed to stirred 5 min at 40° C. Then, M10 complex (1 equiv) was then added. The mixture was stirred 5 min at 40° C. Styrenyl ether 1 (1.2 equiv) and CuCl (4 equiv) were added and the mixture was stirred 30 min at 60° C.

The solvent was removed under vacuum and the product was purified by column chromatography (eluent: Toluene). The solid was then diluted in the minimum amount of DCM and precipitated in pentane.

CAAC (Me/Ph-dep)-Ru Grela Type Complex (Ru-8b)

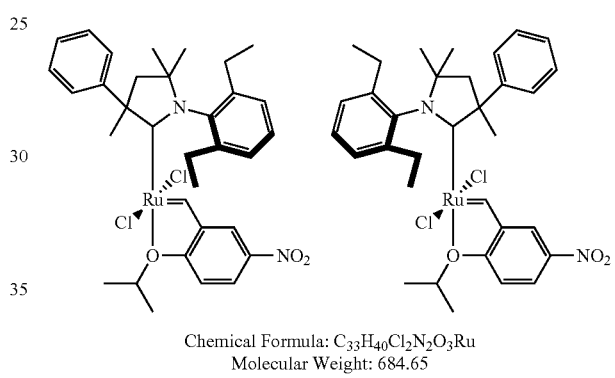

Chemical Formula: $C_{33}H_{40}Cl_2N_2O_3Ru$
Molecular Weight: 684.65

Ru-8b was prepared according to general procedure D for the complexes synthesis with CAAC-8 (514 mg, 1.26 mmol, 1.9 equiv), Toluene (7.0 mL), KHMDS (2.5 mL, 1.25 mmol, 1.9 equiv), M10 complex (625 mg, 0.66 mmol, 1 equiv), styrenyl ether 2 (165 mg, 0.8 mmol, 1.2 equiv) and CuCl (290 mg, 2.93 mmol, 4.4 equiv). The mixture was stirred 1.5 h at 60° C. The desired product was obtained after purification (eluent: Toluene) as a green solid (327 mg, 72% yield) as a mixture of conformers (ratio in CDCl₃: 76:24).

¹H NMR (400 MHz, CDCl₃): δ (ppm) 17.77 (s, 0.24H), 16.44 (s, 0.76H), 8.50-8.33 (m, 1H), 8.21 (s, 1H), 7.76-7.28 (m, 8H), 6.96 (d, J=9.1 Hz, 1H), 5.03 (p, J=6.5 Hz, 1H), 3.15 (s, 1H), 2.70 (s, 2H), 2.52 (s, 2H), 2.45-2.22 (m, 3H), 2.01 (br s, 1H), 1.53-1.25 (m, 10H), 1.09 (s, 3H), 0.84 (s, 3H).

¹³C NMR (101 MHz, CDCl₃): δ (ppm) 295.0, 260.6, 156.5, 143.5, 143.1, 142.7, 138.2, 132.1, 129.5, 129.4, 128.7, 128.5, 127.7, 127.4, 127.1, 125.4, 118.2, 113.2, 63.2, 48.4, 31.1, 29.7, 27.6, 25.6, 24.2, 22.2, 14.8, 14.3.

CAAC (Me/1-Napht-dep)-Ru Hoveyda Type Complex (Ru-9b)

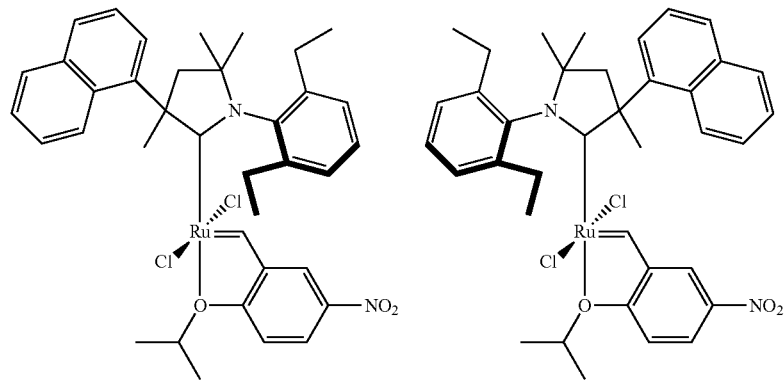

Chemical Formula: $C_{37}H_{42}Cl_2N_2O_3Ru$
Molecular Weight: 734.72

Ru-9b was prepared according to general procedure D for the complexes synthesis with CAAC-9 (402 mg, 0.88 mmol, 2.1 equiv), Toluene (3.9 mL), KHMDS (1.8 mL, 0.90 mmol, 2.1 equiv), M10 complex (390.5 mg, 0.42 mmol, 1 equiv), styrenyl ether 2 (105 mg, 0.51 mmol, 1.2 equiv) and CuCl (153 mg, 1.54 mmol, 3.7 equiv). The mixture was stirred 30 min at 60° C. The desired product was obtained after purification (eluent: Toluene) as a green solid (16.1 mg, 6% yield) as a mixture of conformers (ratio in $CDCl_3$: 5:95).

$^1$H NMR (400 MHz, $CDCl_3$): δ (ppm) 18.25 (s, 0.95H), 16.61 (s, 0.05H), 8.56-8.45 (m, 2H), 8.29 (d, J=7.4, 1H), 8.19 (d, J=2.6 Hz, 1H), 8.03 (d, J=7.9, 1H), 7.86 (d, J=8.1 Hz, 1H), 7.70-7.58 (m, 2H), 7.56-7.39 (m, 3H), 7.29 (t, J=8.2, 1H), 7.04 (d, J=9.2 Hz, 1H), 5.14 (sept, J=6.1 Hz, 1H), 3.47-3.33 (m, 2H), 3.19 (dq, J=15.2, 7.6 Hz, 1H), 2.74-2.61 (m, 3H), 2.37 (s, 3H), 1.50 (d, J=6.1, 3H), 1.43 (d, J=6.1 Hz, 3H), 1.40-1.35 (m, 6H), 1.31-1.24 (m, 3H), 1.14 (s, 3H).

$^{13}$C NMR (101 MHz, $CDCl_3$): δ (ppm) 291.7, 270.0, 157.8, 145.5, 143.4, 143.3, 142.8, 142.7, 137.5, 135.5, 130.3, 130.2, 129.5, 129.5, 128.7, 127.6, 127.4, 127.2, 125.8, 125.3, 125.2, 124.8, 118.1, 113.2, 63.5, 55.2, 30.5, 29.7, 28.9, 28.7, 27.9, 27.5, 21.6, 21.4, 15.8, 15.4.

HRMS: for $C_{37}H_{42}N_2O_3{}^{35}Cl_2{}^{102}Ru$ (M$^{+\cdot}$): calc.: 734.16105, found: 734.1610 (0 ppm).

CAAC (Me/2-Napht-dep)-Ru Hoveyda Type Complex (Ru-10b)

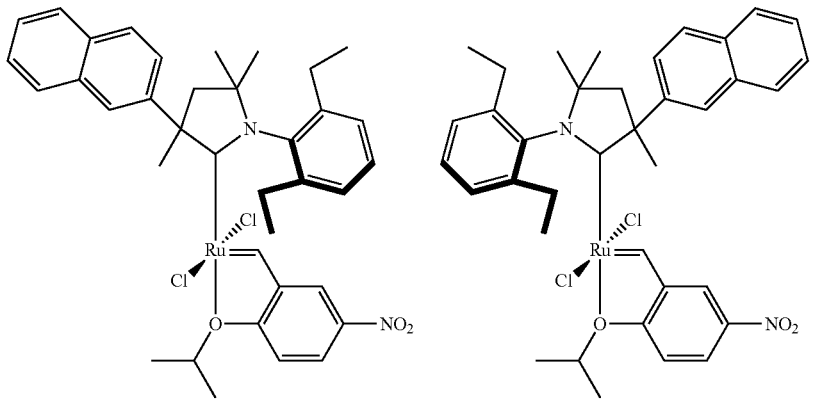

Chemical Formula: $C_{37}H_{42}Cl_2N_2O_3Ru$
Molecular Weight: 734.72

Ru-10b was prepared according to general procedure D for the complexes synthesis with CAAC-10 (366 mg, 0.80 mmol, 2.1 equiv), Toluene (3.5 mL), KHMDS (1.6 mL, 0.80 mmol, 2.1 equiv), M10 complex (355 mg, 0.38 mmol, 1 equiv), styrenyl ether 2 (88 mg, 0.42 mmol, 1.1 equiv) and CuCl (139 mg, 1.4 mmol, 3.7 equiv). The mixture was stirred 30 min at 60° C. The desired product was obtained after purification (eluent: Toluene) as a green solid (157 mg, 56% yield) as a mixture of conformers (ratio in CDCl$_3$: 72:28).

$^1$H NMR (400 MHz, CDCl$_3$): δ (ppm) 17.98 (s, 0.28H), 16.44 (s, 0.72H), 8.71-8.12 (m, 3H), 8.02-7.81 (m, 3H), 7.60 (m, J=61.7, 13.7 Hz, 6H), 6.90 (m, J=9.3 Hz, 1H), 4.99 (m, J=84.4 Hz, 1H), 3.44-3.14 (m, 1H), 2.75 (br s, 2H), 2.65-2.48 (m, 4H), 2.25-1.97 (m, 1H), 1.44 (m, 13H), 1.09 (m, 4H), 0.89 (br s, 2H).

$^{13}$C NMR (101 MHz, CDCl$_3$): δ (ppm) 294.7, 260.9, 156.6, 143.6, 143.4, 142.7, 139.3, 138.2, 133.6, 132.8, 129.6, 128.8, 128.6, 128.3, 128.0, 127.6, 127.5, 127.3, 127.2, 126.3, 126.1, 125.4, 118.2, 113.3, 78.9, 63.2, 49.1, 32.8, 31.7, 31.3, 29.8, 27.8, 27.4, 26.6, 26.3, 25.8, 24.4, 22.8, 21.9, 21.7, 15.0, 14.4, 14.2.

HRMS: for C$_{37}$H$_{42}$N$_2$O$_3$$^{35}$Cl$_2$$^{102}$Ru (M$^+$): calc.: 734.16105, found: 734.1613 (0 ppm).

CAAC (Me/3,5-MePh-dep)-Ru Grela Type Complex (Ru-11b)

Ru-11b was prepared according to general procedure D for the complexes synthesis with CAAC-11 (744 mg, 1.71 mmol, 2 equiv), Toluene (6.8 mL), KHMDS (3.4 mL, 1.7 mmol, 2 equiv), M10 complex (800 mg, 0.86 mmol, 1 equiv), styrenyl ether 2 (219 mg, 1.06 mmol, 1.2 equiv) and CuCl (308 mg, 3.1 mmol, 3.6 equiv). The mixture was stirred 30 min at 60° C. The desired product was obtained after purification (eluent: Toluene) as a green solid (436 mg, 71% yield) as a mixture of conformers (ratio in CDCl$_3$: 67:33).

$^1$H NMR (400 MHz, CDCl$_3$): δ (ppm) 17.94 (s, 0.33H), 16.44 (s, 0.67H), 8.58-8.33 (m, 1H), 7.66 (br s, 3H), 7.49 (br s, 3H), 6.99 (m, 2H), 5.04 (br s, 1H), 3.19 (m, 1H), 2.65 (m, 4H), 2.46-2.30 (m, 8H), 1.94 (m, 1H), 1.55-1.40 (m, 9H), 1.40-1.34 (m, 2H), 1.30 (m, 3H), 1.10 (s, 2H), 0.91 (m, 3H).

$^{13}$C NMR (101 MHz, CDCl$_3$): δ (ppm) 293.7, 261.1, 156.6, 143.7, 143.4, 142.8, 140.5, 138.2, 129.5, 128.0, 127.4, 127.1, 125.3, 124.8, 118.2, 113.2, 78.7, 63.7, 62.6, 57.7, 50.0, 31.3, 30.3, 28.3, 27.8, 26.7, 25.8, 24.4, 21.9, 16.1, 15.0, 14.4.

HRMS for C$_{35}$H$_{44}$N$_2$O$^{35}$Cl$_2$$^{102}$Ru (M$^+$): calc.: 712.1767, found: 712.1766 (0 ppm).

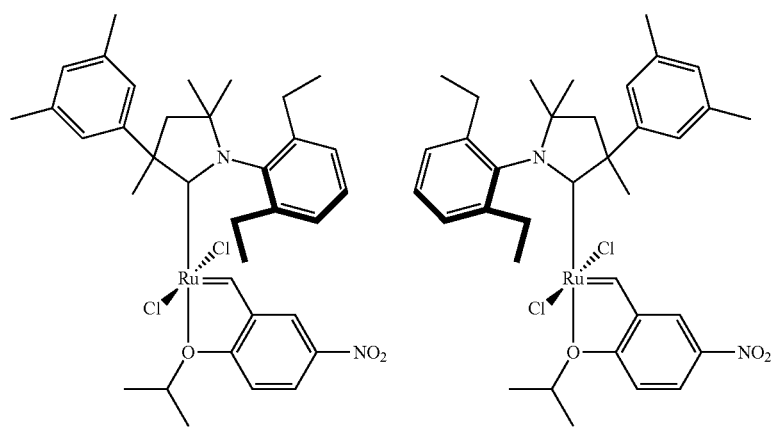

Chemical Formula: C$_{35}$H$_{44}$Cl$_2$N$_2$O$_3$Ru
Molecular Weight: 712.72

CAAC (Me/Cy-dep)-Ru Grela Type Complex (Ru-12b)

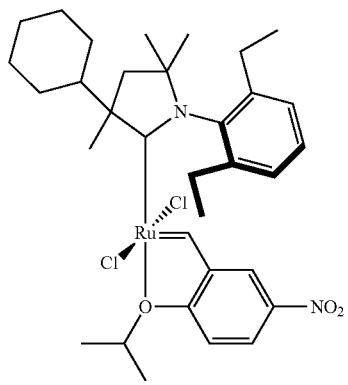

Chemical Formula: C$_{33}$H$_{46}$Cl$_2$N$_2$O$_3$Ru
Molecular Weight: 690.71

Ru-12b was prepared according to general procedure D for the complexes synthesis with CAAC-12 (314 mg, 0.76 mmol, 2.0 equiv), Toluene (3.5 mL), KHMDS (1.6 mL, 0.80 mmol, 2.1 equiv), M10 complex (355 mg, 0.38 mmol, 1 equiv), styrenyl ether 2 (88 mg, 0.42 mmol, 1.1 equiv) and CuCl (139 mg, 1.4 mmol, 3.7 equiv). The mixture was stirred 30 min at 60° C. The desired product was obtained after purification (eluent: Toluene) as a green solid (185 mg, 71% yield).

$^1$H NMR (400 MHz, CDCl$_3$): δ (ppm) 16.47 (d, J=0.7 Hz, 1H), 8.44 (dd, J=9.1, 2.8 Hz, 1H), 7.69 (t, J=7.7 Hz, 1H), 7.62 (d, J=2.7 Hz, 1H), 7.50 (td, J=8.0, 1.5 Hz, 2H), 7.08-7.01 (m, 1H), 5.15 (hept, J=6.2 Hz, 1H), 3.40-3.28 (m, 1H), 2.58 (q, J=7.7 Hz, 2H), 2.43 (q, J=7.5 Hz, 2H), 2.37-2.27 (m, 2H), 2.25-2.09 (m, 2H), 1.98 (d, J=12.7 Hz, 1H), 1.93-1.81 (m, 2H), 1.69 (d, J=5.7 Hz, 8H), 1.64 (d, J=6.1 Hz, 3H), 1.47-1.33 (m, 6H), 1.21 (s, 3H), 1.01 (t, J=7.4 Hz, 3H), 0.86 (t, J=7.4 Hz, 3H).

$^{13}$C NMR (101 MHz, CDCl$_3$): δ (ppm) 300.6, 263.6, 156.5, 144.0, 144.0, 143.2, 142.8, 142.8, 139.1, 129.4, 127.2, 127.1, 125.8, 119.0, 113.5, 77.8, 77.2, 67.1, 51.0, 45.6, 39.6, 30.4, 27.7, 26.7, 26.4, 25.8, 25.5, 24.2, 22.7, 22.2, 19.4, 14.7, 14.4.

HRMS for C$_{33}$H$_{46}$N$_2$O$^{35}$Cl$_2$$^{102}$Ru (M$^{+\cdot}$): calc.: 690.19235, found: 690.1925 (0 ppm).

CAAC (Me/CH$_2$pCymene-dep)-Ru Grela Type Complex (Ru-13b)

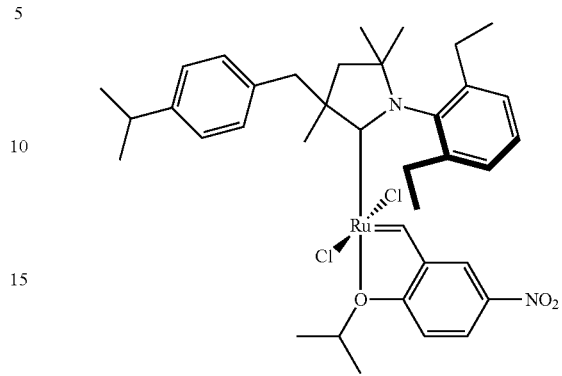

Chemical Formula: C$_{37}$H$_{48}$Cl$_2$N$_2$O$_3$Ru
Molecular Weight: 740.77

Ru-13b was prepared according to general procedure D for the complexes synthesis with CAAC-13 (110 mg, 0.24 mmol, 2.0 equiv), Toluene (1.5 mL), KHMDS (1.6 mL, 0.80 mmol, 1.7 equiv), M10 complex (150 mg, 0.14 mmol, 1 equiv), styrenyl ether 2 (28 mg, 0.13 mmol, 0.9 equiv) and CuCl (37 mg, 0.38 mmol, 2.7 equiv). The mixture was stirred 2 h at 60° C. The desired product was obtained after purification (eluent: Toluene) as a green solid (70 mg, 88% yield).

$^1$H NMR (400 MHz, CDCl$_3$): δ (ppm) 16.39 (s, 1H), 8.50 (dd, J=9.1, 2.7 Hz, 1H), 7.75 (d, J=2.7 Hz, 1H), 7.71 (t, J=7.7 Hz, 1H), 7.53 (d, J=7.8 Hz, 2H), 7.39-7.32 (m, 2H), 7.26 (d, J=8.1 Hz, 2H), 7.08 (d, J=9.1 Hz, 1H), 5.29 (sept, J=6.1 Hz, 1H), 4.37 (d, J=12.7 Hz, 1H), 3.89 (d, J=12.7 Hz, 1H), 2.96 (sept, J=6.9 Hz, 1H), 2.74-2.51 (m, 5H), 2.00-1.90 (m, 4H), 1.84 (d, J=6.1 Hz, 6H), 1.40 (s, 3H), 1.36 (s, 3H), 1.32 (d, J=6.9 Hz, 6H), 1.02 (t, J=7.4 Hz, 3H), 0.94 (t, J=7.4 Hz, 3H).

$^{13}$C NMR (101 MHz, CDCl$_3$): δ (ppm) 291.6-291.5 (1C), 263.3, 156.6, 147.2, 143.3, 143.2, 143.2, 142.8, 138.1, 135.0, 130.8 (2C), 129.5, 127.2, 127.2, 126.2 (2C), 125.4, 118.1, 113.1, 79.0, 77.7, 61.0, 48.6, 46.8, 33.8, 29.7, 27.7, 25.4, 25.3, 24.4, 24.1, 24.1, 22.2, 22.0, 14.7, 14.4.

CAAC (Me/Ph-mipp)-Ru Grela Type Complex (Ru-14b)

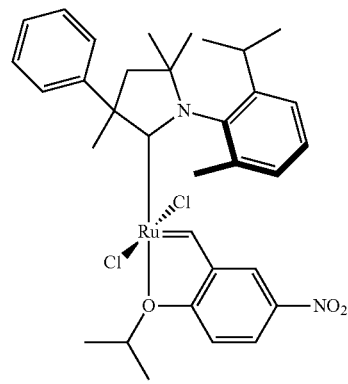

Chemical Formula: C$_{33}$H$_{40}$Cl$_2$N$_2$O$_3$Ru
Molecular Weight: 684.66

Ru-14b was prepared according to general procedure D for the complexes synthesis with CAAC-14 (195 mg, 0.48 mmol, 2.1 equiv), Toluene (3 mL), KHMDS (0.9 mL, 0.45 mmol, 2.0 equiv), M10 complex (245 mg, 0.23 mmol, 1 equiv), styrenyl ether 2 (52 mg, 0.25 mmol, 1.1 equiv) and CuCl (77 mg, 0.78 mmol, 3.4 equiv). The mixture was stirred 1 h at 60° C. The desired product was obtained after purification (eluent: Toluene) as a green solid (91 mg, 58% yield) as 2 diastereoisomers (40/60 ratio).

$^1$H NMR (400 MHz, CDCl$_3$): δ (ppm) 16.42 (s, 0.4H), 16.38 (s, 0.6H), 8.47-8.39 (m, 1H), 8.28-8.19 (m, 2H), 7.73-7.63 (m, 2H), 7.63-7.53 (m, 3H), 7.53-7.36 (m, 2H), 6.98 (t, J=9.0 Hz, 1H), 5.06 (2sept, J=6.2 Hz, 1H), 3.23 (d, J=12.9 Hz, 0.6H), 3.19-3.05 (m, 1H), 3.05-2.93 (m, 0.4H), 2.49-2.41 (m, 5H), 2.36 (s, 1.8H), 2.28 (s, 1.2H), 1.67 (s, 1.8H), 1.61 (d+s, J=6.7 Hz, 2.4H), 1.56 (d, J=6.1 Hz, 1.8H), 1.54-1.46 (m, 5H), 1.41 (t, J=6.1 Hz, 3H), 1.32 (d, J=6.7 Hz, 1.8H), 0.90 (d, J=6.5 Hz, 1.2H).

d. General Procedure for dipp-CAAC starting from Grubbs 3$^{rd}$ G. and Styrenyl Ether 3 mL/mmol Ru). KHMDS (1.2 equiv) was added. The mixture was allowed to stir 30 min at RT. Then, the resulting slurry was filtered through glass fibre filter and Grubbs 3 complex (1 equiv) was then added. The mixture was stirred overnight at RT. The resulting mixture was then added dropwise into a flask containing precooled pentane, resulting into a formation of green precipitate. The precipitation was then pursued until the supernatant become red. The supernatant was then removed and the solid was washed twice with pentane. The complex was dried in vacuo and Styrenyl ether 3 (1.2 equiv) and Toluene (10 mL/mmol Ru) were added and the mixture was stirred overnight at 60° C.

The solvent was removed under vacuum and the product was purified by column chromatography (eluent: Toluene). The solid was then diluted in the minimum amount of DCM and precipitated in pentane.

CAAC (Me/Cy-dipp)-Ru Blechert Type Complex (Ru-6c)

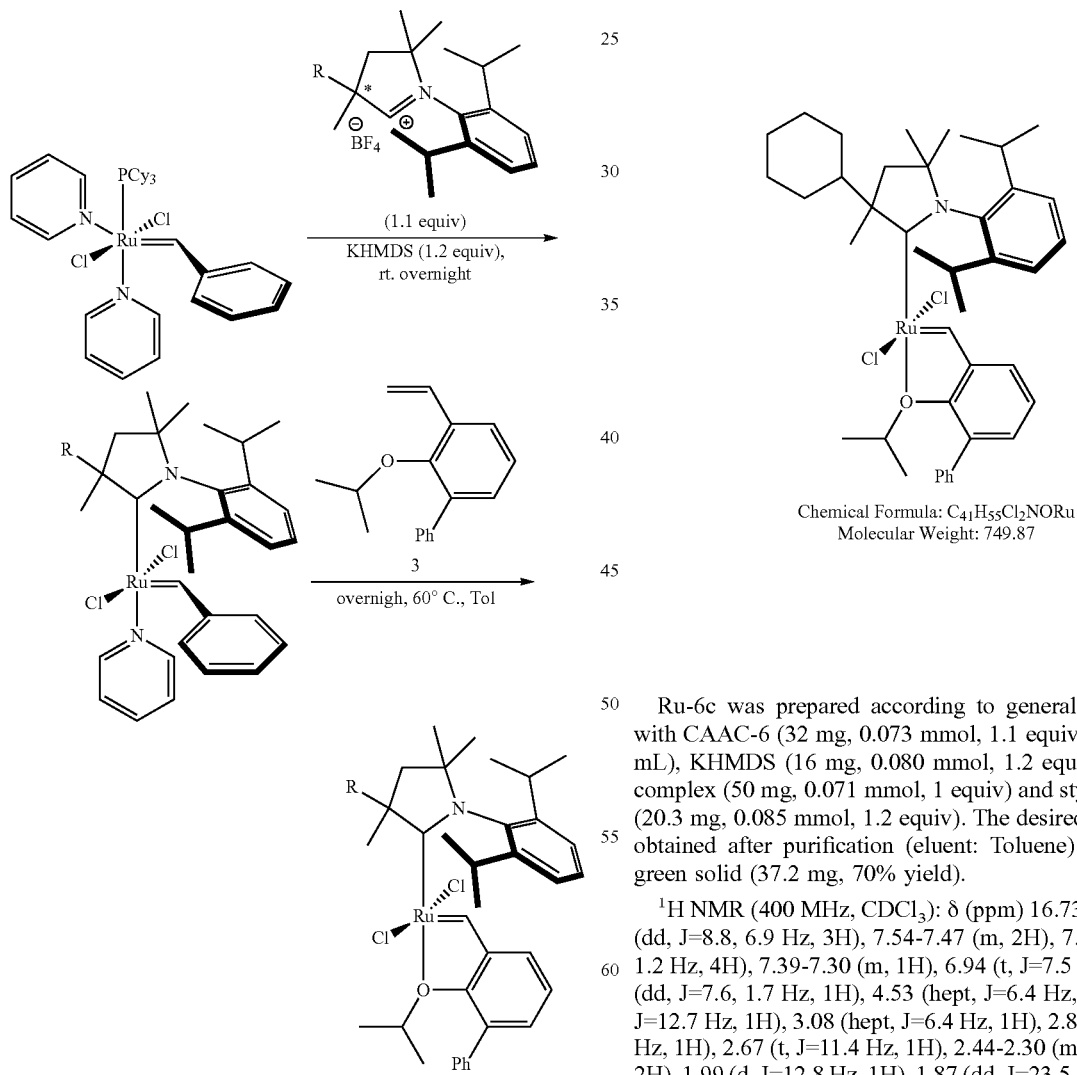

Chemical Formula: C$_{41}$H$_{55}$Cl$_2$NORu
Molecular Weight: 749.87

Ru-6c was prepared according to general procedure E with CAAC-6 (32 mg, 0.073 mmol, 1.1 equiv), Benzene (2 mL), KHMDS (16 mg, 0.080 mmol, 1.2 equiv), Grubbs 3 complex (50 mg, 0.071 mmol, 1 equiv) and styrenyl ether 3 (20.3 mg, 0.085 mmol, 1.2 equiv). The desired product was obtained after purification (eluent: Toluene) as a purple-green solid (37.2 mg, 70% yield).

$^1$H NMR (400 MHz, CDCl$_3$): δ (ppm) 16.73 (s, 1H), 7.66 (dd, J=8.8, 6.9 Hz, 3H), 7.54-7.47 (m, 2H), 7.44 (td, J=7.8, 1.2 Hz, 4H), 7.39-7.30 (m, 1H), 6.94 (t, J=7.5 Hz, 1H), 6.68 (dd, J=7.6, 1.7 Hz, 1H), 4.53 (hept, J=6.4 Hz, 1H), 3.44 (d, J=12.7 Hz, 1H), 3.08 (hept, J=6.4 Hz, 1H), 2.82 (hept, J=6.6 Hz, 1H), 2.67 (t, J=11.4 Hz, 1H), 2.44-2.30 (m, 1H), 2.21 (s, 2H), 1.99 (d, J=12.8 Hz, 1H), 1.87 (dd, J=23.5, 11.6 Hz, 2H), 1.77 (s, 3H), 1.61 (s, 3H), 1.38 (s, 3H), 1.31 (d, J=2.5 Hz, 2H), 1.29-1.27 (m, 7H), 1.26 (d, J=6.3 Hz, 4H), 1.03 (d, J=6.3 Hz, 3H), 0.73 (t, J=6.2 Hz, 7H).

General Procedure E: In a glove box, CAAC·BF$_4$ (1.1 equiv) was dissolved in dry and degassed Toluene (10 e. General Procedure for dep-CAAC Starting from Grubbs 3rd G. and Styrenyl Ether 3

CAAC (Me/Cy-dep)-Ru Blechert Type Complex (Ru-12c)

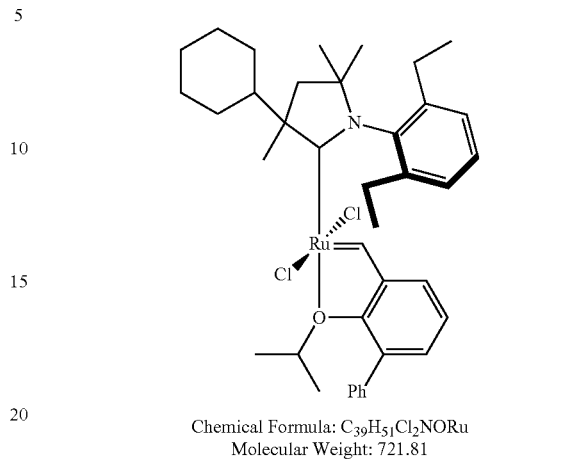

Chemical Formula: $C_{39}H_{51}Cl_2NORu$
Molecular Weight: 721.81

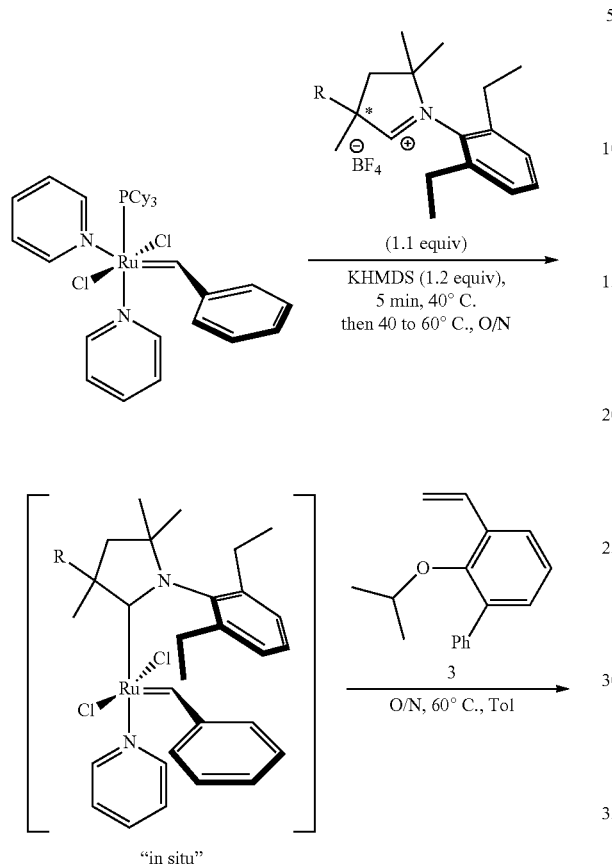

Ru-12c was prepared according to general procedure F with CAAC-12 (27.1 mg, 0.073 mmol, 1.1 equiv), Benzene (2 mL), KHMDS (17.2 mg, 0.080 mmol, 1.2 equiv), Grubbs 3 complex (50 mg, 0.071 mmol, 1 equiv) and styrenyl ether 3 (20.3 mg, 0.085 mmol, 1.2 equiv). The desired product was obtained after purification (eluent: Toluene) as a green solid with the characteristic alkylidene signal $^1$H NMR (400 MHz, $CDCl_3$) at 16.53 ppm.

f. General Procedure for dipp-CAAC Starting from Grubbs 3rd G. and Styrenyl Ether 4

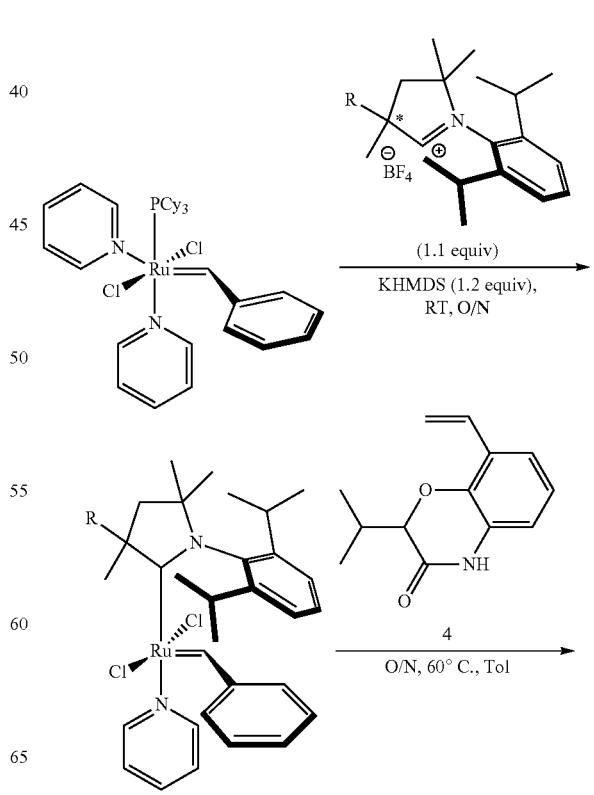

General Procedure F: In a glove box, $CAAC \cdot BF_4$ (1.1 equiv) was dissolved in dry and degassed Toluene (10 mL/mmol Ru). KHMDS (1.2 equiv) was added. The mixture was allowed to stir 5 min at 40° C. Then, Grubbs 3 complex (1 equiv) was then added. The mixture was stirred 1 h at 40° C. then overnight at 60° C. Styrenyl ether 3 (1.2 equiv) was added and the mixture was stirred overnight at 60° C.

The solvent was removed under vacuum and the product was purified by column chromatography (eluent: Toluene). The solid was then diluted in the minimum amount of DCM and precipitated in pentane.

-continued

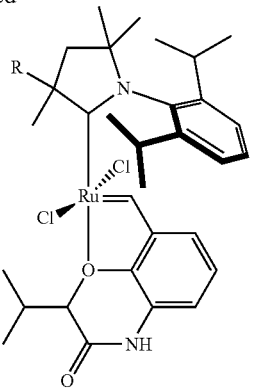

General Procedure G: In a glove box, CAAC·BF$_4$ (1.1 equiv) was dissolved in dry and degassed Toluene (10 mL/mmol Ru). KHMDS (1.2 equiv) was added. The mixture was allowed to stir 30 min at RT. Then, the resulting slurry was filtered through glass fibre filter and Grubbs 3 complex (1 equiv) was then added. The mixture was stirred overnight at RT. The resulting mixture was then added dropwise into a flask containing precooled pentane, resulting into a formation of green precipitate. The precipitation was then pursued until the supernatant become red. The supernatant was then removed and the solid was washed twice with pentane. The complex was dried in vacuo and Styrenyl ether 4 (1.2 equiv) and Toluene (10 mL/mmol Ru) were added and the mixture was stirred overnight at 60° C.

The solvent was removed under vacuum and the product was purified by column chromatography (eluent: Toluene). The solid was then diluted in the minimum amount of DCM and precipitated in pentane.

CAAC (Me/Ph-dipp)-Ru M$_8$ Type Complex (Ru-1c)

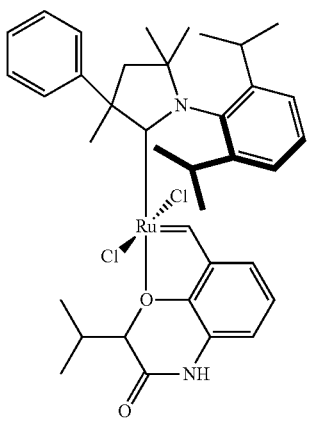

Chemical Formula: C$_{37}$H$_{46}$Cl$_2$N$_2$O$_2$Ru
Molecular Weight: 722.76

Ru-1c was prepared according to the general procedure G with CAAC-1 (34.1 mg, 0.078 mmol, 1.1 equiv), Benzene (2 mL), KHMDS (17.1 mg, 0.086 mmol, 1.2 equiv), Grubbs 3 complex (50 mg, 0.071 mmol, 1 equiv) and styrenyl ether 4 (15.5 mg, 0.085 mmol, 1 equiv). The desired product was obtained after purification (eluent: Toluene) as a green solid in a mixture of two diastereoisomers with the characteristic alkylidene signal $^1$H NMR (400 MHz, CDCl$_3$) at 16.48-16.42 ppm.

Enantioresolution of Ru Based Complexes

Example 1: CAAC (Me/Ph-dipp)-Ru Hoveyda Type Complex (Ru-1a)

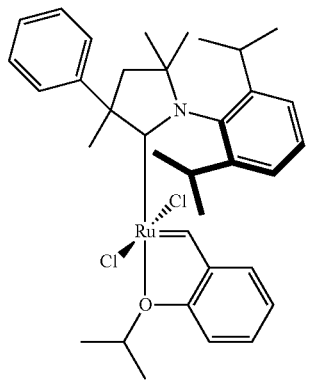

Chemical Formula: C$_{35}$H$_{45}$Cl$_2$NORu
Molecular Weight: 667.72 g·mol$^{-1}$ Screening of Chiral Stationary Phases:

The 10 chiral stationary phases mentioned in the general information part are screened with a mixture heptane/iPrOH/DCM (80/10/10). Only four columns gave a separation of the enantiomers. These four efficient chiral stationary phases are amylose substituted with chloro-phenylcarbamate.

Separations are optimized by modifying the ratio of co-solvents on these four columns:

| Column | Mobile Phase | (+)-Ru-1a | k$_1$ | (−)-Ru-1a | k$_2$ | α | Resolution |
|---|---|---|---|---|---|---|---|
| Chiralpak ID | Heptane/iPrOH/DCM (70/10/20) | 5.36 | 0.82 | 7.04 | 1.38 | 1.69 | 5.16 |
| Chiralpak IE | Heptane/iPrOH/DCM (70/10/20) | 5.34 | 0.81 | 7.63 | 1.59 | 1.96 | 8.24 |

-continued

| Column | Mobile Phase | (+)-Ru-1a | $k_1$ | (−)-Ru-1a | $k_2$ | α | Resolution |
|---|---|---|---|---|---|---|---|
| Chiralpak IF | Heptane/iPrOH/DCM (70/10/20) | 5.00 | 0.69 | 6.54 | 1.22 | 1.76 | 6.41 |
| Chiralpak IG | Heptane/iPrOH/DCM (70/10/20) | 6.42 | 1.18 | 8.87 | 2.01 | 1.71 | 5.39 |

The four columns allow the separation with a good enantioselectivity and an excellent resolution. Chiralpak IF (250×100 mm) is chosen for preparative separation due to the shorter elution time, and shows a good loading capacity: 50 mg of each enantiomer are obtained in less than 3 hours, by successive stacked injections.

Analytical chiral HPLC separation: Chiralpak IF column with a UV and CD detector at λ=254 nm; flow rate 1 mL/min; eluent: heptane/2-iPrOH/DCM 70/10/20; 1$^{st}$ enantiomer (+)-(R)-Ru-1a: Rt=5.00 min and 2$^{nd}$ enantiomer (−)-(S)-Ru-1a: Rt=6.54 min.

Semi-preparative separation: The preparative chiral HPLC separation was done on a Chiralpak IF column (250×10 mm, 5 μm) with heptane/2-PrOH/dichloromethane (70/10/20) as mobile phase, flow-rate=5 mL/min, UV detection at 254 nm with multiple injections (34 times 150 μL, every 4.5 min). From 106 mg of racemic mixture dissolved in 5.1 mL of DCM, 49 mg of the first eluted enantiomer with ee>99% ((+)-(R)-Ru-1a: 46% yield) and 48 mg of the second eluted enantiomer with ee>98% ((−)-(S)-Ru-1a: 45% yield) were obtained.

Optical Rotations

| λ (nm) | (+)-(R)-Ru-1a First eluted enantiomer on Chiralpak IF $[α]_λ^{25}$ ($CH_2Cl_2$, c = 0.0188) | (−)-(S)-Ru-1a Second eluted enantiomer on Chiralpak IF $[α]_λ^{25}$ ($CH_2Cl_2$, c = 0.0192) |
|---|---|---|
| 589 | +780 | −780 |
| 578 | +690 | −690 |
| 546 | +330 | −330 |

Example 2: CAAC (Me/1-Napht-dipp)-Ru Hoveyda Type Complex (Ru-2a)

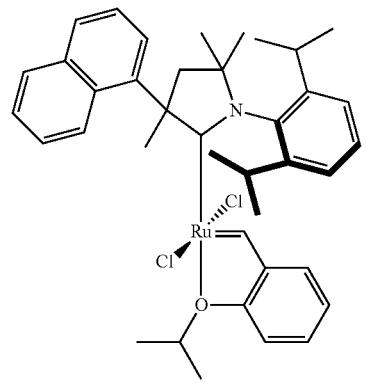

Chemical Formula: $C_{39}H_{47}Cl_2NORu$
Molecular Weight: 717.78

Analytical chiral HPLC separation: Chiralpak IF column with a UV and CD detector at λ=254 nm; flow rate 1 mL/min; eluent: heptane/iPrOH/DCM 70/10/20; 1$^{st}$ enantiomer (−)-(R)-Ru-2a: Rt=5.23 min and 2$^{nd}$ enantiomer (+)-(S)-Ru-2a: Rt=7.75 min.

Preparative separation: The preparative chiral HPLC separation was done on a Chiralpak IF column (250×10 mm, 5 μm) with heptane/iPrOH/DCM (70/10/20) as mobile phase, flow-rate=5 mL/min, UV detection at 254 nm with multiple injections (17 times 150 μL, every 8.7 min). From 89 mg of racemic mixture dissolved in 2.5 mL of DCM, 32 mg of the first eluted enantiomer with ee>99% ((−)-(R)-Ru-2a: 36% yield) and 32 mg of the second eluted enantiomer with ee>98.5% ((+)-(S)-Ru-2a: 36% yield) were obtained.

Optical Rotations

| λ (nm) | (−)-(R)-Ru-2a First eluted enantiomer on Chiralpak IF $[α]_λ^{25}$ ($CH_2Cl_2$, c = 0.0093) | (+)-(S)-Ru-2a Second eluted enantiomer on Chiralpak IF $[α]_λ^{25}$ ($CH_2Cl_2$, c = 0.0093) |
|---|---|---|
| 589 | −720 | +720 |
| 578 | −731 | +731 |
| 546 | −430 | +430 |

Example 3: CAAC (Me/Ph-dipp)-Ru Grela Type Complex (Ru-1b)

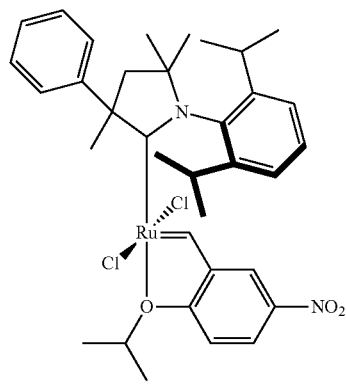

Chemical Formula: $C_{35}H_{44}Cl_2N_2O_3Ru$
Molecular Weight: 712.72

Analytical chiral HPLC separation: Chiralpak IE column with a UV and CD detector at I=254 nm; flow rate 1 mL/min; eluent: heptane/EtOH/DCM 60/20/20; 1$^{st}$ enantiomer (+)-(R)-Ru-1b: Rt=4.85 min and 2$^{nd}$ enantiomer (−)-(S)-Ru-1b: Rt=6.52 min.

Preparative separation: The preparative chiral HPLC separation was done on a Chiralpak IE column (250×10 mm, 5 μm) with heptane/EtOH/DCM (60/20/20) as mobile phase, flow-rate=5 mL/min, UV detection at 254 nm with multiple injections (15 times 500 μL, every 7.5 min). From 78.5 mg of racemic mixture dissolved in 7.5 mL of DCM/Hexanes (65/35), 37 mg of the first eluted enantiomer with ee>99.5% ((+)-(R)-Ru-1b: 47% yield) and 36 mg of the second eluted enantiomer with ee>99.5% ((−)-(S)-Ru-1 b: 46% yield) were obtained.

Optical Rotations

| $\lambda$ (nm) | (+)-(R)-Ru-1b First eluted enantiomer on Chiralpak IE $[\alpha]_\lambda^{25}$ (CH$_2$Cl$_2$, c = 0.03) | (−)-(S)-Ru-1b Second eluted enantiomer on Chiralpak IE $[\alpha]_\lambda^{25}$ (CH$_2$Cl$_2$, c = 0.03) |
|---|---|---|
| 589 | +436 | −436 |
| 578 | +317 | −317 |
| 546 | +55 | −55 |

Example 4: CAAC (Me/1-Napht-dipp)-Ru Grela Type Complex (Ru-2b)

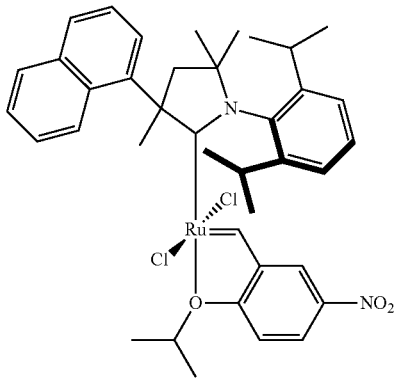

Chemical Formula: C$_{39}$H$_{46}$Cl$_2$N$_2$O$_3$Ru
Molecular Weight: 762.78

Analytical chiral HPLC separation: Chiralpak ID column with a UV and CD detector at l=254 nm; flow rate 1 mL/min; eluent: heptane/EtOH/DCM 60/20/20; 1$^{st}$ enantiomer (−)-(R)-Ru-2b: Rt=5.52 min and 2$^{nd}$ enantiomer (+)-(S)-Ru-2b: Rt=7.04 min.

Preparative separation: The preparative chiral HPLC separation was done on a Chiralpak ID column (250×10 mm, 5 µm) with heptane/EtOH/DCM (60/20/20) as mobile phase, flow-rate=5 mL/min, UV detection at 254 nm with multiple injections (12 times 150 µL, every 8.3 min). From 57 mg of racemic mixture dissolved in 1.8 mL of DCM, 22 mg of the first eluted enantiomer with ee>99.5% ((−)-(R)-Ru-4: 39% yield) and 22 mg of the second eluted enantiomer with ee>99.5% ((+)-(S)-Ru-4: 39% yield) were obtained.

Optical Rotations

| $\lambda$ (nm) | (−)-(R)-Ru-2b First eluted enantiomer on Chiralpak ID $[\alpha]_\lambda^{25}$ (CH$_2$Cl$_2$, c = 0.02) | (+)-(S)-Ru-2b Second eluted enantiomer on Chiralpak ID $[\alpha]_\lambda^{25}$ (CH$_2$Cl$_2$, c = 0.02) |
|---|---|---|
| 589 | −525 | +525 |
| 578 | −445 | +445 |
| 546 | −130 | +130 |

Example 4-1: CAAC (Me/2-Napht-dipp)-Ru Grela Type Complex (Ru-3b)

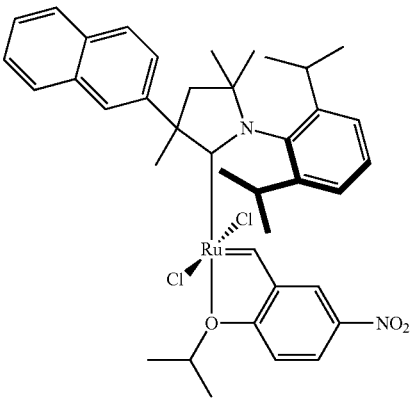

Chemical Formula: C$_{39}$H$_{46}$Cl$_2$N$_2$O$_3$Ru
Molecular Weight: 762.78

Analytical chiral HPLC separation: Chiralpak IE column with a UV and CD detector at λ=254 nm; flow rate 1 mL/min; eluent: heptane/EtOH/DCM 20/40/40; 1$^{st}$ enantiomer (+)-(R)-Ru-3b: Rt=4.00 min and 2$^{nd}$ enantiomer (−)-(S)-Ru-3b: Rt=6.48 min.

Preparative separation: The preparative chiral HPLC separation was done on a Chiralpak IE column (250×10 mm, 5 µm) with heptane/EtOH/DCM (20/40/40) as mobile phase, flow-rate=5 mL/min, UV detection at 290 nm with multiple injections (10 times 300 µL, every 7.5 min). From 36 mg of racemic mixture dissolved in 3 mL of DCM/EtOH (50/50), 16 mg of the first eluted enantiomer with ee>99.5% ((+)-(R)-Ru-3b: 44% yield) and 16 mg of the second eluted enantiomer with ee>99.5% ((−)-(S)-Ru-3b: 44% yield) were obtained.

Optical Rotations

| $\lambda$ (nm) | (+)-(R)-Ru-3b First eluted enantiomer on Chiralpak IE $[\alpha]_\lambda^{25}$ (CH$_2$Cl$_2$, c = 0.019) | (−)-(S)-Ru-3b Second eluted enantiomer on Chiralpak IE $[\alpha]_\lambda^{25}$ (CH$_2$Cl$_2$, c = 0.021) |
|---|---|---|
| 589 | +360 | −360 |
| 578 | +262 | −262 |
| 546 | +58 | −58 |

Example 5: CAAC (Me/3,5-MePh-dipp)-Ru Grela Type Complex (Ru-4b)

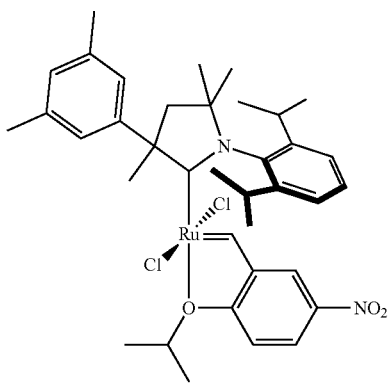

Chemical Formula: $C_{37}H_{48}Cl_2N_2O_3Ru$
Molecular Weight: 740.77

Analytical chiral HPLC separation: Chiralpak IE column with a UV and CD detector at l=254 nm; flow rate 1 mL/min; eluent: heptane/EtOH/DCM 60/20/20; $1^{st}$ enantiomer (+)-(R)-Ru-4b: Rt=4.03 min and $2^{nd}$ enantiomer (−)-(S)-Ru-4b: Rt=5.80 min.

Preparative separation: The preparative chiral HPLC separation was done on a Chiralpak IE column (250×10 mm, 5 μm) with heptane/EtOH/DCM (60/20/20) as mobile phase, flow-rate=5 mL/min, UV detection at 254 nm with multiple injections (10 times 300 μL, every 4.0 min). From 120 mg of racemic mixture dissolved in 3 mL of DCM/Hexanes (65/35), 52 mg of the first eluted enantiomer with ee>99.5% ((+)-(R)-Ru-4b: 43% yield) and 53 mg of the second eluted enantiomer with ee>99.5% ((−)-(S)-Ru-4b: 44% yield) were obtained.

Optical Rotations

| λ (nm) | (+)-(R)-Ru-4b First eluted enantiomer on Chiralpak IE $[α]_λ^{25}$ ($CH_2Cl_2$, c = 0.019) | (−)-(S)-Ru-4b Second eluted enantiomer on Chiralpak IE $[α]_λ^{25}$ ($CH_2Cl_2$, c = 0.023) |
|---|---|---|
| 589 | +420 | −420 |
| 578 | +320 | −320 |
| 546 | +120 | −120 |

Example 5-1: CAAC (Me/3,5-$^tBu_2$Ph-dipp)-Ru Grela Type Complex (Ru-5b)

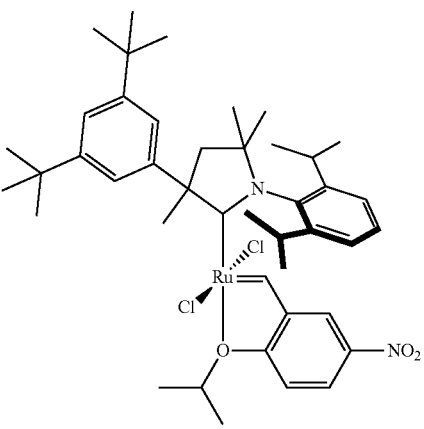

Chemical Formula: $C_{43}H_{60}Cl_2N_2O_3Ru$
Molecular Weight: 824.93

Analytical chiral HPLC separation: Chiralpak IG column with a UV and CD detector at λ=254 nm; flow rate 1 mL/min; eluent: heptane/EtOH/DCM 50/20/30; $1^{st}$ enantiomer (+)-(R)-Ru-5b: Rt=3.21 min and $2^{nd}$ enantiomer (−)-(S)-Ru-5b: Rt=6.17 min.

Preparative separation: The preparative chiral HPLC separation was done on a Chiralpak IG column (250×10 mm, 5 μm) with heptane/EtOH/DCM (50/20/30) as mobile phase, flow-rate=5 mL/min, UV detection at 280 nm with multiple injections (15 times 200 μL, every 6.5 min). From 98 mg of racemic mixture dissolved in 3 mL of DCM, 37 mg of the first eluted enantiomer with ee>99.5% ((+)-(R)-Ru-5b: 38% yield) and 38 mg of the second eluted enantiomer with ee>99.5% ((−)-(S)-Ru-5b: 38% yield) were obtained.

Optical Rotations

| λ (nm) | (+)-(R)-Ru-5b First eluted enantiomer on Chiralpak IE $[α]_λ^{25}$ ($CH_2Cl_2$, c = 0.02) | (−)-(S)-Ru-5b Second eluted enantiomer on Chiralpak IE $[α]_λ^{25}$ ($CH_2Cl_2$, c = 0.02) |
|---|---|---|
| 589 | +630 | −630 |
| 578 | +525 | −525 |
| 546 | +300 | −300 |

Example 6: CAAC (Me/Cy-dipp)-Ru Grela Type Complex (Ru-6b)

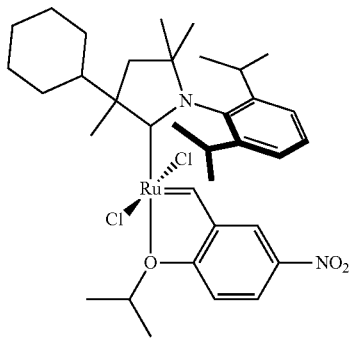

Chemical Formula: $C_{35}H_{50}Cl_2N_2O_3Ru$
Molecular Weight: 718.77

Analytical chiral HPLC separation: Chiralpak IF column with a UV and CD detector at λ=254 nm; flow rate 1 mL/min; eluent: heptane/EtOH/DCM 60/20/20; $1^{st}$ enantiomer (+)-(R)-Ru-6b: Rt=5.92 min and $2^{nd}$ enantiomer (−)-(S)-Ru-6b: Rt=7.93 min.

Preparative separation: The preparative chiral HPLC separation was done on a Chiralpak IF column (250×10 mm, 5 μm) with heptane/EtOH/DCM (60/20/20) as mobile phase, flow-rate=5 mL/min, UV detection at 254 nm with multiple injections (17 times 300 μL, every 7.0 min). From 38 mg of racemic mixture dissolved in 5 mL of DCM/Hexanes (60/40), 14 mg of the first eluted enantiomer with ee>99.5% ((+)-(R)-Ru-6b: 37% yield) and 15 mg of the second eluted enantiomer with ee>99.5% ((−)-(S)-Ru-6b: 39% yield) were obtained.

Optical Rotations

| λ (nm) | (+)-R-Ru-6b First eluted enantiomer on Chiralpak IF $[α]_λ^{25}$ ($CH_2Cl_2$, c = 0.018) | (−)-S-Ru-6b Second eluted enantiomer on Chiralpak IF $[α]_λ^{25}$ ($CH_2Cl_2$, c = 0.022) |
| --- | --- | --- |
| 589 | +232 | −231 |
| 578 | +94 | −92 |
| 546 | −227 | +226 |

Example 7: CAAC (Me/Ph-dep)-Ru Grela Type Complex (Ru-8b)

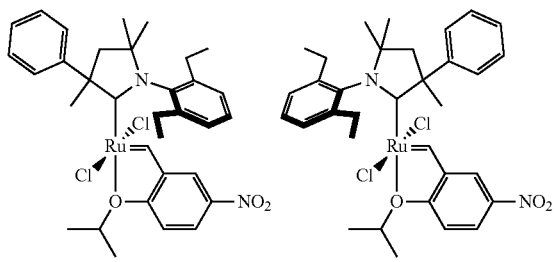

Chemical Formula: $C_{33}H_{40}Cl_2N_2O_3Ru$
Molecular Weight: 684.65

Analytical chiral HPLC separation: Chiralpak IE column with a UV and CD detector at l=254 nm; flow rate 1 mL/min; eluent: heptane/EtOH/DCM 60/20/20; $1^{st}$ enantiomer (+)-(R)-Ru-8b: Rt=5.54 min and $2^{nd}$ enantiomer (−)-(S)-Ru-8b: Rt=6.84 min.

Preparative separation: The preparative chiral HPLC separation was done on a Chiralpak IE column (250×10 mm, 5 μm) with heptane/EtOH/DCM (60/20/20) as mobile phase, flow-rate=5 mL/min, UV detection at 254 nm with multiple injections (23 times 350 μL, every 7.7 min). From 103 mg of racemic mixture dissolved in 8 mL of DCM/Hexanes (60/40), 50 mg of the first eluted enantiomer with ee>99.5% ((+)-(R)-Ru-8b: 49% yield) and 50 mg of the second eluted enantiomer with ee>98.5% ((−)-(S)-Ru-8b: 49% yield) were obtained.

Optical Rotations

| λ (nm) | (+)-(R)-Ru-8b First eluted enantiomer on Chiralpak IE $[α]_λ^{25}$ ($CH_2Cl_2$, c = 0.018) | (−)-(S)-Ru-8b Second eluted enantiomer on Chiralpak IE $[α]_λ^{25}$ ($CH_2Cl_2$, c = 0.02) |
| --- | --- | --- |
| 589 | +179 | −179 |
| 578 | +92 | −92 |
| 546 | −33 | +34 |

Example 8: $^{Me/Ph}$CAAC (Me/Ph-dipp)-Ru Hoveyda Type Complex (Ru-7b)

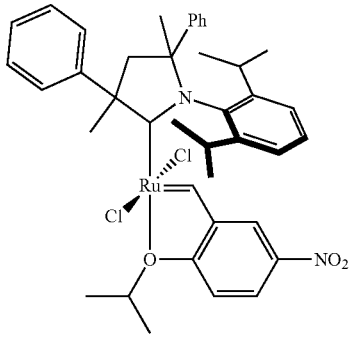

Chemical Formula: $C_{40}H_{46}Cl_2N_2O_3Ru$
Molecular Weight: 774.79

Analytical chiral HPLC separation: Chiralpak ID column with a UV and CD detector at λ=254 nm; flow rate 1 mL/min; eluent: heptane/EtOH/DCM 40/30/30; $1^{st}$ enantiomer (+)-Ru-7b: Rt=4.94 min and $2^{nd}$ enantiomer (−)-Ru-7b: Rt=8.61 min.

Preparative separation: The preparative chiral HPLC separation was done on a Chiralpak ID column (250×10 mm, 5 μm) with heptane/EtOH/DCM (40/30/30) as mobile phase, flow-rate=5 mL/min, UV detection at 254 nm with multiple injections (8 times 200 μL, every 9.2 minutes). From 19 mg of racemic mixture dissolved in 1.5 mL of DCM, 8 mg of the first eluted enantiomer with ee>99.5% ((+)-Ru-7b: 42% yield) and 9 mg of the second eluted enantiomer with ee>99.5% ((−)-Ru-7b: 42% yield) were obtained.

Optical Rotations

| λ (nm) | (+)-Ru-7b First eluted enantiomer on Chiralpak ID $[\alpha]_\lambda^{25}$ (CH$_2$Cl$_2$, c = 0.014) | (−)-Ru-7b Second eluted enantiomer on Chiralpak ID $[\alpha]_\lambda^{25}$ (CH$_2$Cl$_2$, c = 0.014) |
|---|---|---|
| 589 | +650 | −650 |
| 578 | +500 | −500 |
| 546 | +200 | −200 |

Example 8-1: CAAC (Me/Ph-dep)-Ru Hoveyda Type Complex (Ru-8a)

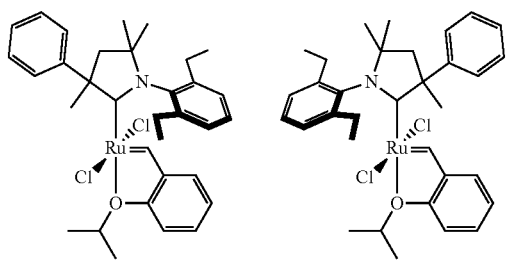

Chemical Formula: C$_{33}$H$_{41}$Cl$_2$NORu
Molecular Weight: 639.67

Analytical chiral HPLC separation: Chiralpak IE column with a UV and CD detector at λ=254 nm; flow rate 1 mL/min; eluent: heptane/EtOH/DCM 60/20/20; 1$^{st}$ enantiomer (+)-(R)-Ru-8a: Rt=4.94 min and 2$^{nd}$ enantiomer (−)-(S)-Ru-8a: Rt=5.88 min.

Preparative separation: The preparative chiral HPLC separation was done on a Chiralpak IE column (250×10 mm, 5 μm) with heptane/EtOH/DCM (60/20/20) as mobile phase, flow-rate=5 mL/min, UV detection at 254 nm with multiple injections (60 times 100 μL, every 6.6 min). From 225 mg of racemic mixture dissolved in 6 mL of DCM, 97 mg of the first eluted enantiomer with ee>99.5% ((+)-(R)-Ru-8a: 43% yield) and 100 mg of the second eluted enantiomer with ee>99.5% ((−)-(S)-Ru-8a: 44% yield) were obtained.

Optical Rotations

| λ (nm) | (+)-(R)-Ru-8a First eluted enantiomer on Chiralpak IE $[\alpha]_\lambda^{25}$ (CH$_2$Cl$_2$, c = 0.02) | (−)-(S)-Ru-8a Second eluted enantiomer on Chiralpak IE $[\alpha]_\lambda^{25}$ (CH$_2$Cl$_2$, c = 0.02) |
|---|---|---|
| 589 | +565 | −565 |
| 578 | +425 | −425 |
| 546 | +55 | −55 |

Example 9: CAAC (Me/1-Napht-dep)-Ru Grela Type Complex (Ru-9a)

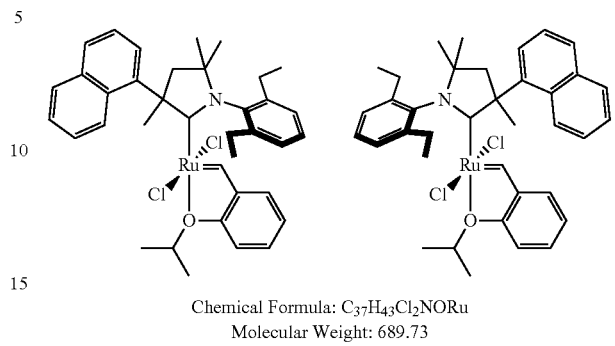

Chemical Formula: C$_{37}$H$_{43}$Cl$_2$NORu
Molecular Weight: 689.73

Analytical chiral HPLC separation: Chiralpak IF column with a UV and CD detector at λ=254 nm; flow rate 1 mL/min; eluent: heptane/EtOH/DCM 60/20/20; 1$^{st}$ enantiomer (+)-Ru-9a: Rt=5.48 min and 2$^{nd}$ enantiomer (−)-Ru-9a: Rt=6.75 min.

Preparative separation: The preparative chiral HPLC separation was done on a Chiralpak IF column (250×10 mm, 5 μm) with heptane/EtOH/DCM (60/20/20) as mobile phase, flow-rate=5 mL/min, UV detection at 254 nm with multiple injections (32 times 80 μL, every 8 minutes). From 184 mg of racemic mixture dissolved in 8 mL of DCM/Hexanes (60/40), 83 mg of the first eluted enantiomer with ee>99.5% ((+)-Ru-9a: 45% yield) and 72 mg of the second eluted enantiomer with ee>98.5% ((−)-(S)-Ru-9a: 39% yield) were obtained.

Optical Rotations

| λ (nm) | (+)-Ru-9a First eluted enantiomer on Chiralpak IF $[\alpha]_\lambda^{25}$ (CH$_2$Cl$_2$, c = 0.02) | (−)-Ru-9a Second eluted enantiomer on Chiralpak IF $[\alpha]_\lambda^{25}$ (CH$_2$Cl$_2$, c = 0.02) |
|---|---|---|
| 589 | +310 | −310 |
| 578 | +250 | −250 |
| 546 | +170 | −170 |

Example 9-1: CAAC (Me/1-Napht-dep)-Ru Grela Type Complex (Ru-9b)

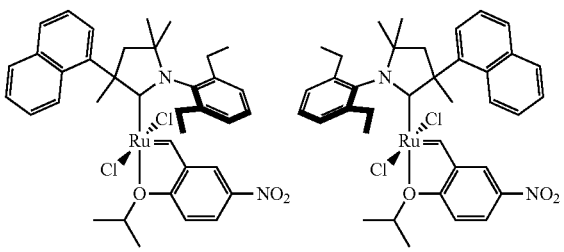

Chemical Formula: C$_{37}$H$_{42}$Cl$_2$N$_2$O$_3$Ru
Molecular Weight: 734.72

Analytical chiral HPLC separation: Chiralpak IF column with a UV and CD detector at λ=230 nm; flow rate 1 mL/min; eluent: heptane/EtOH/DCM 20/40/40; 1$^{st}$ enantiomer (−)-Ru-9b: Rt=5.12 min and 2$^{nd}$ enantiomer (+)-Ru-9b: Rt=10.25 min.

Preparative separation: The preparative chiral HPLC separation was done on a Chiralpak IF column (250×10 mm, 5 μm) with heptane/EtOH/DCM (20/40/40) as mobile phase, flow-rate=5 mL/min, UV detection at 230 nm with multiple injections (10 times 200 μL, every 12 minutes). From 15 mg of racemic mixture dissolved in 2 mL of DCM, 4 mg of the first eluted enantiomer with ee>99.5% ((−)-Ru-9b: 27% yield) and 4 mg of the second eluted enantiomer with ee>99.5% ((+)-Ru-9b: 27% yield) were obtained.

Optical Rotations

| $\lambda$ (nm) | (+)-(R)-Ru-9 First eluted enantiomer on Chiralpak IE $[\alpha]_\lambda^{25}$ (CH$_2$Cl$_2$, c = 0.022) | (−)-(S)-Ru-9 Second eluted enantiomer on Chiralpak IE $[\alpha]_\lambda^{25}$ (CH$_2$Cl$_2$, c = 0.018) |
|---|---|---|
| 589 | +280 | −280 |
| 578 | +235 | −235 |

Example 9-2: CAAC (Me/2-Napht-dep)-Ru Grela Type Complex (Ru-10b)

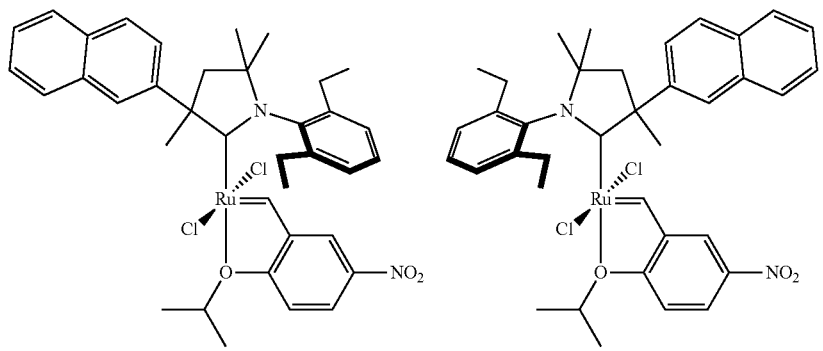

Chemical Formula: C$_{37}$H$_{42}$Cl$_2$N$_2$O$_3$Ru
Molecular Weight: 734.72

Analytical chiral HPLC separation: Chiralpak IE column with a UV and CD detector at λ=230 nm; flow rate 1 mL/min; eluent: heptane/EtOH/DCM 40/30/30; 1$^{st}$ enantiomer (+)-(R)-Ru-10b: Rt=4.72 min and 2$^{nd}$ enantiomer (−)-(S)-Ru-10b: Rt=7.81 min.

Preparative separation: The preparative chiral HPLC separation was done on a Chiralpak IE column (250×10 mm, 5 μm) with heptane/EtOH/DCM (40/30/30) as mobile phase, flow-rate=5 mL/min, UV detection at 230 nm with multiple injections (25 times 200 μL, every 9.0 min). From 151 mg of racemic mixture dissolved in 5 mL of DCM, 68 mg of the first eluted enantiomer with ee>99.5% ((+)-(R)-Ru-10a: 45% yield) and 66 mg of the second eluted enantiomer with ee>98.5% ((−)-(S)-Ru-10a: 44% yield) were obtained.

Optical Rotations

| $\lambda$ (nm) | (+)-(R)-Ru-10b First eluted enantiomer on Chiralpak IE $[\alpha]_\lambda^{25}$ (CH$_2$Cl$_2$, c = 0.022) | (−)-(S)-Ru-10b Second eluted enantiomer on Chiralpak IE $[\alpha]_\lambda^{25}$ (CH$_2$Cl$_2$, c = 0.018) |
|---|---|---|
| 589 | +281 | −278 |
| 578 | +253 | −250 |
| 546 | +249 | −246 |

Example 10: CAAC (Me/3,5-MePh-dep)-Ru Grela Type Complex (Ru-11b)

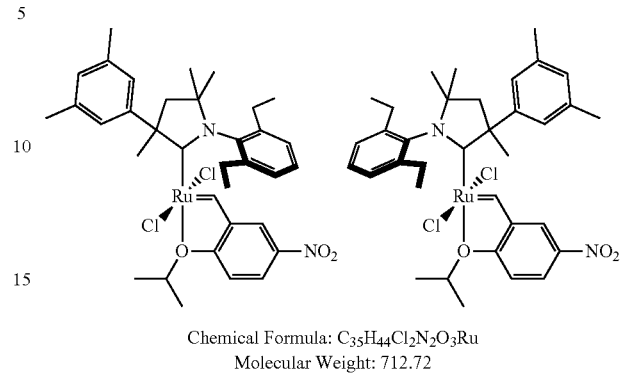

Chemical Formula: C$_{35}$H$_{44}$Cl$_2$N$_2$O$_3$Ru
Molecular Weight: 712.72

Analytical chiral HPLC separation: Chiralpak IE column with a UV and CD detector at λ=230 nm; flow rate 1 mL/min; eluent: heptane/EtOH/DCM 60/20/20; 1$^{st}$ enantiomer (+)-(R)-Ru-11b: Rt=4.63 min and 2$^{nd}$ enantiomer (−)-(S)-Ru-11b: Rt=6.57 min.

Preparative separation: The preparative chiral HPLC separation was done on a Chiralpak IE column (250×10 mm, 5 μm) with heptane/EtOH/DCM (60/20/20) as mobile phase, flow-rate=5 mL/min, UV detection at 230 nm with multiple injections (16 times 250 μL, every 8.0 min). From 152 mg of racemic mixture dissolved in 4 mL of DCM, 72 mg of the first eluted enantiomer with ee>99.5% ((+)-(R)-Ru-11 b: 47% yield) and 72 mg of the second eluted enantiomer with ee>98.5% ((−)-(S)-Ru-11 b: 47% yield) were obtained.

Optical Rotations

| $\lambda$ (nm) | (+)-(R)-Ru-11b First eluted enantiomer on Chiralpak IE $[\alpha]_\lambda^{25}$ (CH$_2$Cl$_2$, c = 0.022) | (−)-(S)-Ru-11b Second eluted enantiomer on Chiralpak IE $[\alpha]_\lambda^{25}$ (CH$_2$Cl$_2$, c = 0.018) |
|---|---|---|
| 589 | +277 | −275 |
| 578 | +212 | −209 |
| 546 | +161 | −159 |

Example 11: CAAC (Me/Cy-dep)-Ru Grela Type Complex (Ru-12b)

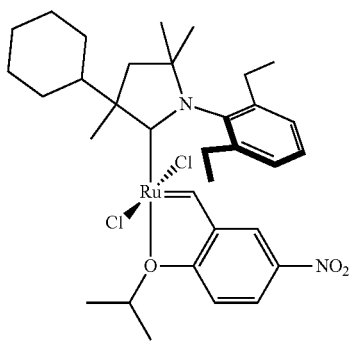

Chemical Formula: $C_{32}H_{46}Cl_2N_2O_3Ru$
Molecular Weight: 690.71

Analytical chiral HPLC separation: Chiralpak IF column with a UV and CD detector at I=254 nm; flow rate 1 mL/min; eluent: heptane/EtOH/DCM 80/10/10; $1^{st}$ enantiomer (−)-(R)-Ru-12b: Rt=15.01 min and $2^{nd}$ enantiomer (+)-(S)-Ru-12B: Rt=16.88 min.

Preparative separation: The preparative chiral HPLC separation was done on a Chiralpak IF column (250×10 mm, 5 µm) with heptane/EtOH/DCM (80/10/10) as mobile phase, flow-rate=5 mL/min, UV detection at 254 nm with multiple injections (30 times 100 µL, every 6.5 min). From 190 mg of racemic mixture dissolved in 3 mL of DCM, 67 mg of the first eluted enantiomer with ee>99.5% ((−)-(R)-Ru-12b: 35% yield) and 79 mg of the second eluted enantiomer with ee>99.5% ((+)-(S)-Ru-12b: 42% yield) were obtained.

Optical Rotations

| λ (nm) | (−)-(R)-Ru-12b First eluted enantiomer on Chiralpak IF $[α]_λ^{25}$ ($CH_2Cl_2$, c = 0.017) | (+)-(S)-Ru-12b Second eluted enantiomer on Chiralpak IF $[α]_λ^{25}$ ($CH_2Cl_2$, c = 0.023) |
|---|---|---|
| 589 | −116 | +116 |
| 578 | −237 | +236 |
| 546 | −445 | +444 |

All compounds of examples 1-11 were characterized by X-ray diffraction.

Example 12: CAAC (Me/CH$_2$pCymene-dep)-Ru Grela Type Complex (Ru-13b)

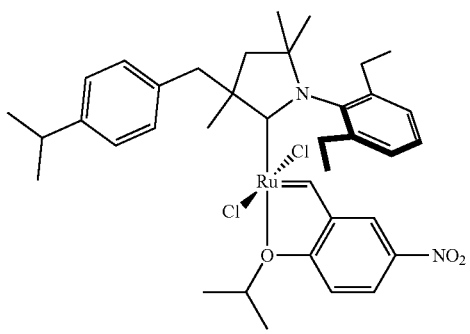

Chemical Formula: $C_{37}H_{48}Cl_2N_2O_3Ru$
Molecular Weight: 740.77

Analytical chiral HPLC separation: Chiralpak IF column with a UV and CD detector at λ=254 nm; flow rate 1 mL/min; eluent: heptane/EtOH/DCM 80/10/10; $1^{st}$ enantiomer Ru-13b: Rt=6.21 min and $2^{nd}$ enantiomer Ru-13b: Rt=7.37 min.

Preparative separation: The preparative chiral HPLC separation was done on a Chiralpak IF column (250×10 mm, 5 µm) with heptane/EtOH/DCM (80/10/10) as mobile phase, flow-rate=5 mL/min, UV detection at 254 nm with multiple injections (70 times 45 µL, every 3.8 min). From 70 mg of racemic mixture dissolved in 3 mL of DCM/hexanes (1/1) mixture, 32 mg of the first eluted enantiomer with ee>99.5% ((+)-Ru-13b: 46% yield) and 29 mg of the second eluted enantiomer with ee 98% ((−)-Ru-13b: 41% yield) were obtained.

Optical Rotations

| λ (nm) | (+)-Ru-13b First eluted enantiomer on Chiralpak IF $[α]_λ^{25}$($CH_2Cl_2$, c = 0.012) | (−)-Ru-13b Second eluted enantiomer on Chiralpak IF $[α]_λ^{25}$ ($CH_2Cl_2$, c = 0.012) |
|---|---|---|
| 589 | +138 | −136 |
| 578 | +81 | −80 |
| 546 | −57 | +56 |

Halogens Exchange on Optically Pure Complexes a. Synthesis of Iodine Complex

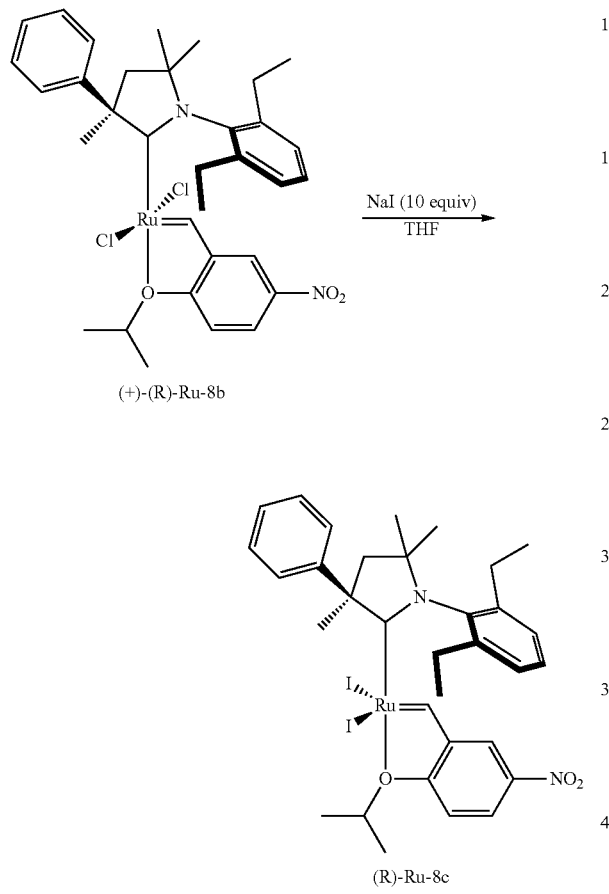

In a flame-dried NMR tube under Ar, were placed (+)-(R)-Ru-8b (19.3 mg, 0.028 mmol, 1 equiv) and NaI (44 mg, 0.284 mmol, 10.5 equiv). 0.5 mL of degassed anhydrous THF-d8 was added. The conversion was monitored by $^1$H NMR. The reaction was finished after 3 h at rt. The product was purified by column chromatography (eluent: toluene) to yield a green-brown solid (29 mg, 94% yield).

$^1$H NMR (400 MHz, CDCl$_3$): δ (ppm) 15.30 (d, J=0.8 Hz, 1H), 8.50 (dd, J=9.2, 2.7 Hz, 1H), 8.36-8.30 (m, 2H), 7.74-7.64 (m, 2H), 7.63-7.55 (m, 2H), 7.52 (dq, J=7.7, 1.6 Hz, 2H), 7.47-7.39 (m, 1H), 7.08-7.01 (m, 1H), 5.30-5.16 (m, 1H), 3.22 (d, J=12.4 Hz, 1H), 3.02 (dq, J=15.0, 7.5 Hz, 1H), 2.82-2.64 (m, 2H), 2.63-2.50 (m, 4H), 2.33 (d, J=12.3 Hz, 1H), 1.86 (d, J=6.1 Hz, 3H), 1.76 (d, J=6.2 Hz, 3H), 1.59 (s, 3H), 1.44 (s, 3H), 1.23 (t, J=7.4 Hz, 3H), 0.92 (t, J=7.4 Hz, 3H).

$^{13}$C NMR (101 MHz, CDCl$_3$): δ (ppm) 294.7, 264.5, 156.7, 147.3, 143.7, 143.2, 143.0, 142.4, 138.5, 130.6 (2C), 129.5, 128.5, 127.3, 127.2, 125.8, 125.2 (2C), 119.2, 113.9, 78.2, 77.7, 64.0, 45.4, 34.1, 31.7, 27.3, 27.0, 24.9, 23.3, 23.1, 15.5, 14.7.

HRMS for C$_{33}$H$_{40}$N$_2$O$_3$I$_2$$^{102}$Ru (M$^+$) calc.: 868.01665, found: 868.0168 (0 ppm).

X-Ray diffraction Suitable crystals of Ru-8c for XRD were grown by slow diffusion of pentane into DCM. The Flack parameter was refined to a value of zero, providing confirmation of the absolute configuration as the (R)-enantiomer.

b. Synthesis of Catechol Bisthiolate Complex

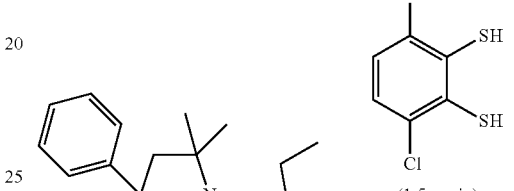

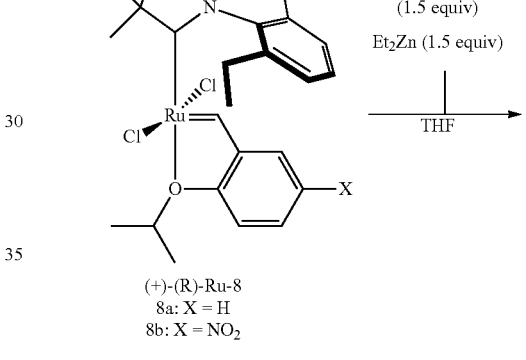

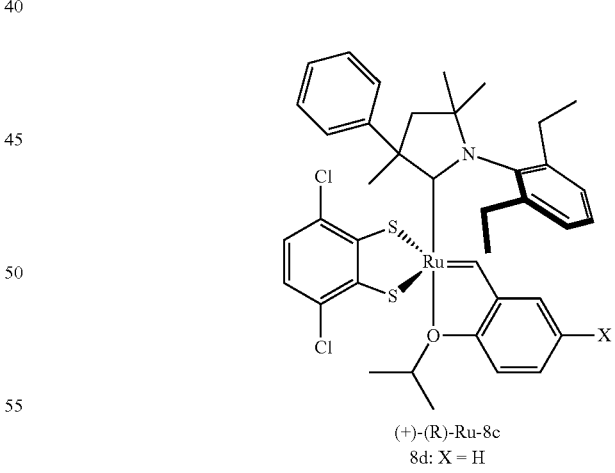

General Procedure H

In a flame dried vial, 3,6-dichlorobenzene-1,2-dithiol (1.5 equiv) and Diethyl zinc solution (0.9 M in hexanes, 1.5 equiv) were dissolved in dry and degassed THF. After 5 min of stirring at rt, the mixture was entered in the glove box. The desired RuCl$_2$ complex (1 equiv) was dissolved in THF and was added to the previous mixture. After 20 min of stirring at rt, crude mixture was filtered through Cellite pad in the glove box (eluent: THF). Volatiles were removed under vacuum. The solid was diluted in DCM and filtered through an other Cellite pad (eluent: DCM). The compound was then washed with hexane and filtered through cotton. Volatiles were removed under vacuum. Final products are highly sensitive to air and moisture, use only in glove box, in dry and deoxygenated solvents.

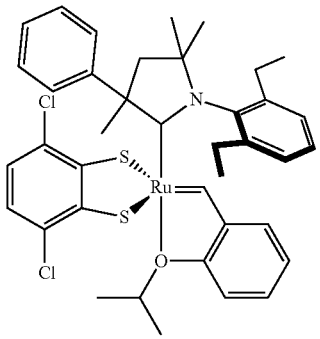

Chemical Formula: C$_{39}$H$_{43}$Cl$_2$NORuS$_2$
Molecular Weight: 777.87

CAAC (Me/Ph-dipp)-catecholthiolate-Ru Hoveyda Type Complex (Ru-8d)

Ru-8b was prepared according to general procedure H for the complexes synthesis with Ru-8a (63 mg, 0.10 mmol, 1 equiv), 1,6-dichloro-1,2-benzene dithiol (31 mg, 0.15 mmol, 1.5 equiv), Et$_2$Zn (0.15 mL, 0.14 mmol, 1.4 equiv) and THF (1.4 mL). The mixture was stirred 20 min at rt. The desired product was obtained after purification as a brown solid (75 mg, 97% yield).

$^1$H NMR (500 MHz, THF-d$_8$): δ (ppm) 13.80 (s, 1H), 7.81 (d, J=7.7 Hz, 2H), 7.43 (t, J=7.6 Hz, 3H), 7.32 (t, J=7.4 Hz, 1H), 7.24 (ddd, J=8.6, 7.1, 1.7 Hz, 1H), 7.14 (t, J=7.7 Hz, 1H), 7.09 (d, J=8.4 Hz, 1H), 6.84 (d, J=8.0 Hz, 1H), 6.77 (d, J=8.1 Hz, 1H), 6.68 (t, J=7.3 Hz, 1H), 6.54 (dd, J=7.6, 1.7 Hz, 1H), 6.50 (d, J=7.6 Hz, 1H), 4.09-4.02 (m, J=6.9 Hz, 1H), 3.27 (dq, J=15.1, 7.4 Hz, 1H), 2.99 (d, J=13.1 Hz, 1H), 2.72 (dq, J=15.0, 7.4 Hz, 1H), 2.30 (d, J=13.1 Hz, 1H), 2.16-2.04 (m, 4H), 1.80-1.76 (m, 1H), 1.62 (t, J=7.4 Hz, 3H), 1.52 (s, 3H), 1.38 (d, J=6.7 Hz, 3H), 1.26 (d, J=6.7 Hz, 3H), 1.23 (s, 3H), 0.77 (t, J=7.4 Hz, 3H).

$^{13}$C NMR (101 MHz, CDCl$_3$): δ (ppm) 270.5, 253.8, 154.6, 153.7, 145.5, 143.0, 140.9, 140.9, 139.6, 139.1, 131.2, 129.7, 129.2 (2C), 128.1, 127.8 (2C), 127.7, 127.1, 126.1, 125.4, 124.6, 122.4, 121.5, 120.9, 114.0, 81.0, 78.4, 62.3, 49.0, 30.6, 29.7, 28.9, 28.9, 25.4, 21.3, 20.3, 14.4, 11.6.

Use of the Compounds of the Invention as Catalysts—Application in Asymmetric Olefin Metathesis

Asymmetric Ring Opening Cross Metathesis (AROCM)

Reagents Used for Asymmetric Ring Opening/Cross Metathesis (AROCM)

Cis-5-Norbornene-endo-2,3-dicarboxylic anhydride (S1a) and Cis-5-Norbornene-endo-2,3-dicarboxylic anhydride (S3a) were purchased from TCI and recrystallized in cyclohexane prior to use. (1R,4S,5R,6S)-5,6-bis(((tert-butyldimethylsilyl)oxy) methyl)bicyclo[2.2.1]hept-2-ene (S1d)(Kanaoka, S.; Grubbs, R. H. *Macromolecules* 1995, 28, 4707-4713), ((1R,2S,3R,4S)-bicyclo[2.2.1]hept-5-ene-2,3-diyl)bis (methylene) diacetate (S1e)(Goll, J. M.; Fillion, E. *Organometallics* 2008, 27, 3622-3625), (1R,4S,5R,6S)-5,6-bis((benzyloxy)methyl)bicyclo[2.2.1]hept-2-ene (S1f) (Liu, W.; Rajanbabu, T. V. *J. Org. Chem.* 2010, 75, 7636-7643), ((1R,2R,3S,4S)-bicyclo[2.2.1]hept-5-ene-2,3-diyl) dimethanol (S3b)(Polo, E.; Forlini, F.; Bertolasi, V.; Boccia, A. C.; Sacchi, M. C. *Adv. Synth. Catal.* 2008, 350, 1544-1556. https://doi.org/10.1002/adsc.200

800168) and (1-methylcycloprop-2-en-1-yl)benzene (S2) (Sherrill, W. M.; Kim, R.; Rubin, M. *Tetrahedron* 2008, 64, 8610-8617) were prepared according to literature procedures. Styrene, para-substituted styrenes and allyl acetate were distilled over activated molecular sieve (4 Å) and freeze-pump-thaw degassed prior to use.

General Procedure for AROCM

In a flame-dried Schlenk tube under Ar were placed the desired substrate (1 equiv) and styrene derivative or allyl acetate (5 equiv). The mixture was placed at the desired temperature. A solution of the catalyst in previously distilled and degassed desired solvent was prepared. The required amount of this solution was added and an additional amount of solvent was added to obtain a concentration of 0.15 M for the substrate. The green mixture was stirred at the indicated temperature for the indicated time. Once the reaction was complete, it was quenched with ethylvinylether. Product was isolated by column chromatography on silica gel.

Optimization of the Reaction Conditions: Solvent Screening

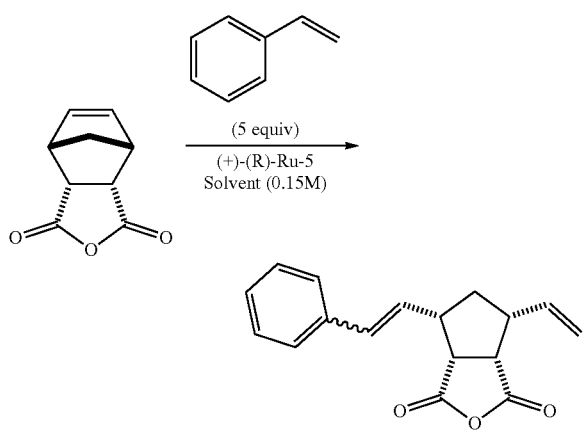

4-styryl-6-vinyltetrahydro-1H-cyclopenta[c]furan-1,3(3aH)-dione (P1a)

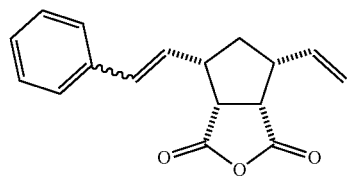

Chemical Formula: $C_{17}H_{16}O_3$
Molecular Weight: 268.31 g·mol$^{-1}$

The general procedure for AROCM was applied with S1a (32.6 mg, 0.20 mmol, 1 equiv), styrene (120 µL, 1.05 mmol, 5.25 equiv) and (+)-(R)-Ru-4b (7.4 mg, 0.01 mmol, 5 mol %) in the indicated solvent at 35° C. Conversion was monitored by TLC (eluent: Pentane:EtOAc, 6:4). The desired product P1a was obtained after column chromatography (eluent: Pentane:EtOAc, 10:0 to 9:1) as a colourless oil.

$^1$H NMR (400 MHz, CDCl$_3$) of E isomer (major product): δ (ppm) 7.42-7.36 (m, 2H), 7.35-7.29 (m, 2H), 7.28-7.21 (m, 1H), 6.52 (d, J=15.8 Hz, 1H), 6.30 (dd, J=15.8, 8.0 Hz, 1H), 6.03-5.92 (m, 1H), 5.24 (d, J=1.1 Hz, 1H), 5.20 (dt, J=6.7, 1.3 Hz, 1H), 3.62-3.49 (m, 2H), 3.21-3.11 (m, 1H), 3.11-3.00 (m, 1H), 2.14 (dt, J=13.0, 5.4 Hz, 1H), 1.57 (dt, J=12.9, 12.9 Hz, 1H).

$^{13}$C NMR (101 MHz, CDCl$_3$) of E isomer (major product): δ (ppm) 170.7, 136.8, 134.9, 132.4, 128.7, 127.9, 126.6, 126.5, 117.6, 50.0, 49.6, 46.9, 46.4, 36.7.

$[\alpha]_D^{25}$ of E isomer=−102 (c=0.00102 g/mL, CHCl$_3$, E isomer was separated from Z isomer on silica gel, eluent: Pentane:EtOAc 10:0 to 8:2. (92% ee)).

TABLE 1

Results of the solvent screening for AROCM with S1a, Styrene and (+)-(R)-Ru-4b

| Entry | Solvent | Time | Conv. (%) | Isolated Yield (%) | E:Z$^a$ | ee (%)$^b$ |
|---|---|---|---|---|---|---|
| 1 | THF | 2 days | >99 | 49 | 90:10 | 89 (R, S) |
| 2 | Me-THF | 2 days | >99 | 66 | 90:10 | 88 (R, S) |
| 3 | DCM | 2 days | >99 | 74 | 90:10 | 85 (R, S) |
| 4 | Toluene | 3 days | 90$^c$ | 34 | 90:10 | 87 (R, S) |
| 5 | Benzene | 3 days | 90$^c$ | 34 | 90:10 | 86 (R, S) |

$^a$E:Z ratio were determined by SFC on the crude mixture.
$^b$Enantiomeric purities on the E isomer were determined by SFC on chiral stationary phase after silica gel column chromatography in comparison with authentic racemic material.
$^c$Determined by $^1$H NMR with mesitylene as internal standard.

Analytical parameters: Method 1: Enantiomeric Excess was determined by SFC on Chiral stationary phase.

Flow: 2.0 mL/min

Pump A: liquid $CO_2$—Pump B: EtOH—Back Pressure Regulator: 150 bar

Column: IC: 150×3 mm×3 µm at 40° C.

Injection: 5 µL-Run time: 16 min

Detection PDA between 200 and 450 nm (6.25 Hz)—constant: 0.640 s

| Time (min) | % Pump A | % Pump B |
|---|---|---|
| 0.01 | 96.5 | 3.5 |
| 10.00 | 96.5 | 3.5 |
| 10.50 | 70 | 30 |
| 13.50 | 70 | 30 |
| 14.00 | 96.5 | 3.5 |
| 16.00 | 96.5 | 3.5 |

Catalyst Screening

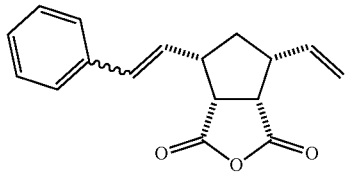

4-styryl-6-vinyltetrahydro-1H-cyclopenta[c]furan-1,3(3aH)-dione (P1a)

Chemical Formula: $C_{17}H_{16}O_3$
Molecular Weight: 268.31 g·mol$^{-1}$

The general procedure for AROCM was applied with S1a (48.8 mg, 0.30 mmol, 1 equiv) and styrene (170 µL, 1.5 mmol, 5 equiv) with the desired catalyst at the indicated loading in THF the indicated time at the indicated temperature. Conversion was monitored by TLC (eluent: Pentane:EtOAc, 6:4). The desired product P1a was obtained after column chromatography (eluent: Pentane:EtOAc, 10:0 to 9:1) as a colourless oil.

TABLE 2

Ru-catalyst screening for AROCM of S1a and styrene in THF

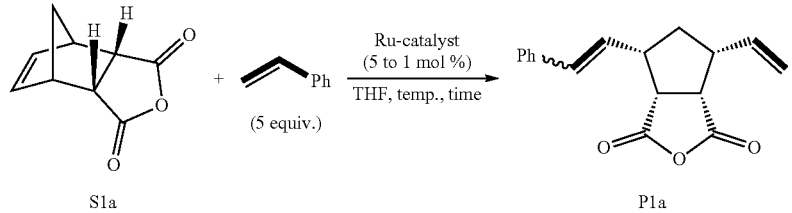

| Entry | Ru-cat (mol %) | T (° C.)/Time | conv.[a] (yield)[b] (%) | E/Z ratio[c] | ee E (%)[d] | ee Z (%)[e] |
|---|---|---|---|---|---|---|
| 1 | (S)-Ru-1a (5) | 50/3 d | 99 (13) | 80/20 | 85 (S,R) | |
| 2 | (S)-Ru-1b (5) | 50/24 h | 99 (53) | 85/15 | 87 (S,R) | |
| 3 | (S)-Ru-1b (5) | 35/2 d | 99 (41) | 85/15 | 90 (S,R) | 17 |
| 4 | (R)-Ru-1b (5) | 35/2 d | 99 (58) | 85/15 | −92 (R,S)[f] | |
| 5 | (R)-Ru-1b (5) | rt/2 d | 0 | nd | nd | |
| 6 | (R)-Ru-2a (5) | 50/6 d | <10 (nd) | 80/20 | nd | |
| 7 | (R)-Ru-2b (5) | 50/6 d | <15 (nd) | 80/20 | nd | |
| 8 | (R)-Ru-3b (5) | 35/2 d | 99 (55) | 90/10 | −92 (R,S) | |
| 9 | (R)-Ru-4b (5) | 50/24 h | 99 (63) | 90/10 | −83 (R,S) | |
| 10 | (R)-Ru-4b (5) | 35/2 d | 99 (49) | 90/10 | −89 (R,S) | |
| 11 | (R)-Ru-5b (5) | 50/5 d | 99 (18) | 85/15 | −47 (R,S) | |
| 12 | (R)-Ru-6b (5) | 35/5 d | 60 (45) | 95/5 | −79 (R,S) | |
| 13 | 1$^{st}$-Ru-7b (5) | 35/1 d | 99 (57) | 96/4 | −86 (R,S) | |
| 14 | (R)-Ru-8a (1) | 70/10 min | 99 (70) | 85/15 | −47 (R,S) | |
| 15 | (R)-Ru-8a (1) | rt/1 h | 99 (64) | 85/15 | −60 (R,S) | |
| 16 | (R)-Ru-8b (1) | 70/5 min | 99 (52) | 85/15 | −49 (R,S) | |
| 17 | (R)-Ru-8b (5) | 50/15 min | 99 (57) | 85/15 | −49 (R,S) | |
| 18 | (R)-Ru-8b (5) | rt/15 min | 99 (58) | 85/15 | −56 (R,S) | |
| 19 | (R)-Ru-8b (1) | rt/15 min | 99 (57) | 85/15 | −61 (R,S) | 6 |
| 20 | (R)-Ru-8b (1) | 0/45 min | 99 (61) | 85/15 | −65 (R,S) | 10 |
| 21 | (R)-Ru-8b (1) | −10/100 min | 99 (56) | 85/15 | −68 (R,S) | 13 |
| 22 | (R)-Ru-8b (1) | −20/4 h | 99 (54) | 85/15 | −70 (R,S) | 16 |
| 23[g] | (R)-Ru-8b (1) | −30/24 h | 99 (52) | 80/20 | −71 (R,S) | 18 |
| 24[g] | (R)-Ru-8b (1) | −50/24 h | 0 | nd | nd | |
| 25 | (R)-Ru-9a (1) | rt/6 h | 99 (47) | 75/25 | −62 (R,S) | |
| 26 | (S)-Ru-9b (1) | rt/1.5 h | 99 (37) | 75/25 | 62 (S,R) | |
| 27 | (R)-Ru-10b (1) | rt/30 min | 99 (66) | 90/10 | −74 (R,S) | |
| 28 | (R)-Ru-10b (1) | −20/20 h | 99 (63) | 90/10 | −80 (R,S) | |
| 29 | (R)-Ru-11b (1) | rt/15 min | 99 (70) | 80/20 | −58 (R,S) | |
| 30 | (R)-Ru-12b (1) | rt/1 h | 99 (75) | 99/1 | −49 (R,S) | |
| 31 | (R)-Ru-12b (1) | −20/24 h | 0 | nd | nd | |
| 32 | (R)-Ru-8c (5) | 55/4 d | 20 (nd) | 80/20 | −66 (R,S) | |

[a]Conversions were monitored by TLC and $^1$H NMR spectroscopy analysis.

[b]Isolated yields after column chromatography on silica gel.

[c]E/Z ratio determined by SFC on the crude mixture.

[d]ee determined on the E isomer by SFC on a chiral stationary phase.

[e]ee of Z product: 17%.

Absolute configuration determined on the corresponding diol by comparison with the literature.

[f][α]$^{25}_D$ (CHCl$_3$, c = 1 g/L, 92% ee) = −10.

Reactions performed in 2-MeTHF (0.15M)

Analytical parameters for ee determination by SFC: Enantiomeric Excess was determined by SFC on Chiral stationary phase following the Method 1.

Analytical parameters for ee determination by HPLC: Method 11:

Enantiomeric Excess was determined by HPLC on Chiral stationary phase.

Column OJ-H (250×4.6 mm, 5 μm)
Mobile phase: Hexanes:iPrOH 70:30
Flow rate: 0.75 mL/min
Detection at 254 nm.

Substrate Scope

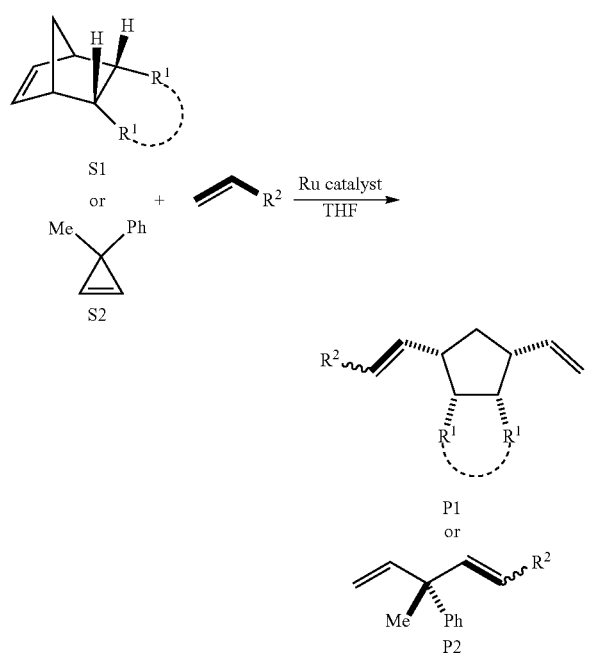

4-(4-methoxystyryl)-6-vinyltetrahydro-1H-cyclopenta[c]furan-1,3(3aH)-dione (P1b)

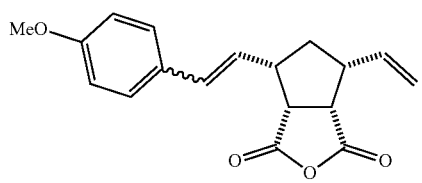

Chemical Formula: $C_{18}H_{18}O_4$
Molecular Weight: 298.34 g·mol$^{-1}$

The general procedure for AROCM reactions was followed using S1a (32.8 mg, 0.20 mmol, 1 equiv), 4-Vinylanisole (130 μL, 1.0 mmol, 5 equiv) and a stock solution of the desired complex. The reaction was stirred the indicated time at the indicated temperature. Completion was monitored by $^1$H NMR spectroscopy. The desired product P1b was obtained after column chromatography (eluent: Pentane:EtOAc, 10:0 to 8:2) as a colourless oil.

$^1$H NMR (400 MHz, CDCl$_3$) of E isomer (major product): δ (ppm) 7.35-7.28 (m, 2H), 6.87-6.82 (m, 2H), 6.50-6.42 (m, 1H), 6.14 (dd, J=15.7, 8.1 Hz, 1H), 6.04-5.91 (m, 1H), 5.23 (d, J=1.1 Hz, 1H), 5.21-5.13 (m, 1H), 3.81 (s, 3H), 3.59-3.46 (m, 2H), 3.20-3.09 (m, 1H), 3.09-2.98 (m, 1H), 2.12 (dt, J=12.9, 5.5 Hz, 1H), 1.55 (dt, J=12.9, 12.9 Hz, 1H).

$^{13}$C NMR (101 MHz, CDCl$_3$) of E isomer (major product): δ (ppm) 170.7, 159.3, 134.9, 131.7, 129.5, 127.7, 124.1, 117.3, 114.0, 55.3, 49.9, 49.4, 46.8, 46.3, 36.7.

[α]$_D^{25}$ of E isomer=−84 (c=0.001 g/mL, CHCl$_3$, E isomer separated from Z isomer on silica gel, eluent: Pentane:EtOAc, 10:0 to 8:2 (74% ee)).

TABLE 3

Results of AROCM with S1a and 4-Vinylanisole

| Entry | Ru-cat (mol %) | T (° C.) | Time | Conv.$^a$ (%) | Isolated Yield (%) | E:Z$^b$ | ee (%)$^c$ |
|---|---|---|---|---|---|---|---|
| 1 | (R)-Ru-1b (5) | 35 | 40 h | >99 | 62 | 90:10 | 74 |
| 2 | (R)-Ru-10b (1) | −20 | 20 h | >99 | 65 | 90:10 | 79 |

$^a$Determined by $^1$H NMR spectroscopy.
$^b$E:Z ratio were determined by SFC on the crude mixture.
$^c$Enantiomeric purities of the E isomer were determined by SFC with chiral stationary phase after silica gel column chromatography in comparison with authentic racemic material.

The enantiomeric purity was determined on the E isomer of the crude mixture by SFC with chiral stationary phase (following the method 2) in comparison with authentic racemic material Analytical parameters: Method 2: Enantiomeric Excess was determined by SFC on Chiral stationary phase.

Flow: 2.0 mL/min
Pump A: liquid CO2—Pump B: iPrOH—Back Pressure Regulator: 100 bar
Column: ID: 150×3 mm×3 μm at 40° C.
Injection: 5 μL-Run time: 15 min
Detection PDA between 200 and 450 nm (6.25 Hz)—constant: 0.640 s

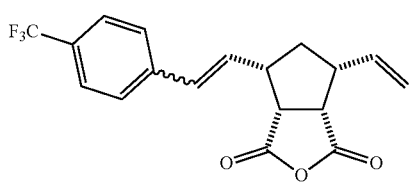

Chemical Formula: $C_{18}H_{15}F_3O_3$
Molecular Weight: 336.31 g·mol$^{-1}$ 4-(4-(trifluoromethyl)styryl)-6-vinyltetrahydro-1H-cyclopenta[c]furan-1,3(3aH)-dione (P1c)

| Time (min) | % Pump A | % Pump B |
|---|---|---|
| 0.01 | 93 | 7 |
| 8.50 | 93 | 7 |
| 9.00 | 60 | 40 |
| 11.00 | 60 | 40 |
| 11.50 | 93 | 7 |
| 13.50 | Stop | Stop |

The general procedure for AROCM reactions was followed using S1a (32.8 mg, 0.20 mmol, 1 equiv), 1-(trifluoromethyl)-4-vinylbenzene (150 μL, 1.0 mmol, 5 equiv) and a stock solution of the desired complex. The reaction was stirred the indicated time at the indicated temperature. Completion of the reaction was monitored by $^1$H NMR spectroscopy. The desired product P1c was obtained after column chromatography (eluent: Pentane:EtOAc, 10:0 to 8:2) as a colourless oil.

$^1$H NMR (400 MHz, CDCl$_3$) of E isomer (major product): δ (ppm) 7.59 (d, J=8.2 Hz, 2H), 7.50 (d, J=8.1 Hz, 2H), 6.57 (d, J=15.8 Hz, 1H), 6.44 (dd, J=15.8, 7.6 Hz, 1H), 6.00 (ddd, J=16.5, 10.7, 7.4 Hz, 1H), 5.28-5.25 (m, 1H), 5.23 (dt, J=8.1, 1.2 Hz, 1H), 3.65-3.54 (m, 2H), 3.28-3.16 (m, 1H), 3.16-3.04 (m, 1H), 2.19 (dt, J=12.9, 5.4 Hz, 1H), 1.61 (dt, J=12.9, 12.9 Hz, 1H).

$^{19}$F NMR (376 MHz, CDCl$_3$) of E isomer (major product): δ (ppm) −62.5.

$^{13}$C NMR (101 MHz, CDCl$_3$) of E isomer (major product): δ (ppm) 170.7, 170.5, 134.7, 131.1, 129.4, 126.8, 125.7 (q, J$^3$=3.8 Hz, CF$_3$), 117.7, 50.0, 49.5, 46.9, 46.1, 36.4.

[α]$_D^{25}$ of E isomer=−101 (c=0.001 g/mL, CHCl$_3$, E isomer separated from Z isomer on silica gel, eluent: Pentane:EtOAc, 10:0 to 8:2 (80% ee)).

TABLE 4

Results of AROCM with S1a and 1-(trifluoromethyl)-4-vinylbenzene

| Entry | Ru-cat (mol %) | T (° C.) | Time | Conv.$^a$ (%) | Isolated Yield (%) | E:Z$^b$ | ee (%)$^c$ |
|---|---|---|---|---|---|---|---|
| 1 | (R)-Ru-1b (5) | 35 | 40 h | >99 | 41 | 90:10 | 80 |
| 2 | (R)-Ru-10b (1) | −20 | 24 h | 85 | 47 | 85:15 | 73 |

$^a$Determined by $^1$H NMR spectroscopy.
$^b$E:Z ratio were determined by SFC on the crude mixture.
$^c$Enantiomeric purities of the E isomer were determined by SFC with chiral stationary phase after silica gel column chromatography in comparison with authentic racemic material.

The enantiomeric purity was determined on the E isomer of the crude mixture by SFC with chiral stationary phase (following the method 3) in comparison with authentic racemic material.

Analytical parameters: Method 3: Enantiomeric Excess was determined by SFC on Chiral stationary phase.
Flow: 2.0 mL/min
Pump A: liquid CO2—Pump B: iPrOH—Back Pressure Regulator: 100 bar
Column: IA: 150×3 mm×3 μm at 40° C.

Injection: 5 μL-Run time: 15 min
Detection PDA between 200 and 450 nm (6.25 Hz)—constant: 0.640 s

| Time (min) | % Pump A | % Pump B |
|---|---|---|
| 0.01 | 93 | 7 |
| 6.00 | 93 | 7 |
| 6.50 | 60 | 40 |
| 8.50 | 60 | 40 |
| 9.00 | 93 | 7 |
| 11.00 | Stop | Stop |

(((3-styryl-5-vinylcyclopentane-1,2-diyl)bis(methylene))bis(oxy))bis(tert-butyldimethylsilane) (P1d)

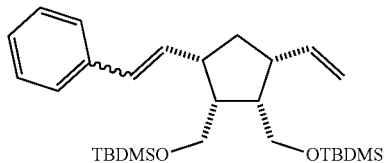

Chemical Formula: C$_{29}$H$_{50}$O$_2$Si$_2$
Molecular Weight: 486.89 g•mol$^{-1}$ The general procedure for AROCM reactions was followed using S1d (76.5 mg, 0.20 mmol, 1 equiv), styrene (120 μL, 1.0 mmol, 5 equiv) and a stock solution of the desired complex. The reaction was stirred the indicated time at the indicated temperature. Completion of the reaction was monitored by TLC (eluent: Pentane) and $^1$H NMR spectroscopy. The desired product P1d was obtained after column chromatography (eluent: Pentane) as a colourless oil.

$^1$H NMR (400 MHz, CDCl$_3$) of E isomer (major product): δ (ppm) 7.42-7.27 (m, 4H), 7.24-7.16 (m, 1H), 6.49-6.32 (m, 2H), 5.97 (ddd, J=16.9, 10.2, 8.4 Hz, 1H), 5.08-5.00 (m, 1H), 4.99-4.95 (m, 1H), 3.89-3.65 (m, 4H), 3.03-2.88 (m, 1H), 2.83-2.70 (m, 1H), 2.50-2.16 (m, 2H), 2.16-1.87 (m, 1H), 1.84-1.73 (m, 1H), 1.04-0.80 (m, 18H), 0.20−−0.04 (m, 12H).

$^{13}$C NMR (101 MHz, CDCl$_3$) of E isomer (major product): δ (ppm) 140.9, 138.0, 137.9, 133.2, 133.0, 129.6, 129.5, 128.7, 128.4, 126.7, 126.1, 114.0, 61.4, 61.3, 61.2, 48.4, 47.8, 45.5, 45.0, 44.9, 38.1, 26.1, 26.0, 18.3, 18.2, −5.3, −5.3, −5.4, −5.4.

TABLE 5

Results of AROCM with S1d and Styrene

| Entry | Ru-cat (mol %) | T (° C.) | Time | Conv.$^a$ (%) | Isolated Yield (%) | E:Z$^a$ | ee of E (%)$^b$ | ee of Z (%)$^b$ |
|---|---|---|---|---|---|---|---|---|
| 1 | (S)-Ru-2 (5) | 35 | 22 h | >99 | 94 | 94:6 | 74 | 31 |
| 2 | (S)-Ru-6b (5) | 35 | 22 h | >99 | 68 | 96:4 | 83 | nd |
| 3 | (R)-Ru-11b (1) | −20 | 15 h | >99 | 76 | 85:15 | 46 | 42 |

$^a$Determined by $^1$H NMR spectroscopy.
$^b$Enantiomeric purities of each isomer were determined by SFC with chiral stationary phase on the corresponding diol in comparison with authentic racemic material.

The enantiomeric purity was determined on the E and the Z isomer of the corresponding diol after TBDMS cleavage by SFC with chiral stationary phase (following the method 4) in comparison with authentic racemic material.

Analytical parameters: Method 4: Enantiomeric Excess was determined by SFC on Chiral stationary phase on the corresponding diol. TBDMS group was cleaved using TBAF (5 equiv) in THF. The mixture was stirred overnight. Water was added and the aq. layer was extracted with Et$_2$O twice.

1H), 6.19 (dd, J=15.7, 8.5 Hz, 1H), 5.88-5.77 (m, 1H), 5.12-5.00 (m, 2H), 4.25-4.12 (m, 2H), 4.12-4.04 (m, 2H), 3.05-2.92 (m, 1H), 2.91-2.73 (m, 1H), 2.59-2.50 (m, 2H), 2.25-2.09 (m, 1H), 2.05 (s, 3H), 1.99 (s, 3H), 1.70-1.34 (m, 1H).

$^{13}$C NMR (101 MHz, CDCl$_3$) of E isomer (major product): δ (ppm) 170.9, 170.8, 139.1, 137.2, 130.9, 130.8, 128.6, 128.6, 128.2, 127.2, 126.1, 115.7, 62.8, 62.7, 44.7, 44.6, 44.3, 44.2, 36.5, 21.1, 21.0.

TABLE 6

Results of AROCM with S1e and Styrene

| Entry | Ru-cat (mol %) | T (° C.) | Time | Conv.$^a$ (%) | Isolated Yield (%) | E:Z$^a$ | ee of E (%)$^b$ | ee of Z (%)$^b$ |
|---|---|---|---|---|---|---|---|---|
| 1 | (S)-Ru-1b (5) | 35 | 20 h | >99 | 62 | 85:15 | 83 | 23 |
| 2 | (R)-Ru-10b (1) | −20 | 15 h | >99 | 79 | 85:15 | 57 | 34 |

$^a$Determined by GC-MS.
$^b$Enantiomeric purities of each isomer were determined by SFC with chiral stationary phase on the corresponding diol in comparison with authentic racemic material.

Flow: 2.0 mL/min
Pump A: liquid CO2—Pump B: EtOH—Back Pressure Regulator: 150 bar at 60° C.
Column: IF: 150×3 mm×3 μm at 40° C.
Injection: 3 μL-Run time: 15 min

| Detection PDA between 200 and 450 nm (6.25 Hz) - constant: 0.640 s | | |
|---|---|---|
| Time (min) | % Pump A | % Pump B |
| 0.01 | 91 | 9 |
| 9.00 | 91 | 9 |
| 10.00 | 60 | 40 |
| 12.50 | 60 | 40 |
| 13.00 | 91 | 9 |
| 15.00 | 91 | 9 |

(3-styryl-5-vinylcyclopentane-1,2-diyl)bis(methylene) diacetate (P1e): The general procedure for AROCM reactions was

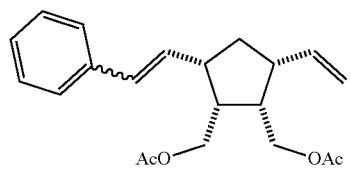

Chemical Formula: C$_{21}$H$_{26}$O$_4$
Molecular Weight: 342.44 g•mol$^{-1}$ followed using S1e (48.0 mg, 0.20 mmol, 1 equiv), styrene (120 μL, 1.0 mmol, 5 equiv) and a stock solution of the desired complex. The reaction was stirred the indicated time at the indicated temperature. Completion of the reaction was monitored by GC-MS. The desired product P1e was obtained after column chromatography (eluent: Pentane:Et$_2$O, 10:0 to 9:1) as a colourless oil.

$^1$H NMR (400 MHz, CDCl$_3$) of E isomer (major product): δ (ppm) 7.38-7.27 (m, 4H), 7.24-7.15 (m, 1H), 6.53-6.34 (m, The enantiomeric purity of both E and Z isomers were determined on the corresponding diol by SFC with chiral stationary phase (following the method 4) in comparison with authentic racemic material (ee of E isomer=83%; ee of Z isomer=23%).

Analytical parameters: K$_2$CO$_3$ (4 equiv) was added to P1e and the mixture was dissolved in MeOH (1 mL) and stirred overnight. MeOH was removed under vacuum, water was added and the aq. layer was extracted with Et$_2$O twice dried over MgSO$_4$ and concentrated under vacuum. Enantiomeric Excess was determined of the corresponding diol by SFC on Chiral stationary phase following the Method 4.

((((3-styryl-5-vinylcyclopentane-1,2-diyl)bis(methylene))bis(oxy)) bis(methylene))dibenzene (P1f)

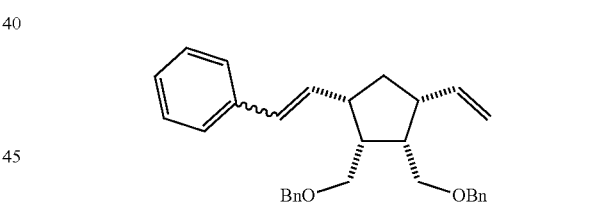

Chemical Formula: C$_{31}$H$_{34}$O$_2$
Molecular Weight: 438.61 g•mol$^{-1}$

The general procedure for AROCM reactions was followed using S1f (66.9 mg, 0.20 mmol, 1 equiv), styrene (120 μL, 1.0 mmol, 5 equiv) and a stock solution of the desired complex. The reaction was stirred the indicated time at the indicated temperature. Completion of the reaction was monitored by TLC (eluent: Pentane:Et$_2$O, 9:1) and $^1$H NMR spectroscopy. The desired product P1f was obtained after column chromatography (eluent: Pentane:Et$_2$O, 95:5) as a colourless oil.

$^1$H NMR (400 MHz, CDCl$_3$) of E isomer (major product): δ (ppm) 7.45-7.25 (m, 13H), 7.23-7.19 (m, 2H), 6.45-6.34 (m, 1H), 6.31-6.25 (m, 1H), 6.05-5.86 (m, 1H), 5.20-4.91 (m, 2H), 4.57-4.35 (m, 4H), 3.71-3.44 (m, 4H), 2.96 (dddd, J=8.8, 8.8, 8.8, 8.8 Hz, 1H), 2.80 (dddd, J=8.7, 8.7, 8.7, 8.7 Hz, 1H), 2.65-2.44 (m, 2H), 2.04 (ddd, J=12.8, 8.0, 8.0 Hz, 1H), 1.75 (dddd, J=12.9, 10.1, 10.1 Hz, 1H).

$^{13}$C NMR (101 MHz, CDCl$_3$) of E isomer (major product): δ (ppm) 140.6, 138.5, 137.9, 134.9, 133.2, 129.4, 128.9, 128.6, 128.4, 128.4, 128.3, 128.3, 128.1, 128.0, 127.9, 127.5, 127.5, 126.7, 126.5, 126.0, 114.5, 114.3, 73.4, 73.3, 68.9, 68.8, 46.1, 45.8, 45.7, 44.6, 37.9.

TABLE 7

Results of AROCM with S1f and Styrene

| Entry | Ru-cat (mol %) | T (° C.) | Time | Conv.$^a$ (%) | Isolated Yield (%) | E:Z$^b$ | ee of E (%)$^b$ |
|---|---|---|---|---|---|---|---|
| 1 | (S)-Ru-1b (5) | 35 | 22 h | >99 | 50 | 90:10 | 93 |
| 2 | (R)-Ru-10b (1) | −20 | 15 h | >99 | 65 | 75:25 | 52 |

$^a$Determined by $^1$H NMR spectroscopy.
$^b$E:Z ratio were determined by SFC on the crude mixture.
$^c$Enantiomeric purities of the E isomer were determined by SFC with chiral stationary phase after silica gel column chromatography in comparison with authentic racemic material.

The enantiomeric purity was determined on the E isomer of the crude mixture by SFC with chiral stationary phase (following the method 5) in comparison with authentic racemic material.

Analytical parameters: Method 5: Enantiomeric Excess was determined by SFC on Chiral stationary phase.

Flow: 2.0 mL/min

Pump A: liquid CO2—Pump C: DCM/MeOH 90/10-Back Pressure Regulator: 150 bar at 60° C.

Column: IB: 150×3 mm×3 μm at 40° C.

Injection: 5 μL-Run time: 20 min

Detection PDA between 200 and 450 nm (6.25 Hz)—constant: 0.640 s

| Time (min) | % Pump A | % Pump C |
|---|---|---|
| 0.01 | 95 | 5 |
| 11.50 | 95 | 5 |
| 13.00 | 84 | 16 |
| 14.00 | 84 | 16 |
| 15.00 | 60 | 40 |
| 17.00 | 60 | 40 |
| 17.50 | 95 | 5 |
| 20.00 | 95 | 5 |

(3-methylpenta-1,4-diene-1,3-diyl)dibenzene (P2a)

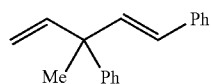

Chemical Formula: C$_{18}$H$_{18}$
Molecular Weight: 234.34 g·mol$^{-1}$

The general procedure for AROCM reactions was followed using S2 (42 μL, 0.3 mmol, 1 equiv), styrene (170 μL, 1.5 mmol, 5 equiv) and a stock solution of the desired complex. The reaction was stirred the indicated time at the indicated temperature. Completion of the reaction was monitored by GC-MS. The desired product P2a was obtained after column chromatography (eluent: Pentane) as a colourless oil.

$^1$H NMR (400 MHz, CDCl$_3$) of E:Z mixture (65:35 ratio): δ (ppm) 7.57-7.54 (m, 0.35H, E), 7.46-7.38 (m, 3H), 7.38-7.31 (m, 3H), 7.28-7.22 (m, 2H), 7.18-7.11 (m, 1H), 7.05-7.00 (m, 0.65H, E), 6.66 (d, J=12.6, 0.35H, Z), 6.50 (d, J=16.2 Hz, 0.65H, E), 6.41 (d, J=16.2 Hz, 0.65H, E), 6.20 (ddd, J=17.4, 10.5, 6.9 Hz, 1H), 5.93 (d, J=12.6 Hz, 0.35H, E), 5.23 (dd, J=10.6, 1.2 Hz, 0.65H, E), 5.14-5.05 (m, 1.3H, E+Z), 1.65 (s, 2H, E), 1.49 (s, 3H, E).

$^{13}$C NMR (101 MHz, CDCl$_3$) of E/Z: δ (ppm) 147.4 (E), 146.4 (E), 145.2 (Z), 145.1 (E), 138.2 (E), 137.5 (E), 137.1 (E+Z), 129.8 (E+Z), 129.0 (E+Z), 128.5 (E+Z), 128.2 (E+Z), 128.1 (E), 128.0 (Z), 127.3 (E+Z), 127.2 (E+Z), 127.2 (E+Z), 126.9 (E+Z), 126.3 (E), 126.3 (E), 125.9 (E+Z), 113.1 (E), 112.3 (E), 47.8 (E+Z), 28.6 (E), 25.6 (E).

TABLE 8

Results of AROCM with S2 and Styrene

| Entry | Ru-cat (mol %) | T (° C.) | Time | Conv.$^a$ (%) | Isolated Yield (%) | E:Z$^a$ | ee of E (%)$^b$ | ee of Z (%)$^b$ |
|---|---|---|---|---|---|---|---|---|
| 1 | (S)-Ru-1b (5) | 50 | 24 h | degradation | nd | nd | nd | nd |
| 2 | (S)-Ru-4b (5) | 50 | 24 h | degradation | nd | nd | nd | nd |
| 3 | (R)-Ru-8b (2) | rt | 3 h | >99 | 94 | 75:25 | 50 | 77 |
| 4 | (R)-Ru-10b (2) | rt | 3 h | >99 | 82 | 75:25 | 47 | 74 |
| 5 | (R)-Ru-11b (2) | rt | 3 h | >99 | 89 | 70:30 | 44 | 82 |
| 6$^c$ | (R)-Ru-11b (2) | rt | 3 h | >99 | 90 | 75:25 | 53 | 83 |

$^a$Determined by GC-MS
$^b$Enantiomeric purities of each isomer were determined by GC on chiral stationary phase by comparison with authentic racemic material.
$^c$Scale up: S2 (0.2 mL, 1.65 mmol, 1 equiv) and styrene (0.86 mL, 7.5 mmol, 4.5 equiv)

Analytical parameters: Method 6: Enantiomeric Excess of E isomer was determined by GC on Chiral stationary phase using the following method.
Column Chirasil-Dex 30 m×0.25 mm×0.25 μm
Carrier gas: Helium; u=30 cm/sec
Injection: 1 μL-split 20:1
Injector and detector's temperature: 250° C.
Run time: 155 min

| Rate | Temperature | Hold Time |
|---|---|---|
| — | 120.0 | 80.00 |
| 0.15 | 123.5 | 20.00 |
| 0.10 | 125.4 | 0.00 |
| 15.00 | 160.0 | 10.36 |

Analytical parameters: Method 7: Enantiomeric Excess of Z isomer was determined by GC on Chiral stationary phase using the following method.
Column Chirasil-Dex 30 m×0.25 mm×0.25 μm
Carrier gas: Helium; u=30 cm/sec
Injection: 1 μL-split 20:1
Injector and detector's temperature: 250° C.
Run time: 115 min

| Rate | Temperature | Hold Time |
|---|---|---|
| — | 115.0 | 80.00 |
| 0.20 | 119.0 | 0.00 |
| 10.00 | 170.0 | 9.90 |

$^1$H NMR (400 MHz, CDCl$_3$) of E:Z mixture (60:40 ratio): δ (ppm) 7.40-7.28 (m, 4H), 7.25-7.18 (m, 1H), 6.23-6.05 (m, 1H), 6.05-5.98 (m, 0.6H, E), 5.82 (dt, J=11.9, 1.8 Hz, 0.4H, E), 5.61-5.50 (m, 1H), 5.16 (dt, J=10.6, 1.3 Hz, 1H), 5.12-5.00 (m, 1H), 4.62 (dd, J=6.2, 1.4 Hz, 1H), 4.33-4.15 (m, 1H), 2.08 (s, 1.8H, E), 1.98 (s, 1.2H, E), 1.54 (s, 1.8H, E), 1.52 (s, 1.2H, E).

$^{13}$C NMR (101 MHz, CDCl$_3$) of E:Z mixture: δ (ppm) 170.8 (E), 170.7 (Z), 146.9 (E), 145.8 (E), 144.7 (E), 144.7 (E), 141.8 (E), 139.9 (E), 128.4 (Z, 2C), 128.2 (E, 2C), 127.1 (E, 2C), 126.9 (Z, 2C), 126.3 (E), 126.3 (E), 125.6 (E), 122.6 (E), 113.1 (E), 112.9 (E), 65.1 (E), 61.2 (E), 47.5 (E), 47.4 (E), 28.5 (E), 25.3 (E), 21.0 (E), 20.9 (E).

HRMS for C$_{15}$H$_{18}$O$_2$Na (M$^+$Na): calc.: 253.1199, found: 253.1201 (1 ppm).

Analytical parameters: Method 8: Enantiomeric Excess of each isomer was determined by HPLC on Chiral stationary phase on the corresponding alcohol. K$_2$CO$_3$ (4 equiv) was added to P2b and the mixture was dissolved in MeOH (1 mL) and stirred overnight. MeOH was removed under vacuum, water was added and the aq. layer was extracted with Et$_2$O twice, dried over MgSO$_4$, concentrated under vacuum.

Column OJ-H (250×4.6 mm, 5 μm)
Mobile phase: Hexanes:iPrOH 98:2
Flow rate: 1 mL/min
Detection at 220 nm.

TABLE 9

Results of AROCM with S2 and Allyl acetate

| Entry | Ru-cat (mol %) | T (° C.) | Time | Conv.$^a$ (%) | Isolated Yield (%) | E:Z$^a$ | ee of E (%)$^b$ | ee of Z (%)$^b$ |
|---|---|---|---|---|---|---|---|---|
| 1 | (R)-Ru-1b (5) | 50 | 18 h | >99 | 48 | 65:35 | 48 | 78 |
| 2 | (S)-Ru-4b (5) | 50 | 18 h | >99 | 32 | 55:45 | 48 | 85 |
| 3 | (S)-Ru-8b (2) | rt | 18 h | 98 | 30 | 55:45 | 35 | 69 |
| 4 | (R)-Ru-10b (2) | rt | 18 h | 90$^c$ | 54 | 55:45 | 37 | 69 |
| 5 | (R)-Ru-11b (2) | rt | 18 h | 98 | 52 | 45:55 | 34 | 80 |
| 6 | (R)-Ru-12b (1) | rt | 48 h | 75 | 28 | 60:40 | 34 | 35 |

$^a$Determined by GC-MS
$^b$Enantiomeric purities of each isomer were determined by HPLC on chiral stationary phase on the corresponding alcohol by comparison with authentic racemic material.
$^c$Determined by $^1$H NMR spectroscopy with mesitylene as internal standard.

4-methyl-4-phenylhexa-2,5-dien-1-yl acetate (P2b)

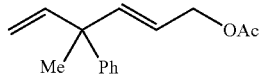

Chemical Formula: C$_{15}$H$_{18}$O$_2$
Molecular Weight: 230.31 g·mol$^{-1}$

The general procedure for AROCM reactions was followed using S2 (42 μL, 0.30 mmol, 1 equiv), Allyl acetate (160 μL, 1.5 mmol, 5 equiv) and a stock solution of the desired complex. The reaction was stirred the indicated time at the indicated temperature. Completion of the reaction was monitored by GC-MS. The desired product P2b was obtained after column chromatography (eluent: Pentane:Et$_2$O, 95:5) as a colourless oil.

((1R,2S,3S,5R)-3-styryl-5-vinylcyclopentane-1,2-diyl)dimethanol (P3b)

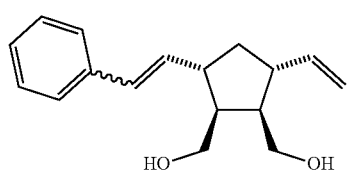

Chemical Formula: C$_{17}$H$_{22}$O$_2$
Molecular Weight: 258.36

Following the general procedure for AROCM reactions between S3b (31 mg, 0.2 mmol, 1 equiv) and styrene (120 μL, 1.0 mmol, 5 equiv) and a stock solution of the desired complex (0.002 mmol, 1 mol %). The reaction was stirred the 2 h at rt. Completion of the reaction and Z/E ratio were monitored by GC/MS. The desired product P3b was obtained after column chromatography (eluent: Pentane: EtOAc 10:0 to 7:3) as a colourless oil.

TABLE 10

AROCM between S3b and styrene

| Entry | Ru-cat (mol %) | Conv.$^a$ (%) | Isolated Yield (%) | E:Z$^a$ | ee of E (%)$^b$ | ee of Z (%)$^b$ |
|---|---|---|---|---|---|---|
| 3 | (R)-Ru-8b (1) | 99 | 29 | 35:65 | 39 | 52 |
| 6 | (S)-Ru-12b (1) | 99 | 42 | 93:7 | 48 | 8 |

$^1$H NMR (400 MHz, CDCl$_3$) of E/Z (40/60) mixture: δ (ppm) 7.41-7.28 (m, 3H), 7.26-7.19 (m, 2H), 6.51 (d, J=11.5 Hz, 0.6H), 6.41 (d, J=15.8 Hz, 0.4H), 6.14 (dd, J=15.8, 8.4 Hz, 0.4H), 5.85-5.71 (m, 1H), 5.55 (dd, J=11.5, 10.1 Hz, 0.6H), 5.11-4.95 (m, 2H), 3.88-3.53 (m, 4H), 3.38 (br s, 2H), 2.86-2.70 (m, 0.6H), 2.45-2.31 (m, 0.4H), 2.30-2.09 (m, 3H), 2.06-1.97 (m, 1H), 1.49-1.34 (m, 1H).

Analytical parameters: Method 10: Enantiomeric Excess was determined by HPLC on Chiral stationary phase.
Column OD-3 (250×4.6 mm, 3 μm)
Mobile phase: Hexanes:iPrOH 98:2
Flow rate: 1 mL/min-Detection at 254 nm.
Asymmetric Cross Metathesis (ACM)
Reagents Used for Asymmetric Cross Metathesis (ACM)
Tert-butyl(penta-1,4-dien-3-yloxy)dimethylsilane (S4) was prepared according to literature procedure (Giudici, R. E.; Hoveyda, A. H. *J. Am. Chem. Soc.* 2007, 129, 3824-3825. https://doi.org/10.1021/ja070187v) and filtered over basic alumina prior to use. Allyl acetate was distilled over activated molecular sieve (4 Å) and freeze-pump-thaw degassed prior to use.

Procedure for ACM

The substrate S4 (51.3 mg, 0.26 mmol, 1.0 equiv) and Allyl acetate (130 μL, 1.21 mmol, 4.6 equiv) were placed in flame dried Schlenk previously charged with Ar. The complex (S)-Ru-4b (8.9 mg, 0.012 mmol, 4.6 mol %) was added in solution in THF (1.5 mL). The mixture was stirred at 50° C. for 6 h. The reaction was monitored by GC-MS. Ethylvinylether was added to quench the reaction. Volatiles were removed under vacuum. The crude mixture is purified by column chromatography (eluent: Pentane:EtOAc 8:2).

4-((tert-butyldimethylsilyl)oxy)hexa-2,5-dien-1-yl acetate (P3)

Chemical Formula: C$_{14}$H$_{26}$O$_3$Si
Molecular Weight: 270.44 g·mol$^{-1}$

Following the procedure for ACM reactions, the desired product P4 was obtained after column chromatography (eluent: Pentane:EtOAc 10:0 to 8:2) as a colourless oil (29.2 mg, 42% yield). The E/Z ratio was determined by GC on the crude mixture (90/10).

$^1$H NMR (400 MHz, CDCl$_3$) of E isomer (major product): δ (ppm) 5.85-5.72 (m, 3H), 5.22 (ddd, J=17.1, 1.6, 1.6 Hz, 1H), 5.08 (ddd, J=10.3, 1.5, 1.5 Hz, 1H), 4.68-4.57 (m, 1H), 4.59-4.53 (m, 2H), 2.06 (s, 3H), 0.91 (s, 9H), 0.06 (s, 6H).

$^{13}$C NMR (101 MHz, CDCl$_3$) of E isomer (major product): δ (ppm) 170.9, 139.9, 136.6, 123.5, 114.3, 73.7, 64.5, 26.0, 21.1, 18.5, −4.5, −4.6.

The enantiomeric purity was determined after cleavage of the TBDMS group on the E isomer by GC with chiral stationary phase (following the method 9) in comparison with authentic racemic material (ee of E isomer: 50%).

Analytical parameters: Method 9: P4 was diluted in TBAF (1 M solution in THF, 2 equiv). The mixture was stirred overnight at rt. Solvent was removed under vacuum. The product was diluted in Et$_2$O and washed with saturated NaHCO$_3$. Organic layer was dried over MgSO$_4$. After evaporation of the solvent, the product was purified by silica gel column chromatography (eluent: pentane:EtOAc 10:0 to 8:2) and analysed by GC on chiral stationary phase.

Column: CP-Cyclodex B236M-dex: 50 m×0.25 mm, e=0.25 μm
Carrier gas Hélium: u=33 cm/s
Injection: 1 μL-split 2:1
Run time: 103.6 min

| Rate | Temperature | Hold Time |
|---|---|---|
| — | 103 | 75 |
| 0.5 | 108 | 0 |
| 20 | 180 | 15 |

Z-Selective Metathesis
Reagents Used for Z-Selective Metathesis

Norbornene (S1) was sublimed under Ar prior to use. cis-2-butene-1,4-diol and 1-decene were filtered through basic alumina, degassed by 3 Freeze/pump/thaw cycles, stored at −20° C. in a glove box prior to use.

ROMP

General Procedure for ROMP

In a flame dried microwave tube in a GB, the norbornene was placed (7 mg, 0.07 mmol, 1 equiv). The solution of Ru-8d in THF was added (0.004 mmol, 5 mol %). The mixture was stirred at rt for 3 h. Z/E ratio was determined by $^1$H NMR of the crude mixture (98/2).

Cross Metathesis

General Procedure for Cross Metathesis

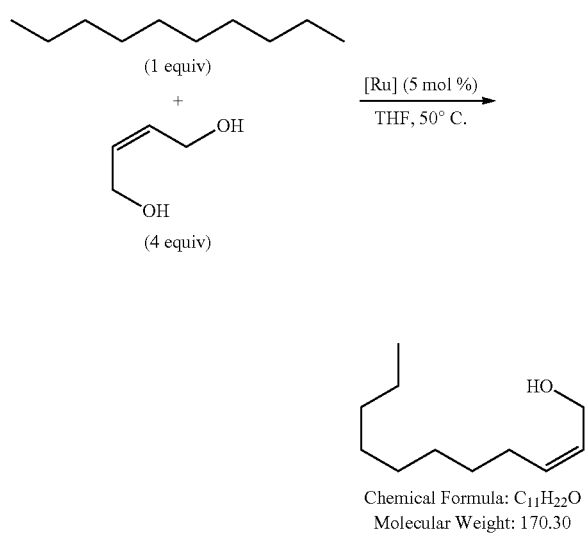

Chemical Formula: $C_{11}H_{22}O$
Molecular Weight: 170.30

General procedure with isolated thiolate complex: In a flame dried microwave tube in a GB, 1-decene (28 μL, 0.15 mmol, 1 equiv), cis-2-butene-1,4-diol (49 μL, 0.60 mmol, 4 equiv) and trimethoxybenzene (IS, 8.4 mg, 0.05, 0.34 equiv). The solution of the desired complex (0.007 mmol, 5 mol %). in THF was added. The mixture was stirred out of the GB at 50° C. for 16 h. The reaction was quenched with EVE. Conversion and yield were determined by $^1$H NMR. Product was purified by column chromatography (eluent: pentane:Et$_2$O 9:1). Z/E ratio was determined by $^1$H NMR of the purified product. A purple fraction composed of complex degradation products were coeluted with the product, so the product was filtered over activated charcoal pipette, and submitted to a second purification by column chromatography (eluent: pentane:Et$_2$O 9:1).

General procedure with in-situ formation of the thiolate complex: Out of the glove box, IS—Ru were formed according to literature procedure.[21] In a flame-dried 4-mL vial under Ar, 1,4-dichlorocatechol dithiolate (8 mg, 0.038 mmol, 1.5 equiv) and Diethyl zinc solution (1 M in hexanes, 38 μL, 0.038 mmol, 1.5 equiv) were dissolved in THF (0.3 mL). The desired complex (0.025 mmol, 1 equiv) was added. The green mixture was stirred 20 min at rt and turned to brown. This freshly prepared solution of catalyst was used in the flow reaction without further purification. In a flame dried microwave tube under Ar, 1-decene (28 μL, 0.15 mmol, 1 equiv), cis-2-butene-1,4-diol (49 μL, 0.60 mmol, 4 equiv) and trimethoxybenzene (IS, 8.4 mg, 0.05, 0.34 equiv). The previously prepared solution of the desired complex (0.007 mmol, 5 mol %) was added. The mixture was stirred at 50° C. for 16 h. The reaction was quenched with EVE. Conversion and yield were determined by $^1$H NMR. Product was purified by column chromatography (eluent: pentane:Et$_2$O 9:1). Z/E ratio was determined by $^1$H NMR of the purified product. A purple fraction composed of complex degradation products were coeluted with the product, so the product was filtered over activated charcoal pipette, and submitted to a second purification by column chromatography (eluent: pentane:Et$_2$O 9:1).

TABLE 11

Z-CM between diol and 1-decene

| Entry | Catalyst | NMR Conv. (%) | NMR yield (%) | Isolated yield (%) | Z/E ratio |
|---|---|---|---|---|---|
| 1 | Ru-8d | 35 | 31 | 26 | 98/2 |
| 2 | Ru-8e | 33 | 22 | 21 | 98/2 |
| 3 | IS—Ru-8e | 38 | 25 | 24 | 99/1 |
| 4 | IS—Ru-13b | 28 | 26 | 20 | 88/12 |

$^1$H NMR of Z-isomer (400 MHz, CDCl$_3$) δ (ppm) 5.73-5.47 (m, 2H), 4.21 (d, J=6.1 Hz, 2H), 2.20-2.01 (m, 2H), 1.48-1.18 (m, 13H), 0.98-0.81 (m, 3H).

$^{13}$C NMR of Z-isomer (101 MHz, CDCl$_3$) δ (ppm) 133.3, 128.3, 58.6, 31.9, 29.6, 29.4, 29.3, 29.2, 27.4, 22.7, 14.1.

HRMS for C$_{11}$H$_{22}$ONa calc.: 193.15629, found: 193.1562 (0 ppm). Source: ESI.

Z-Enantioselective Metathesis

Reagents Used for Z-Enantioselective Metathesis

Cis-5-Norbornene-endo-2,3-dicarboxylic anhydride (S3a) were purchased from TCI and recrystallized in cyclohexane prior to use. ((1R,2R,3S,4S)-bicyclo[2.2.1]hept-5-ene-2,3-diyl)dimethanol (S3b)(Polo, E.; Forlini, F.; Bertolasi, V.; Boccia, A. C.; Sacchi, M. C. *Adv. Synth. Catal.* 2008, 350, 1544-1556. https://doi.org/10.1002/adsc.200800168), (1R,4S,5S,6R)-5,6-bis(((tert-butyldimethylsilyl)oxy) methyl)bicyclo[2.2.1]hept-2-ene (S3d) (Kanaoka, S.; Grubbs, R. H. *Macromolecules* 1995, 28, 4707-4713. https://doi.org/10.1021/ma00117a050), ((1R,2R,3S,4S)-bicyclo[2.2.1]hept-5-ene-2,3-diyl)bis (methylene) diacetate (S3e) (Goll, J. M.; Fillion, E. *Organometallics* 2008, 27, 3622-3625. https://doi.org/10.1021/om800390w), (1R,4S,5S,6R)-5,6-bis((benzyloxy)methyl) bicycle[2.2.1]hept-2-ene (S3f) (Liu, W.; Rajanbabu, T. V. *J. Org. Chem.* 2010, 75, 7636-7643. https://doi.org/10.1021/jo1015135) were prepared according to literature procedures. Styrene and para-substituted styrenes were distilled over activated molecular sieve (4 Å) and freeze-pump-thaw degassed prior to use.

General Procedure with Isolated Thiolate Complex

In a flame dried microwave tube in a GB, the desired exo-norbornene derivative (0.2 mmol, 1 equiv), styrene (0.46 mL, 5.0 mmol, 20 equiv) were dissolved in THF. The solution of the desired complex (0.01 mmol, 5 mol %) in THF was added. The mixture was stirred at rt for the indicated time. The reaction was quenched with EVE. Conversion was monitored by $^1$H NMR. Z/E ratio were determined on the crude mixture. Product was purified by column chromatography.

General Procedure with In-Situ Formation of the Thiolate Complex

Out of the glove box, IS—Ru were formed according to literature procedure (Müller, D. S.; Curbet, I.; Raoul, Y.; Le Nôtre, J.; Baslé, O.; Mauduit, M. *Org. Lett.* 2018, 20, 6822-6826. https://doi.org/10.1021/acs.orglett.8b02943): In a flame-dried 4-mL vial under Ar, 1,4-dichlorocatechol dithiolate (8 mg, 0.038 mmol, 1.5 equiv) and Diethyl zinc solution (1 M in hexanes, 38 μL, 0.038 mmol, 1.5 equiv) were dissolved in THF (0.3 mL). The desired complex (0.025 mmol, 1 equiv) was added. The green mixture was stirred 20 min at rt and turned to brown. This freshly prepared solution of catalyst was used in the flow reaction without further purification. In a flame dried microwave tube in a GB, the desired exo-norbornene derivative (0.2 mmol, 1 equiv), styrene (0.46 mL, 5.0 mmol, 20 equiv) were dissolved in THF. The previously prepared solution of the desired complex (0.01 mmol, 5 mol %) was added. The mixture was stirred at rt for the indicated time. The reaction was quenched with EVE. Conversion was monitored by $^1$H NMR. Z/E ratio were determined on the crude mixture. Product was purified by column chromatography.

((1R,2S,3S,5R)-3-Z-styryl-5-vinylcyclopentane-1,2-diyl)dimethanol (P3b)

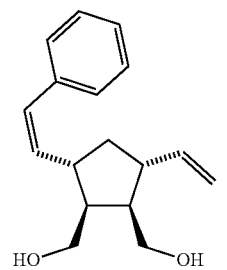

Chemical Formula: $C_{17}H_{22}O_2$
Molecular Weight: 258.36

Following the general procedure for AROCM reactions between S3b (31 mg, 0.2 mmol, 1 equiv) and styrene (0.46, 5.0 mmol, 20 equiv) and the desired complex solution. The reaction was stirred the indicated time at rt. Completion of the reaction and Z/E ratio were monitored by GC/MS. The desired product P3b was obtained after column chromatography (eluent: Pentane:EtOAc 10:0 to 7:3) as a colourless oil.

(3aS,4S,6R,6aR)-4-((Z)-styryl)-6-vinyltetrahydro-1H-cyclopenta[c]furan-1,3(3aH)-dione (P3a)

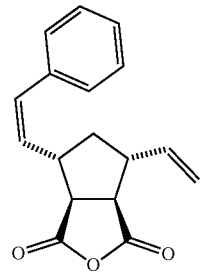

Chemical Formula: $C_{17}H_{16}O_3$
Molecular Weight: 268.31

Following the general procedure for AROCM reactions between S3a (32.7 mg, 0.2 mmol, 1 equiv) and styrene (0.46, 5.0 mmol, 20 equiv) and complex solution IS—(R)-Ru-10e (0.01 mmol, 5 mol %). The reaction was stirred 1 h at rt. Completion (99%) of the reaction and Z/E ratio (99/1) were

TABLE 12

Z-Ru-catalyst screening for Z-AROCM of S3b and styrene in THF

| Entry | Ru-cat (mol %) | T (° C.)/ Time | conv.$^a$ (yield)$^b$ (%) | E/Z ratio$^c$ | ee E (%)$^d$ | ee Z (%)$^d$ |
|---|---|---|---|---|---|---|
| 1 | (S)-Ru-8d | rt/2 h | 99 (26) | 1/99 | | 55 |
| 2 | IS-(S)-Ru-8d | rt/2 h | 99 (26) | 1/99 | | 55 |
| 3 | IS-(R)-Ru-8e | rt/30 min | 99 (20) | 1/99 | | 55 |
| 4 | IS-(S)-Ru-10e | rt/30 min | 99 (44) | 1/99 | | 57 |
| 5 | IS-(S)-Ru-11e | rt/30 min | 99 (31) | 1/99 | | 56 |
| 6 | IS-(S)-Ru-12e | rt/30 min | 99 (38) | 87/13 | 46 | 16 |

$^a$Conversions were monitored by GC/MS.
$^b$Isolated yields after column chromatography.
$^c$E/Z ratio determined by GC/MS.
$^d$ee determined by HPLC on a chiral stationary phase.

$^1$H NMR (400 MHz, CDCl$_3$) of Z isomer: δ (ppm) 7.39-7.30 (m, 2H), 7.30-7.21 (m, 3H), 6.51 (d, J=11.5 Hz, 1H), 5.84-5.71 (m, 1H), 5.55 (dd, J=11.6, 10.1 Hz, 1H), 5.09-4.96 (m, 2H), 3.69-3.55 (m, 4H), 3.14 (br s, 2H), 2.84-2.71 (m, 1H), 2.30-2.14 (m, 3H), 2.03 (dt, J=12.4, 6.2 Hz, 1H), 1.39 (dt, J=12.4, 11.2 Hz, 1H).

$^{13}$C NMR (101 MHz, CDCl$_3$) of Z isomer: δ (ppm) 141.4, 137.4, 135.8, 129.8, 128.5 (2C), 128.3 (2C), 126.7, 114.5, 62.0 (2C), 50.5, 48.5, 46.3, 40.1, 39.8.

Analytical parameters: Method 10: Enantiomeric Excess was determined by HPLC on Chiral stationary phase.

Column OD-3 (250×4.6 mm, 3 μm)

Mobile phase: Hexanes:iPrOH 98:2

Flow rate: 1 mL/min

Detection at 254 nm.

monitored by GC/MS. The desired product P3a was obtained after column chromatography (eluent: Pentane: EtOAc 10:0 to 8:2) as a colourless oil (30 mg, 56% yield).

$^1$H NMR (400 MHz, CDCl$_3$) of Z isomer: δ (ppm) 7.42-7.34 (m, 2H), 7.32-7.26 (m, 3H), 6.66 (d, J=11.4 Hz, 1H), 5.97-5.84 (m, 1H), 5.60 (dd, J=11.3, 9.8 Hz, 1H), 5.29-5.15 (m, 2H), 3.54-3.41 (m, 1H), 3.40-3.28 (m, 2H), 2.90 (d, J=14.3 Hz, 1H), 2.21 (dt, J=12.4, 6.0 Hz, 1H), 1.68 (dt, J=12.9, 11.2 Hz, 1H).

Analytical parameters: Method 11: Enantiomeric Excess was determined by HPLC on Chiral stationary phase; ee=68%.

Column OJ-H (250×4.6 mm, 5 μm)

Mobile phase: Hexanes:iPrOH 70:30

Flow rate: 0.75 mL/min

Detection at 254 nm.

((((1R,2S,3S,5R)-3-((Z)-styryl)-5-vinylcyclopentane-1,2-diyl)bis(methylene))bis(oxy))bis(tert-butyldimethylsilane) (P3d)

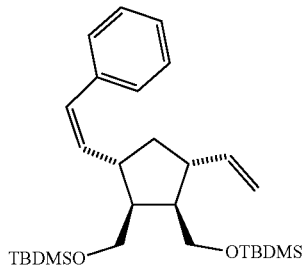

Chemical Formula: $C_{29}H_{50}O_2Si_2$
Molecular Weight: 486.89

Following the general procedure for AROCM reactions between S3d (80.1 mg, 0.21 mmol, 1 equiv) and styrene (0.46, 5.0 mmol, 19 equiv) and complex solution IS—(S)-Ru-10e (0.01 mmol, 5 mol %). The reaction was stirred 30 min at rt. Completion (99%) of the reaction and Z/E ratio (95/5) were monitored by $^1$H NMR. The desired product P3d was not isolated directly. Cleavage of the TBDMS group was performed with TBF (1 mmol, 5 equiv) at rt overnight. The product was extracted with $Et_2O$ (3×5 mL), dried over $MgSO_4$, and concentrated under vacuum. The corresponding diol was isolated by column chromatography (eluent: Pentane:EtOAc 10:0 to 7:3) as a colourless oil (20 mg, 36% yield).

Analytical parameters: Enantiomeric Excess was determined by HPLC on chiral stationary phase using method 10; ee of Z=29%, ee of E=0%.
  Column OD-3 (250×4.6 mm, 3 μm)
  Mobile phase: Hexanes:iPrOH 98:2
  Flow rate: 1 mL/min
  Detection at 254 nm.

(((((1R,2S,3S,5R)-3-((Z)-styryl)-5-vinylcyclopentane-1,2-diyl)bis(methylene))bis(oxy))bis(me-thylene))dibenzene (P3e)

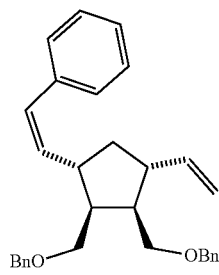

Chemical Formula: $C_{31}H_{34}O_2$
Molecular Weight: 438.61

Following the general procedure for AROCM reactions between S3e (66.4 mg, 0.2 mmol, 1 equiv) and styrene (0.46, 5.0 mmol, 20 equiv) and complex solution IS—(S)-Ru-10e (0.01 mmol, 5 mol %). The reaction was stirred 30 min at rt. Completion (99%) of the reaction and Z/E ratio (>98/2) were monitored by $^1$H NMR. The desired product P3e was obtained after column chromatography (eluent: Pentane: $Et_2O$ 100:0 to 98:2) as a colourless oil (29 mg, 33% yield).

$^1$H NMR (400 MHz, $CDCl_3$) of Z isomer: δ (ppm) 7.40-7.16 (m, 15H), 6.44 (d, J=11.6 Hz, 1H), 5.81 (ddd, J=17.1, 10.1, 8.0 Hz, 1H), 5.57 (dd, J=11.6, 10.2 Hz, 1H), 5.08-4.92 (m, 2H), 4.47-4.26 (m, 4H), 3.61-3.44 (m, 4H), 3.26-3.17 (m, 1H), 2.60-2.50 (m, 1H), 2.25-2.07 (m, 3H), 1.48-1.32 (m, 1H).

$^{13}$C NMR (101 MHz, $CDCl_3$) of Z isomer: δ (ppm) 142.5, 138.7, 138.6, 137.7, 137.0, 128.8, 128.6, 128.3, 128.2 (2C), 128.2 (2C), 127.6 (2C), 127.6 (2C), 127.4 (2C), 127.3, 126.5, 113.7, 73.0, 73.0, 70.2, 70.0, 48.3, 46.5, 46.5, 40.5, 40.3.

Analytical parameters: Enantiomeric Excess was determined by HPLC on Chiral stationary phase-method 12; ee of Z=50%.
  Column OD-3 (250×4.6 mm, 3 μm)
  Mobile phase: Hexanes:iPrOH 99.5:0.5
  Flow rate: 0.75 mL/min
  Detection at 254 nm.

((1R,2S,3S,5R)-3-((Z)-styryl)-5-vinylcyclopentane-1,2-diyl)bis(methylene) diacetate (P3f)

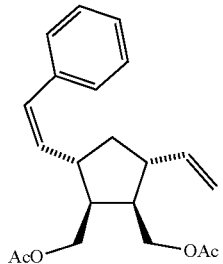

Chemical Formula: $C_{21}H_{26}O_4$
Molecular Weight: 342.44

Following the general procedure for AROCM reactions between S3f (68.0 mg, 0.2 mmol, 1 equiv) and styrene (0.46, 5.0 mmol, 20 equiv) and complex solution IS—(S)-Ru-10e (0.01 mmol, 5 mol %). The reaction was stirred overnight min at rt. Conversion (50%) of the reaction and Z/E ratio (98/2) were monitored by $^1$H NMR. The desired product P3f was obtained in mixture with starting material (1/1) after column chromatography (eluent: Pentane:$Et_2O$ 100:0 to 98:2) as a colourless oil.

Analytical parameters: Method 13: Enantiomeric Excess was determined by HPLC on Chiral stationary phase; ee of Z=50%.
  Column OD-3 (250×4.6 mm, 3 μm)
  Mobile phase: cyclohexane:iPrOH 99.7:0.3
  Flow rate: 1 mL/min
  Detection at 254 nm.

(3aS,4S,6R,6aR)-2-phenyl-4-((Z)-styryl)-6-vinyltetrahydrocyclopenta[c]pyrrole-1,3(2H,3aH)-dione (P3g)

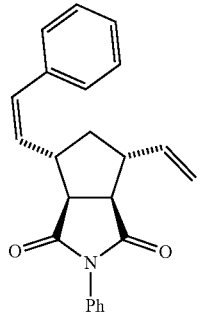

Chemical Formula: C₂₃H₂₁NO₂
Molecular Weight: 343.43

Following the general procedure for AROCM reactions between S3g (47.9 mg, 0.2 mmol, 1 equiv) and styrene (0.46, 5.0 mmol, 20 equiv) and complex solution IS—(R)-Ru-10e (0.01 mmol, 5 mol %). The reaction was stirred 1 h at rt. Completion (99%) of the reaction and Z/E ratio (97/3) were monitored by ¹H NMR. The desired product P3g was obtained after column chromatography (eluent: Pentane: EtOAc 10:0 to 9:1) as a white solid (57 mg, 83% yield).

¹H NMR (400 MHz, CDCl₃) of Z isomer: δ (ppm) 7.52-7.44 (m, 2H), 7.43-7.34 (m, 5H), 7.32-7.21 (m, 3H), 6.66 (dd, J=11.4, 0.8 Hz, 1H), 6.01 (ddd, J=17.0, 10.3, 6.6 Hz, 1H), 5.71 (dd, J=11.4, 9.9 Hz, 1H), 5.26 (dt, J=17.2, 1.3 Hz, 1H), 5.17 (dt, J=10.3, 1.2 Hz, 1H), 3.49-3.36 (m, 1H), 3.35-3.19 (m, 2H), 2.95-2.83 (m, 1H), 2.20 (dt, J=12.3, 6.0 Hz, 1H), 1.74 (dt, J=12.6, 11.1 Hz, 1H).

¹³C NMR (101 MHz, CDCl₃) of Z isomer: δ (ppm) 177.1, 176.8, 138.7, 136.8, 132.9, 131.2, 129.1 (2C), 128.7 (2C), 128.5, 128.4 (2C), 128.4, 127.0, 126.4 (2C), 116.0, 52.1, 51.1, 47.4, 42.8, 42.4.

Analytical parameters: Method 14: Enantiomeric Excess was determined by HPLC on Chiral stationary phase; ee=64%.

Column OD-3 (250×4.6 mm, 3 µm)
Mobile phase: Hexanes:iPrOH 90:10
Flow rate: 1 mL/min
Detection at 254 nm.

The invention claimed is:

1. An optically pure (+) or (−) enantiomer of a ruthenium complex having the following formula (I):

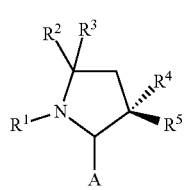

(I)

wherein:

R¹ is a (C₆-C₁₄)aryl group, a (C₁-C₆)alkyl group or a (C₈-C₂₀)cycloalkyl group, said aryl group being optionally substituted with at least one substituent chosen from the group consisting of: halogen, (C₆-C₁₀)aryl group, and (C₁-C₆)alkyl group, said alkyl group being optionally substituted with one or several phenyl group(s);

or R¹ is a —NR'ₐR'ᵦ group, R'ₐ and R'ᵦ being independently from each other selected from the group consisting of: H, (C₁-C₆)alkyl, and (C₆-C₁₀)aryl;

R² is H, a (C₆-C₁₀)aryl group or a (C₁-C₆)alkyl group;

R³ is a (C₁-C₆)alkyl group; or R² and R³ may together form, with the carbon atom carrying them, a (C₃-C₆)cycloalkyl;

R⁴ is selected from the following groups: (C₆-C₂₀)aryl, (C₁-C₁₀)alkyl, and (C₃-C₁₂)cycloalkyl group, said aryl group being optionally substituted with at least one substituent chosen from the group consisting of: (C₁-C₆)alkyl, optionally substituted with one or several phenyl group(s), (C₆-C₁₀)aryl(C₁-C₆)alkyl, and (C₆-C₁₀)aryl, optionally substituted with one or several substituents;

R⁵ is selected from the following groups: (C₆-C₂₀)aryl, (C₁-C₁₀)alkyl, (C₃-C₁₂)cycloalkyl, heteroaryl, (C₆-C₁₀)aryl(C₁-C₆)alkyl, and heteroaryl(C₁-C₆)alkyl, said aryl group being optionally substituted with at least one substituent chosen from the group consisting of: (C₁-C₆)alkyl, optionally substituted with one or several phenyl group(s), (C₆-C₁₀)aryl(C₁-C₆)alkyl, and (C₆-C₁₀)aryl, optionally substituted with one or several substituents;

with the proviso that R⁵ is different from R⁴;

A is either a group of formula (1) or a group of formula (2):

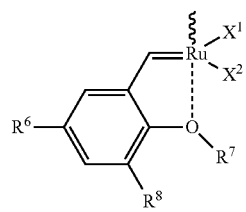

(1)

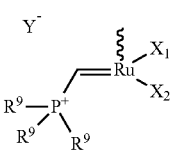

(2)

wherein:

X¹ is an halogen atom, a (C₁-C₆)alkoxy group or a —S—(C₆-C₁₀)aryl group;

X² is an halogen atom or a (C₁-C₆)alkoxy group;

or X¹ and X² may form together with the ruthenium atom carrying them a heterocycloalkyl group fused with a phenyl group, said phenyl group being possibly optionally substituted with at least one halogen atom, R⁶ is H or is selected from the following groups: nitro, cyano, (C₁-C₆)alkyl, cycloalkyl, (C₁-C₆)alkoxy, cycloalkyloxy, (C₆-C₁₀)aryl, heteroaryl, (C₆-C₁₀)aryloxy, heteroaryloxy, (C₁-C₆)alkylcarbonyl, arylcarbonyl, (C₁-C₆)alkoxycarbonyl, aryloxycarbonyl, carboxyl, amido, (C₁-C₆)alkylsulfonyl, arylsulfonyl, (C₁-C₆)alkylsulfinyl, arylsulfinyl, (C₁-C₆)alkylthio, arylthio, sulfonamide, halogen, —NRₐRᵦ, —SO₂—NRR', and —N(R꜀)—C(=O)—R꜀, $R_a$ and $R_b$ being independently selected from H and $(C_1-C_6)$alkyl, R and R' being selected from the following groups: $(C_1-C_6)$alkyl, $(C_6-C_{10})$aryl, heteroaryl, and halo$(C_1-C_6)$alkyl, $R_c$ being H or being selected from the following groups: $(C_1-C_6)$alkyl, $(C_6-C_{10})$aryl, and heteroaryl, $R_d$ being H or selected from the following groups: $(C_1-C_6)$alkyl, halo$(C_1-C_6)$alkyl, cycloalkyl, $(C_6-C_{10})$aryl, heteroaryl, $(C_1-C_6)$alkoxy, cycloalkyloxy, $(C_6-C_{10})$aryloxy, and heteroaryloxy;

$R^7$ is a $(C_1-C_6)$alkyl group;

$R^9$ is a $(C_1-C_6)$alkyl group; and $R^8$ is H, a $(C_6-C_{10})$aryl group or a $(C_1-C_6)$alkyl group; and $Y^-$ is a non-coordinating inorganic anion.

2. The optically pure (+) or (−) enantiomer of claim 1, having the following formula (II):

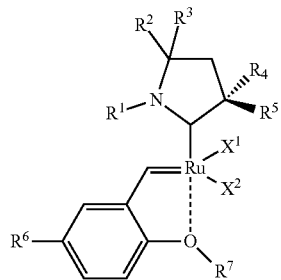

wherein:
$X^1$ is an halogen atom or a $(C_1-C_6)$alkoxy group;
$X^2$ is an halogen atom or a $(C_1-C_6)$alkoxy group;
$R^1$ is a $(C_6-C_{10})$aryl group or a $(C_1-C_6)$alkyl group, said aryl group being optionally substituted with at least one substituent chosen from the group consisting of $(C_1-C_6)$alkyl;
$R^2$ is a $(C_6-C_{10})$aryl group or a $(C_1-C_6)$alkyl group;
$R^3$ is a $(C_1-C_6)$alkyl group;
$R^4$ is a $(C_6-C_{10})$aryl group, a $(C_1-C_6)$alkyl group or a $(C_3-C_6)$cycloalkyl group, said aryl group being optionally substituted with at least one substituent chosen from the $(C_1-C_6)$alkyl groups;
$R^5$ is selected from the following groups: $(C_6-C_{10})$aryl, $(C_1-C_6)$alkyl, $(C_3-C_6)$cycloalkyl, heteroaryl, $(C_6-C_{10})$aryl$(C_1-C_6)$alkyl, and heteroaryl$(C_1-C_6)$alkyl, said aryl group being optionally substituted with at least one substituent chosen from the $(C_1-C_6)$alkyl groups;
with the proviso that $R^5$ is different from $R^4$;
$R^6$ is H, nitro or a $(C_1-C_6)$alkyl group; and
$R^7$ is a $(C_1-C_6)$alkyl group.

3. The optically pure (+) or (−) enantiomer of claim 2, wherein $X^1$ and $X^2$ are halogen atoms.

4. The optically pure (+) or (−) enantiomer of claim 2, wherein $R^1$ is a $(C_6-C_{10})$aryl group substituted with at least one substituent chosen from the group consisting of $(C_1-C_6)$alkyl.

5. The optically pure (+) or (−) enantiomer of claim 2, wherein $R^2$ is a $(C_1-C_6)$alkyl group.

6. The optically pure (+) or (−) enantiomer of claim 2, wherein $R^2$ and $R^3$ are identical.

7. The optically pure (+) or (−) enantiomer of claim 2, wherein $R^4$ and $R^5$ are different and are selected from the following groups: $(C_6-C_{10})$aryl, $(C_1-C_6)$alkyl, and $(C_3-C_6)$cycloalkyl, said aryl group being optionally substituted with two substituents selected from the $(C_1-C_6)$alkyl groups.

8. The optically pure (+) or (−) enantiomer of claim 2, wherein $R^6$ is H or nitro.

9. The optically pure (+) or (−) enantiomer of claim 1, having one of the following formulae:

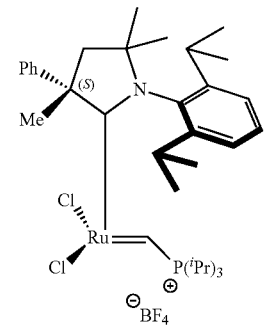

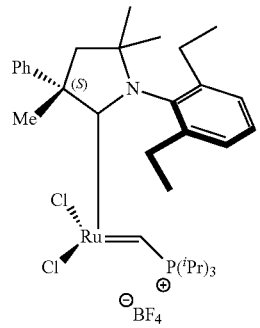

(+)-(R)-Ru-1a

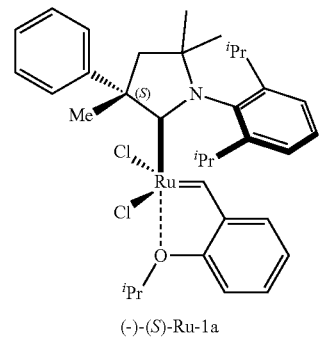

(−)-(S)-Ru-1a

-continued
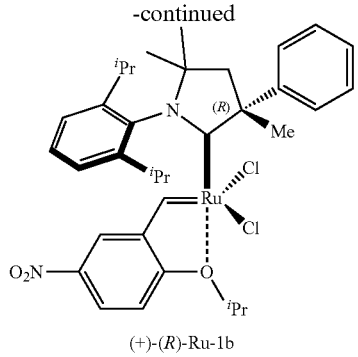
(+)-(R)-Ru-1b
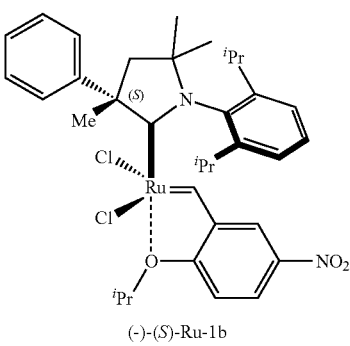
(-)-(S)-Ru-1b
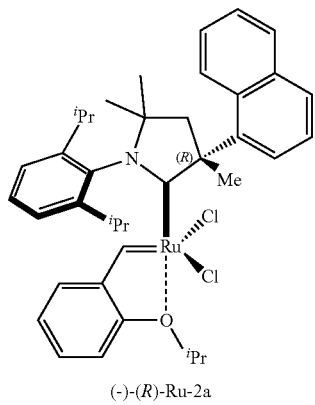
(-)-(R)-Ru-2a
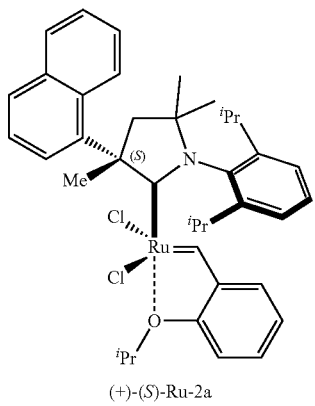
(+)-(S)-Ru-2a
-continued
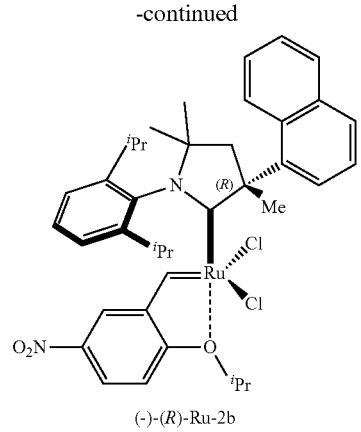
(-)-(R)-Ru-2b
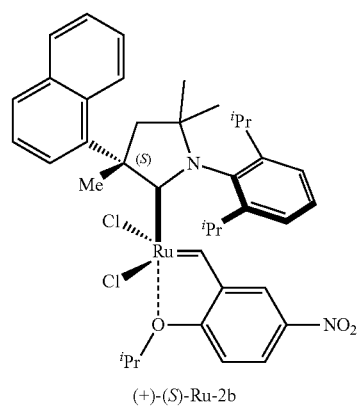
(+)-(S)-Ru-2b
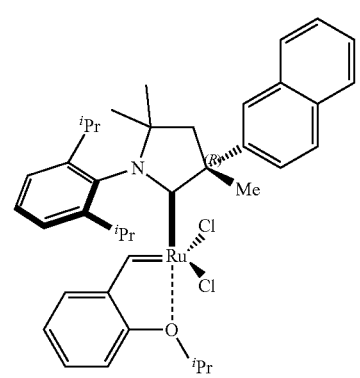
(-)-(R)-Ru-3a
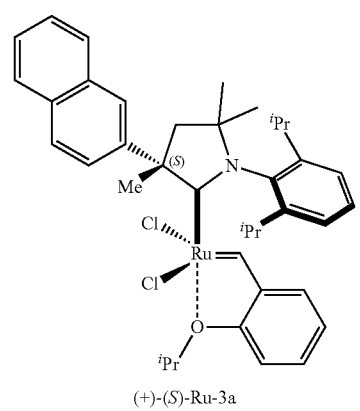
(+)-(S)-Ru-3a

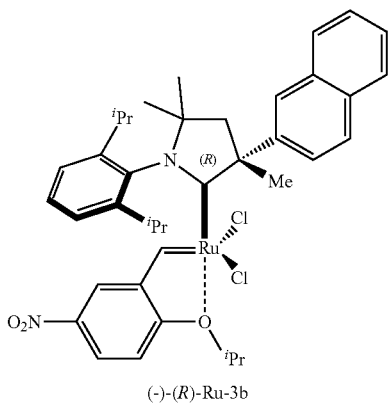
(−)-(R)-Ru-3b
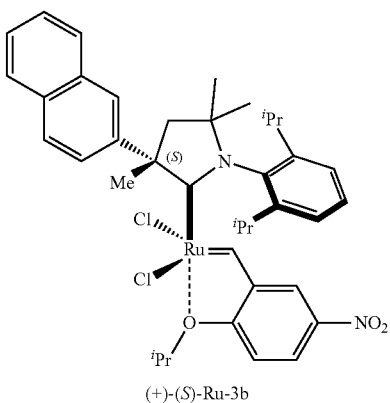
(+)-(S)-Ru-3b
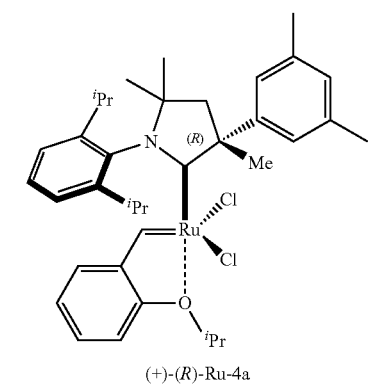
(+)-(R)-Ru-4a
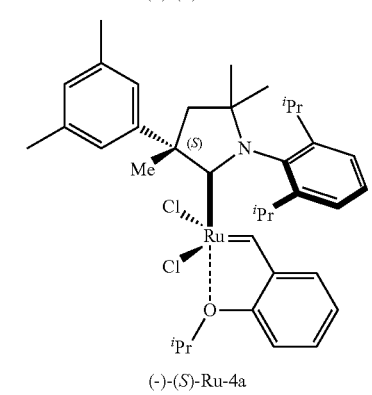
(−)-(S)-Ru-4a
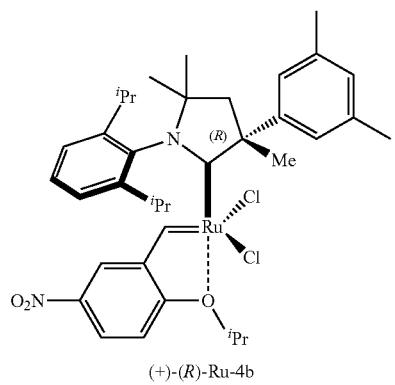
(+)-(R)-Ru-4b
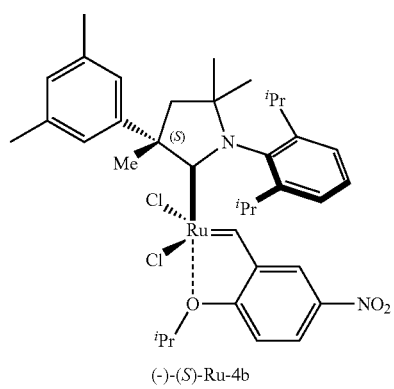
(−)-(S)-Ru-4b
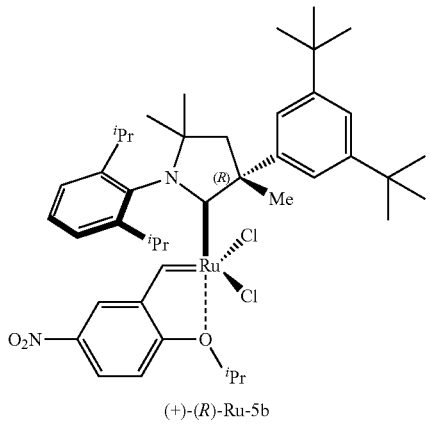
(+)-(R)-Ru-5b
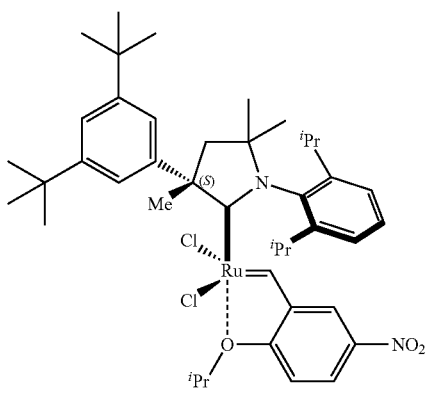
(−)-(S)-Ru-5b -continued
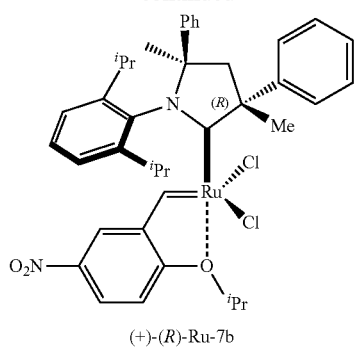
(+)-(R)-Ru-7b
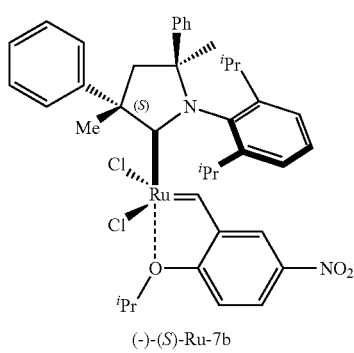
(−)-(S)-Ru-7b
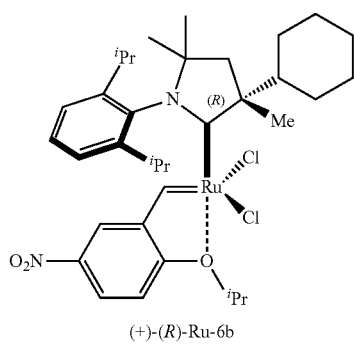
(+)-(R)-Ru-6b
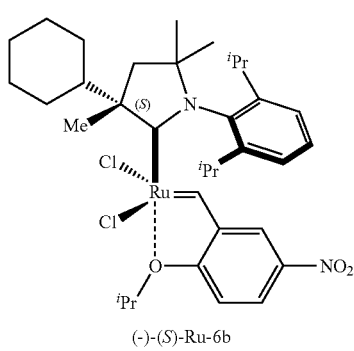
(−)-(S)-Ru-6b
-continued
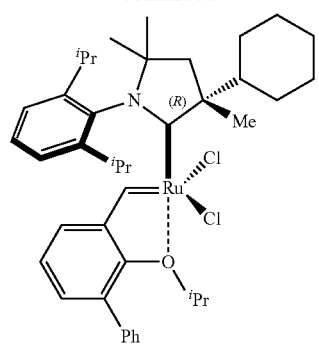
(+)-(R)-Ru-6c
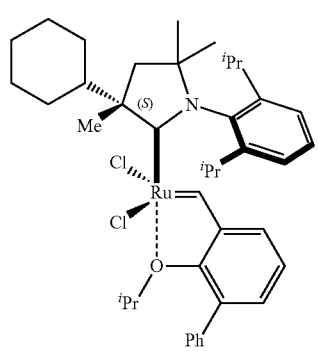
(−)-(S)-Ru-6c
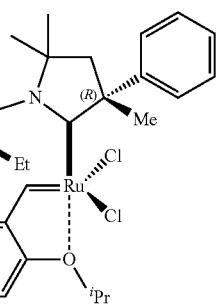
(+)-(R)-Ru-8a
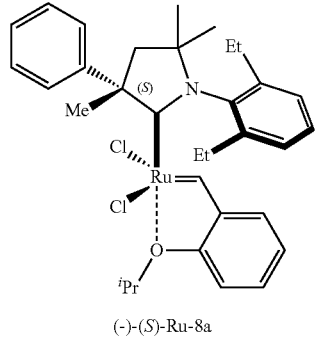
(−)-(S)-Ru-8a -continued
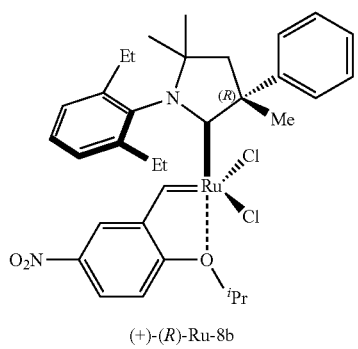
(+)-(R)-Ru-8b
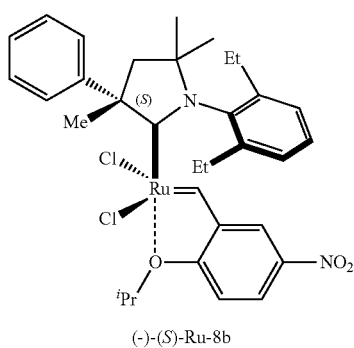
(-)-(S)-Ru-8b
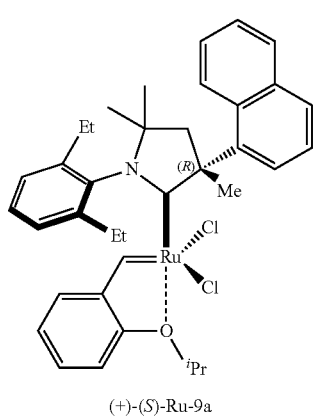
(+)-(S)-Ru-9a
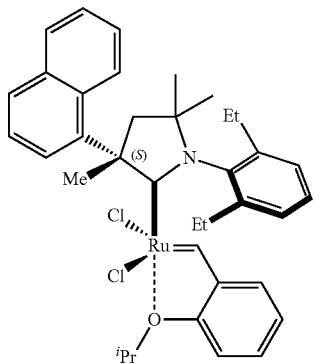
(-)-(S)-Ru-9a
-continued
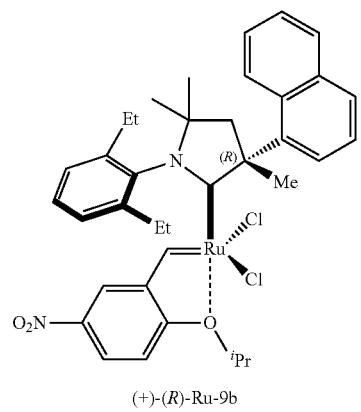
(+)-(R)-Ru-9b
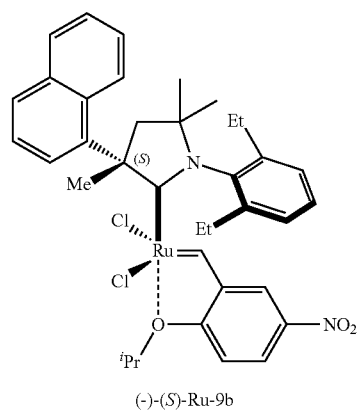
(-)-(S)-Ru-9b
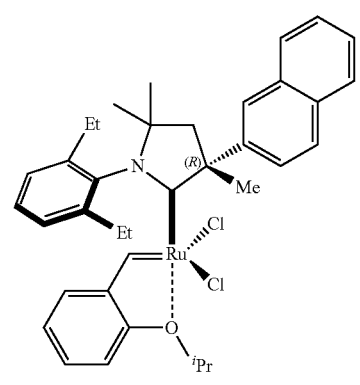
(+)-(R)-Ru-10a
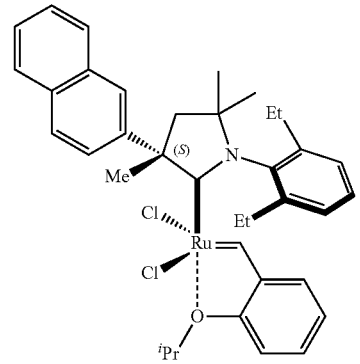
(-)-(S)-Ru-10a

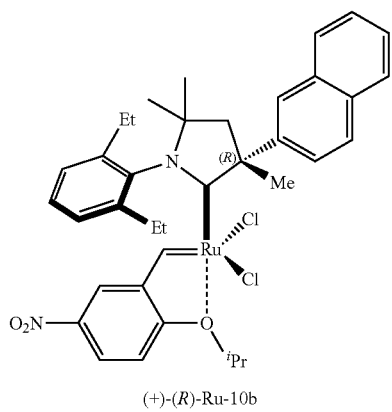
(+)-(R)-Ru-10b
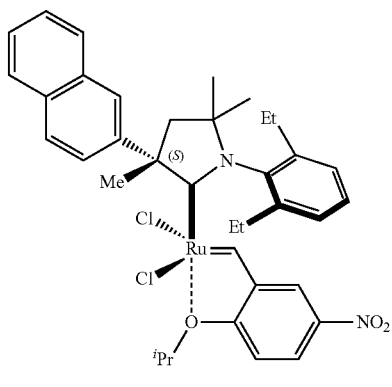
(-)-(S)-Ru-10b
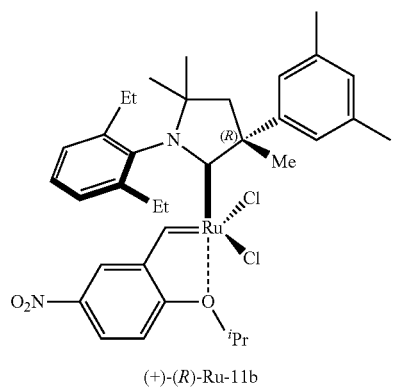
(+)-(R)-Ru-11b
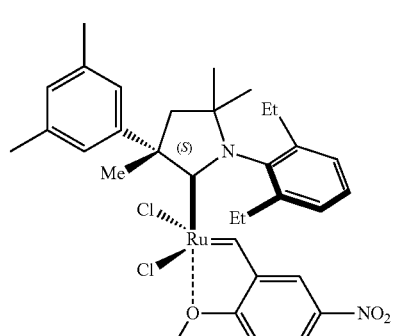
(-)-(S)-Ru-11b
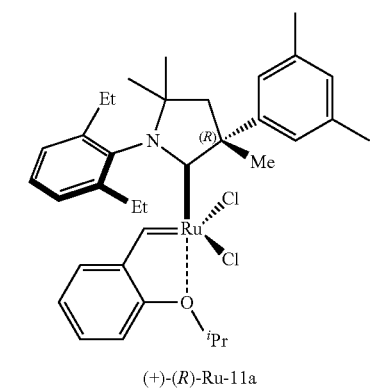
(+)-(R)-Ru-11a
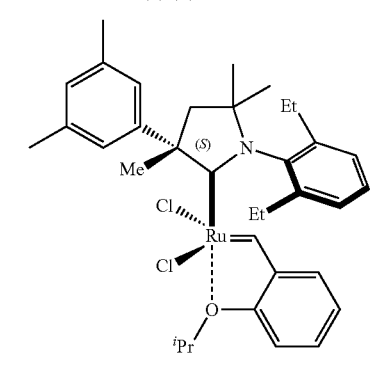
(-)-(S)-Ru-11a
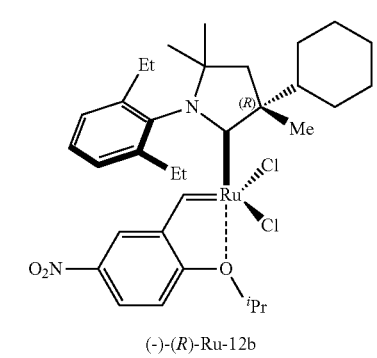
(-)-(R)-Ru-12b
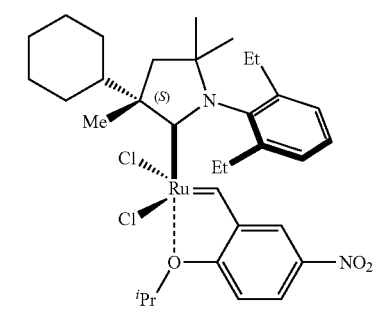
(+)-(S)-Ru-12b -continued
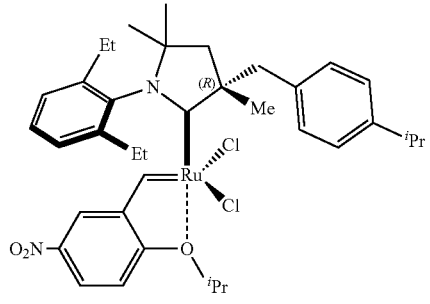
(−)-(R)-Ru-13b
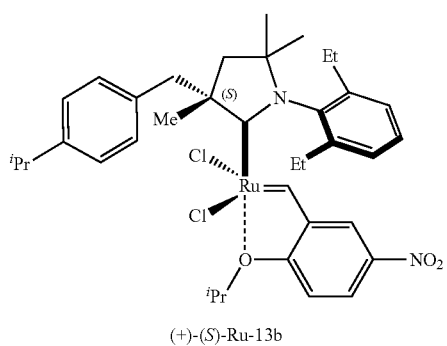
(+)-(S)-Ru-13b
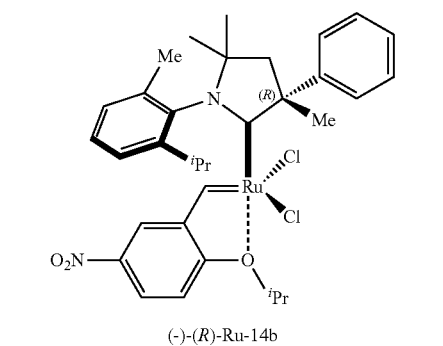
(−)-(R)-Ru-14b
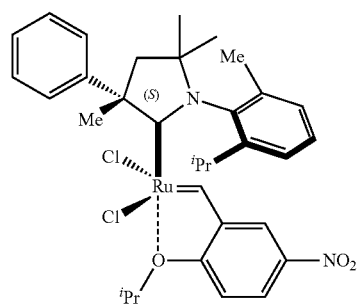
(+)-(S)-Ru-14b
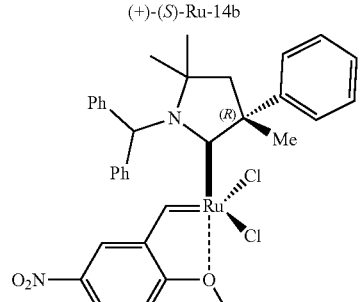
(−)-(R)-Ru-15b
-continued
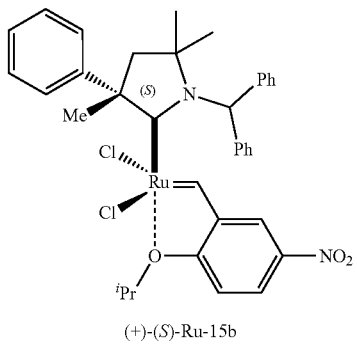
(+)-(S)-Ru-15b
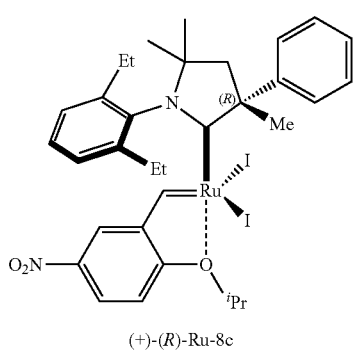
(+)-(R)-Ru-8c
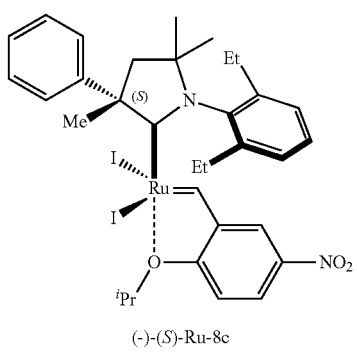
(−)-(S)-Ru-8c
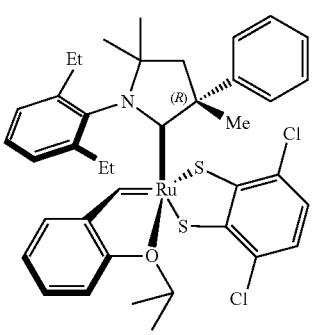
(+)-(R)-Ru-8d -continued

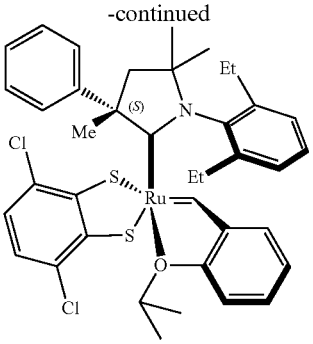

(−)-(S)-Ru-8d

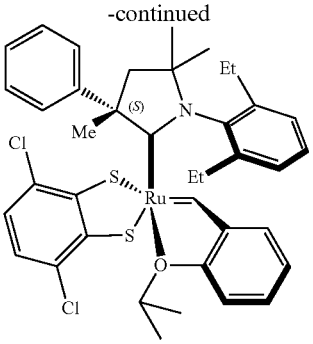

(+)-(R)-Ru-8e

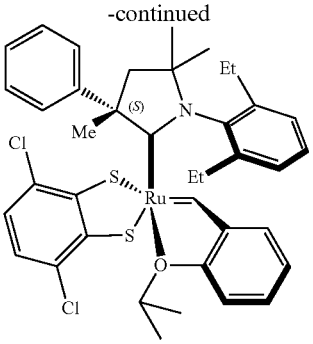

(−)-(S)-Ru-8e

10. The optically pure (+) or (−) enantiomer of claim 1 which is a catalyst.

11. A method of asymmetric olefin metathesis, comprising the use of the optically pure (+) or (−) enantiomer of claim 1 as a catalyst.

12. A process for the preparation of the optically pure (+) or (−) enantiomer of claim 1, comprising a step of chiral HPLC separation of racemic ruthenium complexes of formula (I).

13. The process of claim 12, wherein the chiral HPLC separation is carried out with a HPLC column comprising amylose substituted with chloro-phenylcarbamate as chiral stationary phase.

14. A ruthenium complex having the following formula (I'):

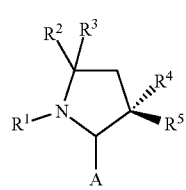

wherein:
R$^1$ is a —NR'$_a$R'$_b$ group, R'$_a$ and R'$_b$ being independently from each other selected from the group consisting of: H, (C$_1$-C$_6$)alkyl, and (C$_6$-C$_{10}$)aryl;
R$^2$ is H, a (C$_6$-C$_{10}$)aryl group or a (C$_1$-C$_6$)alkyl group;
R$^3$ is a (C$_1$-C$_6$)alkyl group; or R$^2$ and R$^3$ may together form, with the carbon atom carrying them, a (C$_3$-C$_6$)cycloalkyl;
R$^4$ is selected from the following groups: (C$_6$-C$_{20}$)aryl, (C$_1$-C$_{10}$)alkyl, and (C$_3$-C$_{12}$)cycloalkyl group, said aryl group being optionally substituted with at least one substituent chosen from the group consisting of: (C$_1$-C$_6$)alkyl, optionally substituted with one or several phenyl group(s), (C$_6$-C$_{10}$)aryl(C$_1$-C$_6$)alkyl, and (C$_6$-C$_{10}$)aryl, optionally substituted with one or several substituents, in particular selected in from the group consisting of: (C$_1$-C$_6$)alkylamino, di(C$_1$-C$_6$)alkylamino, (C$_1$-C$_6$) alcoxy, and (C$_1$-C$_6$)alkyl;
R$^5$ is selected from the following groups: (C$_6$-C$_{20}$)aryl, (C$_1$-C$_{10}$)alkyl, (C$_3$-C$_{12}$)cycloalkyl, heteroaryl, (C$_6$-C$_{10}$)aryl(C$_1$-C$_6$)alkyl, and heteroaryl(C$_1$-C$_6$)alkyl, said aryl group being optionally substituted with at least one substituent chosen from the group consisting of: (C$_1$-C$_6$)alkyl, optionally substituted with one or several phenyl group(s), (C$_6$-C$_{10}$)aryl(C$_1$-C$_6$)alkyl, and (C$_6$-C$_{10}$)aryl, optionally substituted with one or several substituents, in particular selected in from the group consisting of: (C$_1$-C$_6$)alkylamino, di(C$_1$-C$_6$)alkylamino, (C$_1$-C$_6$) alcoxy, and (C$_1$-C$_6$) alkyl;
with the proviso that R$^5$ is different from R$^4$;
A is either a group of formula (1) or a group of formula (2):

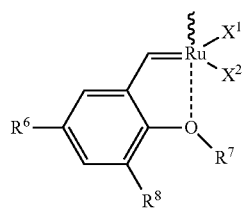

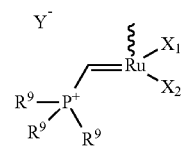

wherein:
X$^1$ is an halogen atom, a (C$_1$-C$_6$)alkoxy group or a —S—(C$_6$-C$_{10}$)aryl group;
X$^2$ is an halogen atom or a (C$_1$-C$_6$)alkoxy group;

or $X^1$ and $X^2$ may form together with the ruthenium atom carrying them a heterocycloalkyl group fused with a phenyl group, said phenyl group being possibly optionally substituted with at least one halogen atom, $R^6$ is H or is selected from the following groups: nitro, cyano, $(C_1-C_6)$alkyl, cycloalkyl, $(C_1-C_6)$alkoxy, cycloalkyloxy, $(C_6-C_{10})$aryl, heteroaryl, $(C_6-C_{10})$aryloxy, heteroaryloxy, $(C_1-C_6)$alkylcarbonyl, arylcarbonyl, $(C_1-C_6)$alkoxycarbonyl, aryloxycarbonyl, carboxyl, amido, $(C_1-C_6)$alkylsulfonyl, arylsulfonyl, $(C_1-C_6)$alkylsulfinyl, arylsulfinyl, $(C_1-C_6)$alkylthio, arylthio, sulfonamide, halogen, —$NR_aR_b$, —$SO_2$—NRR', and —$N(R_c)$—C(=O)—$R_c$, $R_a$ and $R_b$ being independently selected from H and $(C_1-C_6)$alkyl, R and R' being selected from the following groups: $(C_1-C_6)$alkyl, $(C_6-C_{10})$aryl, heteroaryl, and halo$(C_1-C_6)$alkyl, $R_c$ being H or being selected from the following groups: $(C_1-C_6)$alkyl, $(C_6-C_{10})$aryl, and heteroaryl, $R_d$ being H or selected from the following groups: $(C_1-C_6)$alkyl, halo$(C_1-C_6)$alkyl, cycloalkyl, $(C_6-C_{10})$aryl, heteroaryl, $(C_1-C_6)$alkoxy, cycloalkyloxy, $(C_6-C_{10})$aryloxy, and heteroaryloxy;

$R^7$ is a $(C_1-C_6)$alkyl group;

$R^9$ is a $(C_1-C_6)$alkyl group; and $R^8$ is H, a $(C_6-C_{10})$aryl group or a $(C_1-C_6)$alkyl group; and $Y^-$ is a non-coordinating inorganic anion, said complex being in the form of a racemic mixture, or in the form of an optically pure (+) or (−) enantiomer.

* * * * *